(12) United States Patent
Zhang et al.

(10) Patent No.: US 10,428,067 B2
(45) Date of Patent: Oct. 1, 2019

(54) COMPOUNDS AND METHODS FOR KINASE MODULATION

(71) Applicant: Plexxikon Inc., Berkeley, CA (US)

(72) Inventors: Chao Zhang, Moraga, CA (US); Guoxian Wu, Foster City, CA (US); Wayne Spevak, Berkeley, CA (US); Zuojun Guo, Pasadena, CA (US); Ying Zhang, Fremont, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 16/001,534

(22) Filed: Jun. 6, 2018

(65) Prior Publication Data

US 2018/0354946 A1 Dec. 13, 2018

Related U.S. Application Data

(60) Provisional application No. 62/516,558, filed on Jun. 7, 2017.

(51) Int. Cl.

| | | |
|---|---|---|
| *C07D 471/04* | (2006.01) |
| *A61K 31/444* | (2006.01) |
| *A61K 45/06* | (2006.01) |
| *A61K 31/4545* | (2006.01) |
| *A61K 31/397* | (2006.01) |
| *A61K 31/497* | (2006.01) |

(52) U.S. Cl.
CPC .......... *C07D 471/04* (2013.01); *A61K 31/444* (2013.01); *A61K 31/4545* (2013.01); *A61K 31/497* (2013.01); *A61K 45/06* (2013.01)

(58) Field of Classification Search
CPC .......................... C07D 471/04; A61K 31/444; A61K 31/4545; A61K 31/497; A61K 45/06
See application file for complete search history.

(56) References Cited

U.S. PATENT DOCUMENTS

| | | |
|---|---|---|
| 6,770,643 B2 | 8/2004 | Cox et al. |
| 6,875,770 B2 | 4/2005 | Matsuoka et al. |
| 6,897,207 B2 | 5/2005 | Cox et al. |
| 7,202,266 B2 | 4/2007 | Arnold et al. |
| 7,348,338 B2 | 3/2008 | Arnold et al. |
| 7,476,746 B2 | 1/2009 | Artis et al. |
| 7,491,831 B2 | 2/2009 | Artis et al. |
| 7,498,342 B2 | 3/2009 | Ibrahim et al. |
| 7,504,509 B2 | 3/2009 | Ibrahim et al. |
| 7,517,970 B2 | 4/2009 | West et al. |
| 7,531,568 B2 | 5/2009 | Lin et al. |
| 7,572,806 B2 | 8/2009 | Arnold et al. |
| 7,585,859 B2 | 9/2009 | Ibrahim et al. |
| 7,605,168 B2 | 10/2009 | Ibrahim et al. |
| 7,723,374 B2 | 5/2010 | Artis et al. |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 7,872,018 B2 | 1/2011 | Ibrahim et al. |
| 7,893,075 B2 | 2/2011 | Zhang et al. |
| 7,947,708 B2 | 5/2011 | Ibrahim et al. |
| 8,053,463 B2 | 11/2011 | Lin et al. |
| 8,067,434 B2 | 11/2011 | Ibrahim et al. |
| 8,110,576 B2 | 2/2012 | Ibrahim et al. |
| 8,119,637 B2 | 2/2012 | Ibrahim et al. |
| 8,129,404 B2 | 3/2012 | Ibrahim et al. |
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,198,273 B2 | 6/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Zhang et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,642,606 B2 | 2/2014 | Ibrahim et al. |
| 8,673,928 B2 | 3/2014 | Ibrahim et al. |
| 8,722,702 B2 | 5/2014 | Zhang et al. |

(Continued)

FOREIGN PATENT DOCUMENTS

| | | |
|---|---|---|
| EP | 2738172 | 6/2014 |
| WO | WO 2005/028475 | 3/2005 |

(Continued)

OTHER PUBLICATIONS

U.S. Appl. No. 16/123,612, filed Sep. 6, 2018, Desai et al.
U.S. Appl. No. 16/148,244, filed Oct. 1, 2018, Zhang et al.
International Search Report and Written Opinion for PCT Application No. PCT/US2018/036280 dated Sep. 11, 2018, 13 pages.
U.S. Appl. No. 15/925,270, filed Mar. 19, 2018, Lin.
U.S. Appl. No. 15/977,772, filed May 11, 2018, Ibrahim et al.
U.S. Appl. No. 16/024,197, filed Jun. 29, 2018, Ibrahim et al.
U.S. Appl. No. 16/043,821, filed Jul. 24, 2018, Ibrahim et al.
U.S. Appl. No. 16/058,945, filed Aug. 8, 2018, Wu.

(Continued)

*Primary Examiner* — Erich A Leeser
(74) *Attorney, Agent, or Firm* — Sheppard Mullin Richter & Hampton LLP

(57) ABSTRACT

Disclosed are compounds having a compound of Formula I:

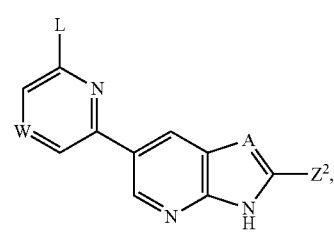

or a pharmaceutically acceptable salt, a solvate, a tautomer, an isomer or a deuterated analog thereof, compositions thereof, and uses thereof.

18 Claims, No Drawings

(56) References Cited

U.S. PATENT DOCUMENTS

| | | | |
|---|---|---|---|
| 8,785,489 B2 | 7/2014 | Abeywardane et al. | |
| 8,865,735 B2 | 10/2014 | Diodone et al. | |
| 8,901,118 B2 | 12/2014 | Zhang et al. | |
| 8,901,301 B2 | 12/2014 | Ibrahim et al. | |
| 8,912,204 B2 | 12/2014 | Ibrahim et al. | |
| 9,096,593 B2 | 8/2015 | Zhang et al. | |
| 9,150,570 B2 | 10/2015 | Ibrahim et al. | |
| 9,169,250 B2 | 10/2015 | Zhang et al. | |
| 9,249,140 B2 | 2/2016 | Heinrich et al. | |
| 9,260,437 B2 | 2/2016 | Ibrahim et al. | |
| 9,358,235 B2 | 6/2016 | Bollag et al. | |
| 9,440,969 B2 | 9/2016 | Ibrahim et al. | |
| 9,447,089 B2 | 9/2016 | Desai et al. | |
| 9,469,640 B2 | 10/2016 | Wu et al. | |
| 9,487,515 B2 | 11/2016 | Zhang et al. | |
| 9,550,768 B2 | 1/2017 | Zhang et al. | |
| 9,617,267 B2 | 4/2017 | Ibrahim et al. | |
| 9,624,213 B2 | 4/2017 | Ibrahim et al. | |
| 9,663,517 B2 | 5/2017 | Desai et al. | |
| 9,938,273 B2 * | 4/2018 | Wu | A61K 31/437 |
| 2004/0142864 A1 | 7/2004 | Bremer et al. | |
| 2004/0171062 A1 | 9/2004 | Hirth et al. | |
| 2005/0048573 A1 | 3/2005 | Artis et al. | |
| 2005/0079548 A1 | 4/2005 | Artis et al. | |
| 2005/0164300 A1 | 7/2005 | Artis et al. | |
| 2005/0170431 A1 | 8/2005 | Ibrahim et al. | |
| 2006/0030583 A1 | 2/2006 | Arnold et al. | |
| 2006/0058339 A1 | 3/2006 | Ibrahim et al. | |
| 2006/0135540 A1 | 6/2006 | Lin et al. | |
| 2006/0160135 A1 | 7/2006 | Wang et al. | |
| 2007/0066641 A1 | 3/2007 | Ibrahim et al. | |
| 2007/0072904 A1 | 3/2007 | Lin et al. | |
| 2008/0076758 A1 | 3/2008 | Folkes et al. | |
| 2008/0221127 A1 | 9/2008 | Lin et al. | |
| 2008/0234349 A1 | 9/2008 | Lin et al. | |
| 2008/0249137 A1 | 10/2008 | Lin et al. | |
| 2010/0190777 A1 | 7/2010 | Wu et al. | |
| 2011/0092538 A1 | 4/2011 | Spevak et al. | |
| 2011/0112127 A1 | 5/2011 | Zhang et al. | |
| 2011/0166174 A1 | 7/2011 | Ibrahim et al. | |
| 2011/0183988 A1 | 7/2011 | Ibrahim et al. | |
| 2012/0015966 A1 | 1/2012 | Lin et al. | |
| 2012/0053177 A1 | 3/2012 | Ibrahim et al. | |
| 2012/0122860 A1 | 5/2012 | Visor et al. | |
| 2012/0165366 A1 | 6/2012 | Ibrahim et al. | |
| 2012/0245174 A1 | 9/2012 | Ibrahim et al. | |
| 2013/0158049 A1 | 6/2013 | Alam et al. | |
| 2013/0237531 A1 | 9/2013 | Wu et al. | |
| 2013/0261117 A1 | 10/2013 | Ibrahim et al. | |
| 2013/0303534 A1 | 11/2013 | Ibrahim et al. | |
| 2014/0038948 A1 | 2/2014 | Wu et al. | |
| 2014/0128390 A1 | 5/2014 | Lin et al. | |
| 2014/0213554 A1 | 7/2014 | Wu et al. | |
| 2014/0303121 A1 | 10/2014 | Zhang et al. | |
| 2014/0303187 A1 | 10/2014 | Wu et al. | |
| 2014/0357612 A1 | 12/2014 | Zhang et al. | |
| 2015/0133400 A1 | 5/2015 | Zhang et al. | |
| 2015/0183793 A1 | 7/2015 | Zhang et al. | |
| 2015/0284397 A1 | 10/2015 | Lin et al. | |
| 2015/0290205 A1 | 10/2015 | Ibrahim et al. | |
| 2015/0368243 A1 | 12/2015 | Ibrahim | |
| 2016/0068528 A1 | 3/2016 | Zhang et al. | |
| 2016/0075712 A1 | 3/2016 | Shi et al. | |
| 2016/0176865 A1 | 6/2016 | Ibrahim et al. | |
| 2016/0243092 A1 | 8/2016 | Bollag et al. | |
| 2016/0326162 A1 | 11/2016 | Lin et al. | |
| 2016/0326168 A1 | 11/2016 | Ibrahim et al. | |
| 2016/0326169 A1 | 11/2016 | Ibrahim et al. | |
| 2016/0339025 A1 | 11/2016 | Ibrahim et al. | |
| 2016/0340357 A1 | 11/2016 | Ibrahim et al. | |
| 2016/0340358 A1 | 11/2016 | Ibrahim et al. | |
| 2017/0029413 A1 | 2/2017 | Holladay et al. | |
| 2017/0056382 A1 | 3/2017 | Wu et al. | |
| 2017/0081326 A1 | 3/2017 | Ibrahim et al. | |
| 2017/0157120 A1 | 6/2017 | Ibrahim et al. | |
| 2017/0247370 A1 | 8/2017 | Zhang et al. | |
| 2017/0267660 A1 | 9/2017 | Lin et al. | |
| 2017/0283423 A1 | 10/2017 | Zhang et al. | |
| 2017/0319559 A1 | 11/2017 | Wu et al. | |
| 2017/0320899 A1 | 11/2017 | Zhang et al. | |
| 2017/0334909 A1 | 11/2017 | Ibrahim et al. | |
| 2017/0349572 A1 | 12/2017 | Wu et al. | |
| 2017/0362231 A1 | 12/2017 | Ibrahim et al. | |
| 2018/0002332 A1 | 1/2018 | Ibrahim et al. | |
| 2018/0030051 A1 | 2/2018 | Ibrahim et al. | |
| 2018/0055828 A1 | 3/2018 | Bollag | |
| 2018/0072722 A1 | 3/2018 | Zhang et al. | |
| 2018/0099939 A1 | 4/2018 | Zhang et al. | |
| 2018/0099975 A1 | 4/2018 | Zhang et al. | |
| 2018/0111929 A1 | 4/2018 | Ibrahim | |
| 2018/0111930 A1 | 4/2018 | Desai | |
| 2018/0215763 A1 | 8/2018 | Wu et al. | |

FOREIGN PATENT DOCUMENTS

| | | |
|---|---|---|
| WO | WO 2007/013896 | 2/2007 |
| WO | WO 2010/111527 | 9/2010 |
| WO | WO 2010/129467 | 11/2010 |
| WO | WO 2013/092467 | 6/2013 |
| WO | WO 2016/106266 | 6/2016 |
| WO | WO 2016/164641 | 10/2016 |
| WO | WO 2017/100201 | 6/2017 |

OTHER PUBLICATIONS

U.S. Appl. No. 16/109,199, filed Aug. 22, 2018, Wu.
International Search Report and Written Opinion dated Apr. 20, 2017 for PCT Application No. PCT/US2016/065179. 13 pages.
U.S. Appl. No. 16/158,107, filed Oct. 11, 2018, Ibrahim et al.
U.S. Appl. No. 16/172,573, filed Oct. 26, 2018, Rezaei et al.
U.S. Appl. No. 16/219,730, filed Dec. 13, 2018, Ibrahim et al.
U.S. Appl. No. 16/358,608, filed Mar. 19, 2019, Zhang et al.

* cited by examiner

COMPOUNDS AND METHODS FOR KINASE MODULATION

CROSS-REFERENCE TO RELATED APPLICATIONS

This application claims the benefit under 35 U.S.C. § 119(e) of U.S. Provisional Application 62/516,558, filed Jun. 7, 2017, of which is hereby incorporated by reference in its entirety.

FIELD

The present disclosure relates to protein kinases and compounds which selectively modulate kinases, and uses therefor. Particular embodiments contemplate disease indications which are amenable to treatment by modulation of kinase activity by the compounds of the present disclosure.

BACKGROUND

Transforming growth factor-β (TGF-β) is secreted in an inactive form, and when activated, forms a heter-tetrameric receptor complex comprised of type 1 (TGFBR1) and type 2 (TGFBR2) receptors. The TGFBR2 gene provides instructions for making a protein called transforming growth factor-beta receptor type 2. This receptor transmits signals from the cell surface into the cell through a process called signal transduction.

To carry out its signaling function, the TGF-β receptor type 2 (TGFBR2 or TGFβR2) spans the cell membrane, so that one end of the protein projects from the outer surface of the cell (the extracellular domain) and the other end remains inside the cell (the intracellular domain). TGF-β binds to the extracellular domain of TGFBR2, which activates this receptor and allows it to bind to another receptor, TGFBR1, on the cell surface. These three proteins form a complex, triggering signal transduction by activating other proteins in a signaling pathway called the TGF-β pathway.

Signals transmitted by the TGF-β receptor complex triggers various responses by the cell, including cellular differentiation, cellular proliferation, cellular motility, and cell apoptosis. Overexpression of TGFBR2 can, therefore, be disruptive to cells.

Secondary mutations in the tyrosine kinase domain (KD) is one of the most common causes of acquired clinical resistance to small molecule tyrosine kinase inhibitors (TKIs) in human cancer. Recent pharmaceutical efforts have focused on the development of "type II" kinase inhibitors, which bind to a relatively non-conserved inactive kinase conformation and exploit an allosteric site adjacent to the ATP-binding pocket as a potential means to increase kinase selectivity. Mutations in FLT3 are the common genetic alteration in patients with acute myeloid leukemia (AML) (TCGA, *N Engl J Med.* 2013, 368: 2059-74) and are primarily comprised of constitutively activating internal tandem duplication (ITD) mutations (of 1-100 amino acids) in the juxtamembrane domain, and to a lesser extent, point mutations, typically within the kinase activation loop. Secondary KD mutations in FLT3-ITD that can cause resistance to the highly potent type II FLT3 inhibitors, such as, quizartinib, which achieved a composite complete remission (CRc) rate of about 50% in relapsed or chemotherapy-refractory FLT3-ITD+ AML patients treated in large phase II monotherapy studies (Tallman et al., *Blood,* 2013; 122:494). An in vitro saturation mutagenesis screen of FLT3-ITD identified five quizartinib-resistant KD mutations at three residues: the "gatekeeper" F691 residue, and two amino acid positions within the kinase activation loop (D835 and Y842), a surprisingly limited spectrum of mutations for a type II inhibitor. Mutation at residue D835V/Y/F was subsequently identified in each of eight samples analyzed at the time of acquired clinical resistance to quizartinib (Smith et al., Nature, 2012; 485:260-3). This finding validated FLT3 as a therapeutic target in AML. The type II multikinase inhibitor sorafenib, which also has some clinical activity in FLT3-ITD+ AML, is ineffective against all identified quizartinib resistance-causing mutants, in addition to other mutant isoforms (Smith et al.). The type I inhibitor crenolanib has been identified a type I inhibitor of quizartinib-resistant D835 mutants (Zimmerman et al. *Blood,* 2013; 122:3607-15).

Accordingly, there is a need for novel compounds that inhibit one or both TGFBR2 and FLT3 kinases with secondary mutations for the treatment of various diseases.

SUMMARY

The present disclosure relates to compounds which selectively modulate TGFBR2, compositions thereof, and uses therefor. Particular embodiments contemplate disease indications which are amenable to treatment by modulation of kinase activity by the compounds of the present disclosure.

One embodiment of the disclosure relates to novel 2,5 substituted azaindole compounds, as described herein, or a pharmaceutically acceptable salt, a solvate, a tautomer, an isomer or a deuterated analog thereof, wherein these novel compounds can modulate TGFBR2.

Another embodiment of the disclosure relates to a pharmaceutical composition comprising a compound having any of the Formulae described in this disclosure, including any one of the compounds listed in Table I, or a pharmaceutically acceptable salt, a solvate, a tautomer, an isomer or a deuterated analog of any of these compounds, and a pharmaceutically acceptable carrier or excipient.

Another embodiment of the disclosure relates to a pharmaceutical composition comprising a compound having any of the Formulae described in this disclosure, including any one of the compounds listed in Table I, or a pharmaceutically acceptable salt, a solvate, a tautomer, an isomer or a deuterated analog of any of these compounds, another therapeutic agent, and a pharmaceutically acceptable carrier or excipient.

Another embodiment of the disclosure relates to a method for treating a subject in need thereof with a disease or condition mediated by TGFBR2, said method comprising administering to the subject an effective amount a compound having any of the Formulae described in this disclosure, including any one of the compounds listed in Table I, or a pharmaceutically acceptable salt, a solvate, a tautomer, an isomer or a deuterated analog of any of these compounds, wherein the disease or condition is selected from cancer, fibrosis, cardiovascular disease, or lung disease. Another embodiment of the disclosure relates to a method for treating a subject in need thereof with a disease or condition mediated by TGFBR2 or a FLT3 mutated kinase, said method comprising administering to the subject an effective amount a compound having any of the Formulae described in this disclosure, including any one of the compounds listed in Table I, or a pharmaceutically acceptable salt, a solvate, a tautomer, an isomer or a deuterated analog of any of these compounds, wherein the disease or condition is selected from cancer, fibrosis, cardiovascular disease, or lung disease.

Another embodiment of the disclosure relates to a method for treating a subject suffering from a disease or condition as described herein, said method comprising administering to the subject a pharmaceutical composition comprising a compound having any of the Formulae described in this disclosure, including any one of the compounds listed in Table I, or a pharmaceutically acceptable salt, a solvate, a tautomer, an isomer or a deuterated analog of any of these compounds, and another therapeutic agent, wherein the other therapeutic agent is selected from: an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an antibody therapy agent selected from alemtuzumab, bevacizumab, cetuximab, galiximab, gemtuzumab, nivolumab, ipilimumab, panitumumab, pembrolizumab, pertuzumab, rituximab, tositumomab, trastuzumab, and 90 Y ibritumomab tiuxetan; v) a hormone or hormone antagonist selected from the group consisting of anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor; xv) a Mek inhibitor; xvi) a tyrosine kinase inhibitor; xvii) an EGFR inhibitor; and xviii) an anti-retroviral agent selected from entry inhibitors, fusion inhibitors, reverse transcriptase inhibitors, nucleoside/nucleotide reverse transcriptase inhibitors, non-nucleoside reverse transcriptase inhibitors, integrase inhibitors, protease inhibitors, and multi-class combination products.

DETAILED DESCRIPTION

I. Definitions

As used herein the following definitions apply unless clearly indicated otherwise:

It is noted here that as used herein and the appended claims, the singular forms "a," "an," and "the" include plural reference unless the context clearly dictates otherwise.

Unless a point of attachment indicates otherwise, the chemical moieties listed in the definitions of the variables of Formula I of this disclosure, and all the embodiments thereof, are to be read from left to right, wherein the right hand side is directly attached to the parent structure as defined. However, if a point of attachment is shown on the left hand side of the chemical moiety (e.g., -alkoxy-($C_1$-$C_{25}$)alkyl), then the left hand side of this chemical moiety is attached directly to the parent moiety as defined. It is assumed that when considering generic descriptions of compounds of the described herein for the purpose of constructing a compound, such construction results in the creation of a stable structure. That is, one of ordinary skill in the art would recognize that theoretically some constructs which would not normally be considered as stable compounds (that is, sterically practical and/or synthetically feasible).

"Halogen" or "halo" refers to all halogens, that is, chloro (Cl), fluoro (F), bromo (Br), or iodo (I).

"Hydroxyl" or "hydroxy" refers to the group —OH.

"Heteroatom" is meant to include oxygen (O), nitrogen (N), and sulfur (S).

"Alkyl" by itself or as part of another substituent, means, unless otherwise stated, a straight or branched chain hydrocarbon, having the number of carbon atoms designated (i.e. $C_{1-6}$ means one to six carbons). Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, arylalkyl, cycloalkylalkyl, heterocycloalkylalkyl, heteroarylalkyl, etc.), when a prefix is not included to indicate the number of carbon atoms in an alkyl portion, the alkyl moiety or portion thereof will have 12 or fewer main chain carbon atoms or 8 or fewer main chain carbon atoms or 6 or fewer main chain carbon atoms. For example, $C_{1-6}$ alkyl refers to a straight or branched hydrocarbon having 1, 2, 3, 4, 5 or 6 carbon atoms and includes, but is not limited to, $C_{1-2}$ alkyl, $C_{1-4}$ alkyl, $C_{2-6}$ alkyl, $C_{2-4}$ alkyl, $C_{1-6}$ alkyl, $C_{2-8}$ alkyl, $C_{1-7}$ alkyl, $C_{2-7}$ alkyl and $C_{3-6}$ alkyl. The term alkyl is meant to encompass alkenyl and alkynyl as defined herein.

While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety.

"Alkylene" by itself or as part of another substituent means a linear or branched saturated divalent hydrocarbon moiety derived from an alkane having the number of carbon atoms indicated in the prefix. For example, (i.e., $C_{1-6}$ means one to six carbons; $C_{1-6}$ alkylene is meant to include methylene, ethylene, propylene, 2-methylpropylene, pentylene, hexylene and the like). $C_{1-4}$ alkylene includes methylene —$CH_2$—, ethylene —$CH_2CH_2$—, propylene —$CH_2CH_2CH_2$—, and isopropylene —$CH(CH_3)CH_2$—, —$CH_2CH(CH_3)$—, —$CH_2$—$(CH_2)_2CH_2$—, —$CH_2$—$CH(CH_3)CH_2$—, —$CH_2$—$C(CH_3)_2$—$CH_2$—$CH_2CH(CH_3)$—. Typically, an alkyl (or alkylene) group will have from 1 to 24 carbon atoms, with those groups having 10 or fewer, 8 or fewer, or 6 or fewer carbon atoms. When a prefix is not included to indicate the number of carbon atoms in an alkylene portion, the alkylene moiety or portion thereof will have 12 or fewer main chain carbon atoms or 8 or fewer main chain carbon atoms, 6 or fewer main chain carbon atoms, or 4 or fewer main chain carbon atoms, or 3 or fewer main chain carbon atoms, or 2 or fewer main chain carbon atoms, or 1 carbon atom.

"Alkenyl" refers to a linear monovalent hydrocarbon radical or a branched monovalent hydrocarbon radical having the number of carbon atoms indicated in the prefix and containing at least one double bond. For example, ($C_2$-$C_6$) alkenyl is meant to include ethenyl, propenyl, and the like. The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡CCH₃), and the like. When a prefix is not included to indicate the number of carbon atoms in an alkenyl or alkynyl portion, the alkenyl or alkynyl moiety or portion thereof will have 12 or fewer main chain carbon atoms or 8 or fewer main chain carbon atoms, 6 or fewer main chain carbon atoms or 4 or fewer main chain carbon atoms. The term "alkenylene" refers to a linear divalent hydrocarbon radical or a branched divalent hydrocarbon radical containing at least one double bond and having the number of carbon atoms indicated in the prefix. The term "alkynylene" refers to a linear divalent hydrocarbon radical or a branched divalent hydrocarbon radical containing at least one triple bond and having the number of carbon atoms indicated in the prefix. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

"Alkoxy" or "alkoxyl" refers to a —O-alkyl group, where alkyl is as defined herein. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

"Amino" or "amine" denotes the group —$NH_2$.

The term "cyano" refers to the group —CN.

"Alkylamino" refers to a —NH-alkyl group, where alkyl is as defined herein. Exemplary alkylamino groups include $CH_3NH$—, ethylamino, and the like.

"Aryl" by itself, or as part of another substituent, unless otherwise stated, refers to a monocyclic, bicyclic or polycyclic polyunsaturated aromatic hydrocarbon radical containing 6 to 14 ring carbon atoms, which can be a single ring or multiple rings (up to three rings) which are fused together or linked covalently. Non-limiting examples of unsubstituted aryl groups include phenyl, 1-naphthyl and 2-naphthyl. The term "arylene" refers to a divalent aryl, wherein the aryl is as defined herein.

"Arylalkyl" or "aralkyl" refers to -(alkylene)-aryl, where the alkylene group is as defined herein and has the indicated number of carbon atoms, or if unspecified having six or fewer main chain carbon atoms or four or fewer main chain carbon atoms; and aryl is as defined herein. Examples of arylalkyl include benzyl, phenethyl, 1-methylbenzyl, and the like.

"Cycloalkyl" or "Carbocycle" by itself, or as part of another substituent, unless otherwise stated, refers to saturated or unsaturated, non-aromatic monocyclic, bicyclic or tricyclic carbon ring systems having the number of carbon atoms indicated in the prefix or if unspecified having 3-10, also 3-8, and also 3-6, ring members per ring, such as cyclopropyl, cyclopentyl, cyclohexyl, 1-cyclohexenyl, adamantyl, and the like, where one or two ring carbon atoms may optionally be replaced by a carbonyl. Cycloalkyl refers to hydrocarbon rings having the indicated number of ring atoms (e.g., $C_{3-8}$ cycloalkyl means three to eight ring carbon atoms). "Cycloalkyl" or "carbocycle" may form a bridged ring or a spiro ring. The cycloalkyl group may have one or more double or triple bond(s), in which case they would be termed cycloalkenyl and cycloalkynyl respectively.

"Cycloalkylalkyl" refers to an -(alkylene)-cycloalkyl group where alkylene as defined herein has the indicated number of carbon atoms or if unspecified having six or fewer, or four or fewer main chain carbon atoms; and cycloalkyl is as defined herein has the indicated number of carbon atoms or if unspecified having 3-10, also 3-8, and also 3-6, ring members per ring. $C_{3-8}$cycloalkyl-$C_{1-2}$alkyl is meant to have 3 to 8 ring carbon atoms and 1 to 2 alkylene chain carbon atoms. Exemplary cycloalkylalkyl includes, e.g., cyclopropylmethylene, cyclobutylethylene, cyclobutylmethylene, and the like.

"Cycloalkenyl" by itself, or as part of another substituent, unless otherwise stated, refers to a non-aromatic monocyclic, bicyclic or tricyclic carbon ring system having the number of carbon atoms indicated in the prefix or if unspecified having 3-10, also 3-8, and also 3-6, ring members per ring, which contains at least one carbon-carbon double bond. Exemplary cycloalkenyl includes, e.g., 1-cyclohexenyl, 4-cyclohexenyl, 1-cyclopentenyl, 2-cyclopentenyl and the like. "Cycloalkynyl" by itself, or as part of another substituent, unless otherwise stated, refers to a non-aromatic monocyclic, bicyclic or tricyclic carbon ring system having the number of carbon atoms indicated in the prefix or if unspecified having 3-10, also 3-8, and also 3-6, ring members per ring, which contains at least one carbon-carbon triple bond.

The term "cyanoalkyl" or "cyanoalkylene" refers to an alkyl or alkylene as defined herein substituted by at least one cyano group as defined herein. The term "cyanocycloalkyl" refers to a cycloalkyl group as defined herein substituted by at least one cyano group, and the term "cyanocycloalkylalkyl" refers to a cycloalkylalkyl group as defined herein substituted by at least one cyano group.

The term "haloalkyl" refers to an alkyl substituted by one to seven halogen atoms. Haloalkyl includes monohaloalkyl or polyhaloalkyl. For example, the term "$C_{1-6}$haloalkyl" is mean to include trifluoromethyl, difluoromethyl, 2,2,2-trifluoroethyl, 4-chlorobutyl, 3-bromopropoyl, and the like.

The term "hydroxyalkyl" or "hydroxyalkylene" refers to an alkyl or alkylene as defined herein substituted by at least one hydroxy group as defined herein.

"Heteroaryl" by itself, or as part of another substituent, refers to a monocyclic aromatic ring radical containing 5 or 6 ring atoms, or a bicyclic aromatic radical having 8 to 10 atoms, containing one or more, 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, indolyl, triazinyl, quinoxalinyl, cinnolinyl, phthalaziniyl, benzotriazinyl, benzimidazolyl, benzopyrazolyl, benzotriazolyl, benzisoxazolyl, isobenzofuryl, isoindolyl, indolizinyl, benzotriazinyl, thienopyridyl, thienopyrimidinyl, pyrazolopyrimidinyl, imidazopyridines, benzothiaxolyl, benzothienyl, quinolyl, isoquinolyl, indazolyl, pteridinyl and thiadiazolyl. "Nitrogen containing heteroaryl" refers to heteroaryl wherein any of the heteroatoms is N.

"Heteroarylene" by itself or as part of another substituent, refers to a divalent heteroaryl, where the heteroaryl is as defined herein.

"Heteroarylalkyl" refers to -(alkylene)-heteroaryl, where the alkylene group is as defined herein and has the indicated number of carbon atoms, or if unspecified having six or fewer main chain carbon atoms or four or fewer main chain carbon atoms; and heteroaryl is as defined herein.

"Heterocycloalkyl" refers to a saturated or unsaturated non-aromatic cycloalkyl group that contains from one to five heteroatoms selected from N, O, and S, wherein the nitrogen and sulfur atoms are optionally oxidized, and the nitrogen atom(s) are optionally quaternized, the remaining ring atoms being C, where one or two C atoms may optionally be replaced by a carbonyl. The heterocycloalkyl may be a monocyclic, a bicyclic or a polycyclic ring system of 3 to 12, or 4 to 10 ring atoms, or 5 to 8 ring atoms in which one to five ring atoms are heteroatoms selected from —N=, —N—, —O—, —S—, —S(O)—, or —S(O)$_2$— and further wherein one or two ring atoms are optionally replaced by a —C(O)— group. The heterocycloalkyl can also be a heterocyclic alkyl ring fused (including spirocyclic groups) with a cycloalkyl, an aryl or a heteroaryl ring. Non limiting examples of heterocycloalkyl groups include pyrrolidinyl, piperidinyl, imidazolidinyl, benzofuranyl, pyrazolidinyl, morpholinyl, oxetanyl, and the like. A heterocycloalkyl group can be attached to the remainder of the molecule through a ring carbon or a heteroatom. The term "heterocycloalkylene" refers to a divalent heterocycloalkyl, wherein the heterocycloalkyl is as defined herein. "Heterocycloalkenyl" refers to a heterocycloalkyl group as defined herein that contains at least one alkenyl group as defined herein.

"Heterocycloalkylene" by itself or as part of another substituent, refers to a divalent heterocycloalkyl, where the heterocycloalkyl is as defined herein.

"Heterocycloalkylalkyl" or "heterocyclylalkyl" refers to -(alkylene)-heterocycloalkyl, where the alkylene group is as defined herein and has the indicated number of carbon atoms, or if unspecified having six or fewer main chain carbon atoms or four or fewer main chain carbon atoms; and heterocycloalkyl is as defined herein.

"Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, *Tetrahedron* 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), carbamates, amides, N-sulfonyl derivatives, groups of formula —C(O)OR, wherein R is, for example, methyl, ethyl, t-butyl, benzyl, phenylethyl, CH$_2$=CHCH$_2$—, and the like, groups of the formula —C(O)R', wherein R' is, for example, methyl, phenyl, trifluoromethyl, and the like, groups of the formula —SO$_2$R", wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like, CURRENT PROTOCOLS IN NUCLEIC ACID CHEMISTRY, John Wiley and Sons, New York, Volume 1, 2000).

"Optional" or "optionally" as used throughout the disclosure means that the subsequently described event or circumstance may or may not occur, and that the description includes instances where the event or circumstance occurs and instances in which it does not. For example, the phrase "the aromatic group is optionally substituted with one or two alkyl substituents" means that the alkyl may but need not be present, and the description includes situations where the aromatic group is substituted with an alkyl group and situations where the aromatic group is not substituted with the alkyl group.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

"Pharmaceutically acceptable salt" refers to a salt which is acceptable for administration to a patient, such as a mammal (e.g., salts having acceptable mammalian safety for a given dosage regime). Such salts can be derived from pharmaceutically acceptable inorganic or organic bases and from pharmaceutically-acceptable inorganic or organic acids, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Salts derived from pharmaceutically acceptable inorganic bases include aluminum, ammonium, calcium, copper, ferric, ferrous, lithium, magnesium, manganic, manganous, potassium, sodium, zinc and the like. Salts derived from pharmaceutically acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, N,N'-dibenzylethylenediamine, chloroprocaine, choline, diethanolamine, meglumine (N-methyl-glucamine) and the like. When compounds of the present disclosure contain relatively basic functionalities, acid addition salts can be obtained by contacting the neutral form of such compounds with a sufficient amount of the desired acid, either neat or in a suitable inert solvent. Salts derived from pharmaceutically acceptable acids include acetic, trifluoroacetic, propionic, ascorbic, benzenesulfonic, benzoic, camphorsulfonic, citric, ethanesulfonic, fumaric, glycolic, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, hydroiodic, carbonic, tartaric, p-toluenesulfonic, pyruvic, aspartic, benzoic, anthranilic, mesylic, salicylic, p-hydroxybenzoic, phenylacetic, embonic (pamoic), ethanesulfonic, benzenesulfonic, 2-hydroxyethanesulfonic, sulfanilic, stearic, cyclohexylaminosulfonic, algenic, hydroxybutyric, galactaric and galacturonic acid and the like.

Also included are salts of amino acids such as arginate and the like, and salts of organic acids like glucuronic or galactunoric acids and the like (see, for example, Berge, S. M. et al, "Pharmaceutical Salts," J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

As used herein in connection with compounds of the disclosure, the term "synthesizing" and like terms means chemical synthesis from one or more precursor materials.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), carbon-14 ($^{14}$C), carbon-11 ($^{11}$C) or fluorine-18 ($^{18}$F). All isotopic variations of the compounds of the present disclosure, whether radioactive or not, are intended to be encompassed within the scope of the present disclosure.

The term "deuterated" as used herein alone or as part of a group, means substituted deuterium atoms. The term "deuterated analog" as used herein alone or as part of a group, means substituted deuterium atoms in place of hydrogen. The deuterated analog of the disclosure may be a fully or partially deuterium substituted derivative. In some embodiments, the deuterium substituted derivative of the disclosure holds a fully or partially deuterium substituted alkyl, aryl or heteroaryl group.

The disclosure also embraces isotopically-labeled compounds of the present disclosure which are identical to those recited herein, but for the fact that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Unless otherwise stated, when a position is designated specifically as "H" or "hydrogen", the position is understood to have hydrogen at its natural abundance isotopic composition or its isotopes, such as deuterium (D) or tritium ($^3$H). Certain isotopically-labeled compounds of the present disclosure (e.g., those labeled with $^3$H and $^{14}$C) are useful in compound and/or substrate tissue distribution assays. Tritiated (i.e., $^3$H) and carbon-14 (i.e., $^{14}$C) and fluorine-18 ($^{18}$F) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those described in the Schemes and in the Examples herein below, by substituting an isotopically labeled reagent for a non-isotopically labeled reagent.

"Prodrugs" means any compound which releases an active parent drug according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds of Formula I wherein a hydroxy, amino, carboxyl or sulfhydryl group in a compound of Formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds of Formula I, and the like. Preparation, selection, and use of prodrugs is discussed in T. Higuchi and V. Stella, "Pro-drugs as Novel Delivery Systems," Vol. 14 of the A.C.S. Symposium Series; "Design of Prodrugs", ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

"Tautomer" means compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N═C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism ('tautomerism') can occur. The compounds described herein may have one or more tautomers and therefore include various isomers. A person of ordinary skill in the art would recognize that other tautomeric ring atom arrangements are possible. All such isomeric forms of these compounds are expressly included in the present disclosure.

"Isomers" mean compounds having identical molecular Formulae but differ in the nature or sequence of bonding of their atoms or in the arrangement of their atoms in space. Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 6th edition J. March, John Wiley and Sons, New York, 2007) differ in the chirality of one or more stereocenters.

Certain compounds of the present disclosure can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure.

Certain compounds of the present disclosure may exist in multiple crystalline or amorphous forms. In general, all physical forms are equivalent for the uses contemplated by the present disclosure and are intended to be within the scope of the present disclosure.

"Solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the subject molecule constitutes a significantly greater proportion of the biomolecules in a composition than the proportion observed in a prior composition, e.g., in a cell culture. The greater proportion can be 2-fold, 5-fold, 10-fold, or more than 10-fold, with respect to the proportion found in the prior composition.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

In the present context, the term "therapeutically effective" or "effective amount" indicates that a compound or material or amount of the compound or material when administered is sufficient or effective to prevent, alleviate, or ameliorate one or more symptoms of a disease, disorder or medical condition being treated, and/or to prolong the survival of the subject being treated. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the terms "ligand" and "modulator" are used equivalently to refer to a compound that changes (i.e., increases or decreases) the activity of a target biomolecule, e.g., an enzyme such as a kinase. Generally a ligand or modulator will be a small molecule, where "small molecule refers to a compound with a molecular weight of 1500 Daltons or less, 1000 Daltons or less, 800 Daltons or less, or 600 Daltons or less. Thus, an "improved ligand" is one that possesses better pharmacological and/or pharmacokinetic properties than a reference compound, where "better" can be defined by one skilled in the relevant art for a particular biological system or therapeutic use.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. In some embodiments, a binding compound interacts with a specified target with a dissociation constant (KD) of 1 mM or less, 1 M or less, 100 nM or less, 10 nM or less, or 1 nM or less. In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

The terms "prevent," "preventing," "prevention" and grammatical variations thereof as used herein, refers to a method of partially or completely delaying or precluding the onset or recurrence of a disease, disorder or condition and/or one or more of its attendant symptoms or barring a subject from acquiring or reacquiring a disorder or condition or reducing a subject's risk of acquiring or requiring a disorder or condition or one or more of its attendant symptoms.

"Unit dosage form" refers to a composition intended for a single administration to treat a subject suffering from a disease or medical condition. Each unit dosage form typically comprises each of the active ingredients of this disclosure plus pharmaceutically acceptable excipients. Examples of unit dosage forms are individual tablets, individual capsules, bulk powders, liquid solutions, ointments, creams, eye drops, suppositories, emulsions or suspensions. Treatment of the disease or condition may require periodic administration of unit dosage forms, for example: one unit dosage form two or more times a day, one with each meal, one every four hours or other interval, or only one per day.

The expression "oral unit dosage form" indicates a unit dosage form designed to be taken orally.

The terms "modulate," "modulation," and the like refer to the ability of a compound to increase or decrease the function and/or expression of a protein kinase, such as TGFBR2, where such function may include transcription regulatory activity and/or protein-binding. In some embodiments, the protein kinase is TGFBR2. In some embodiments, the protein kinase is a FLT3 mutated kinase. Modulation may occur in vitro or in vivo. Such activity is typically indicated in terms of an inhibitory concentration ($IC_{50}$) or excitation concentration ($EC_{50}$) of the compound for an inhibitor or activator, respectively, with respect to, for example, the protein kinase. Modulation, as described herein, includes the inhibition, antagonism, partial antagonism, activation, agonism or partial agonism of a function or characteristic associated with TGFBR2, either directly or indirectly, and/or the upregulation or downregulation of the expression of TGFBR2, either directly or indirectly. In some embodiments, modulation, as described herein, includes the inhibition, antagonism, partial antagonism, activation, agonism or partial agonism of a function or characteristic associated with FLT3 mutated kinase, either directly or indirectly, and/or the upregulation or downregulation of the expression of FLT3 mutated kinase, either directly or indirectly. In another embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules, e.g., in the case of TGFBR2, other tyrosine kinases or even other type of enzymes. In particular embodiments, the greater specificity is at least 2, 3, 4, 5, 8, 10, 50, 100, 200, 400, 500, or 1000-fold greater specificity.

As used herein in connection with binding compounds or ligands, the term "specific for TGFBR2 kinase," "specific for TGFBR2," and terms of like import mean that a particular compound binds to TGFBR2 to a statistically greater extent than to other kinases that may be present in a particular sample. Also, where biological activity other than binding is indicated, the term "specific for TGFBR2" indicates that a particular compound has greater biological effect associated with binding TGFBR2 than to other tyrosine kinases, e.g., kinase activity inhibition. The specificity is also with respect to other biomolecules (not limited to tyrosine kinases) that may be present in a particular sample. The term "specific for TGFBR2 kinase," "specific for TGFBR2," and terms of like import mean that a particular compound binds to TGFBR2 to a statistically greater extent than to other kinases that may be present in a particular sample. Also, where biological activity other than binding is indicated, the term "specific for TGFBR2" indicates that a particular compound has greater biological effect associated with binding TGFBR2 than to other tyrosine kinases, e.g., kinase activity inhibition. The specificity is also with respect to other biomolecules (not limited to tyrosine kinases) that may be present in a particular sample.

The term "first line cancer therapy" refers to therapy administered to a subject as an initial regimen to reduce the number of cancer cells. First line therapy is also referred to as induction therapy, primary therapy and primary treatment. Commonly administered first-line therapy for AML is cytarabine-based therapy in which cytarabine is administered often in combination with one or more agents selected from daunorubicin, idarubicin, doxorubicin, mitoxantrone, tipifamib, thioguanine or gemtuzumab ozogamicin. Common regimens used in cytarabine-based therapy include the "7+3" or "5+2" therapy comprising administration of cytarabine with an anthracycline such as daunorubicin or idarubicin. Another first-line therapy is clofarabine-based therapy in which clofarabine is administered, often in combination with an anthracycline such as daunorubicin, idarubicin or doxorubicin. Other first-line therapy for AML are etoposide-based therapy in which etoposide is administered, often in combination with mitoxantrone, and optionally, with cytarabine. Another first-line therapy for AML (for subtype M3, also called acute promyelocytic leukemia) is all-trans-retinoic acid (ATRA). It is recognized that what is considered "first line therapy" by those of ordinary skill in the art will continue to evolve as new anti-cancer agents are developed and tested in the clinics. A summary of the currently accepted approaches to first line treatment is described in NCCN Clinical Practice Guidelines in Oncology for acute myeloid leukemia and the NCI guidelines on acute myeloid leukemia treatment (see, e.g., http://www-.cancer.gov/cancertopics/pdq/treatment/adultAML/Health-Professional/page7).

The term "second line cancer therapy" refers to a cancer treatment that is administered to a subject who does not respond to first line therapy, that is, often first line therapy is administered or who has a recurrence of cancer after being in remission. In certain embodiments, second line therapy that may be administered includes a repeat of the initial successful cancer therapy, which may be any of the treatments described under "first line cancer therapy". In certain embodiments, second line therapy is the administration of gemtuzumab ozogamicin. In certain embodiments, investigational drugs may also be administered as second line therapy in a clinical trial setting. A summary of the currently accepted approaches to second line treatment is described in the NCCN Clinical Practice Guidelines in Oncology for acute myeloid leukemia and the NCI guidelines on acute myeloid leukemia treatment (see, e.g., http://www.cancer-.gov/cancertopics/pdq/treatment/adultAML/HealthProfessional/page5).

The term "refractory" refers to wherein a subject fails to respond or is otherwise resistant to cancer therapy or treatment. The cancer therapy may be first-line, second-line or any subsequently administered treatment. In certain embodiments, refractory refers to a condition where a subject fails to achieve complete remission after two induction attempts. A subject may be refractory due to a cancer cell's intrinsic resistance to a particular therapy, or the subject may be refractory due to an acquired resistance that develops during the course of a particular therapy.

In addition, abbreviations as used herein have respective meanings as follows:

| AML | Acute myeloid leukemia |
| DEAE | Diethylaminoethyl |

-continued

| DMEM | Dulbecco's Modified Eagle's Medium |
| DMF | Dimethylformamide |
| DMSO | Dimethylsulfoxide |
| EGTA | ethylene glycol-bis(β-aminoethyl ether)-N,N,N',N'-tetraacetic acid |
| equiv. | equivalents |
| FBS | Fetal bovine serum |
| FRET | Fluorescence Resonance Energy Transfer |
| HBTU | N,N,N',N'-Tetramethyl-O-(1H-benzotriazol-1-yl)uronium hexafluorophosphate |
| HEPES | 4-(2-hydroxyethyl)-1-piperazineethanesulfonic acid |
| HPLC | High performance liquid chromatography |
| LC/MS | (tandem) liquid chromatography-mass spectrometry |
| MEM | Minimum essential medium |
| Me | Methyl |
| MTBE | Methyl tert-butyl ether |
| PBS | Phosphate buffered saline |
| Ph | Phenyl |
| THF | Tetrahydrofuran |

II. Compounds

Embodiment 1 of this disclosure relates to a compound of Formula I:

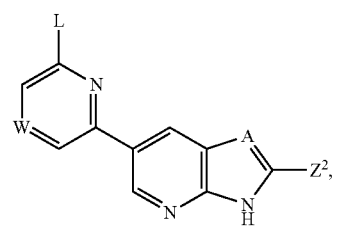

or a pharmaceutically acceptable salt, a solvate, a tautomer, an isomer, or a deuterated analog thereof, wherein:
A is N or —C(Z³)═;
W is —C(R²)═ or N;
Z³ is hydrogen or halo;
Z² is:

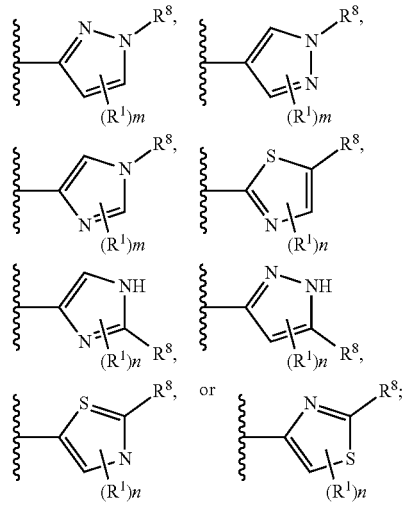

L is —SO$_2$—NR$^6$R$^7$, —NHC(O)R$^4$, or —C(O)NR$^3$R$^4$;
R$^1$ is C$_{1-6}$alkyl, halo, or halo-C$_{1-6}$alkyl;
R$^2$ is hydrogen, —CH$_3$, —CH$_2$F, —CHF$_2$, —CF$_3$, or halo;
R$^3$ is hydrogen or C$_{1-6}$alkyl;
R$^4$ is C$_{1-6}$cycloalkyl, C$_{1-6}$cycloalkyl-C$_{1-3}$alkylene, cyano-C$_{3-6}$ cycloalkyl, cyano-C$_{1-6}$ cycloalkyl-C$_{1-3}$alkyl, cyano-C$_{1-6}$alkylene, heterocycloalkyl, heteroaryl, or —(CH$_2$)—[(CR$^{10}$)]$_2$—OH, wherein the C$_{1-6}$cycloalkyl, C$_{1-6}$cycloalkyl-C$_{1-3}$alkylene, cyano-C$_{3-6}$ cycloalkyl, cyano-C$_{1-6}$ cycloalkyl-C$_{1-3}$alkyl, cyano-C$_{1-6}$alkylene, heterocycloalkyl, and heteroaryl are optionally substituted with 1-2 G groups;
or R$^3$ and R$^4$, together with the N atom to which they are attached, join to form a 4-6 membered heterocycloalkyl moiety substituted with 1-2 G groups;
R$^6$ is hydrogen, C$_{1-6}$alkyl, cyano-C$_{1-6}$alkylene optionally substituted with 1-2 G groups, or C$_{3-6}$cycloalkyl optionally substituted with 1-2 G$^2$ groups;
R$^7$ is hydrogen or C$_{1-6}$alkyl;
or R$^6$ and R$^7$, together with the N atom to which they are attached, join to form a heterocycloalkyl moiety substituted with 1-2 G groups;
R$^8$ is C$_{1-3}$alkyl, hydroxy-C$_{1-6}$alkyl, halo-C$_{1-6}$alkyl, cyano-C$_{1-6}$alkylene, —[C(R$^9$)$_2$]$_{1-2}$—C$_{3-6}$cycloalkyl, —[C(R$^9$)$_2$]$_{1-2}$-heterocycloalkyl, —[C(R$^9$)$_2$]$_{1-2}$-heteroaryl, —[C(R$^9$)$_2$]$_{1-2}$—SO$_2$—C$_{1-3}$alkyl, —[C(R$^9$)$_2$]$_{1-2}$—C(O)—C$_{1-3}$alkyl, —[C(R$^9$)$_2$]$_{1-2}$—C(O)—N(C$_{1-3}$alkyl)$_2$, —[C(R$^9$)$_2$]$_{1-2}$—C(O)—NH$_2$, —[C(R$^9$)$_2$]$_{1-2}$—C(O)—C$_{3-6}$cycloalkyl, or —[C(R$^9$)$_2$]$_{1-2}$—C(O)-heterocycloalkyl;
each R$^9$ is independently selected from hydrogen, C$_{1-6}$alkyl, C$_{3-6}$cycloalkyl, halo, and halo-C$_{1-6}$alkyl;
each R$^{10}$ is C$_{1-3}$alkyl or two R$^{10}$, together with the C atom to which they are attached, join to form a C$_{3-6}$ cycloalkyl;
each G is independently hydroxyl, C$_{1-6}$alkyl, C$_{3-6}$ cycloalkyl, or heterocycloalkyl;
each G$^2$ is independently C$_{1-6}$alkyl, halogen, or cyano,
m is 0-2; and
n is 0-1;
provided that the compound is not
N-(2-cyano-2-methyl-propyl)-6-[2-[1-(2,2,2-trifluoroethyl)pyrazol-4-yl]-1H-pyrrolo[2,3-b]pyridin-5-yl]pyridine-2-carboxamide,
N-(2-cyano-2-methyl-propyl)-6-[2-[1-(difluoromethyl)pyrazol-4-yl]-1H-pyrrolo[2,3-b]pyridin-5-yl]pyridine-2-carboxamide,
N-(1-cyano-1-methyl-ethyl)-6-[2-[1-(difluoromethyl)pyrazol-4-yl]-1H-pyrrolo[2,3-b]pyridin-5-yl]pyridine-2-carboxamide,
N-(1-cyano-1-methyl-ethyl)-6-[2-(2-isopropyl-4-methyl-thiazol-5-yl)-1H-pyrrolo[2,3-b]pyridin-5-yl]pyridine-2-carboxamide,
6-[2-[1-(2-cyanoethyl)pyrazol-4-yl]-1H-pyrrolo[2,3-b]pyridin-5-yl]-N-(1-cyano-1-methyl-ethyl)pyridine-2-carboxamide,
N-(1-cyano-1-methyl-ethyl)-6-[2-[1-(2-morpholinoethyl)pyrazol-4-yl]-1H-pyrrolo[2,3-b]pyridin-5-yl]pyridine-2-carboxamide,
N-(1-cyano-1-methyl-ethyl)-6-[2-(1-isopropyl-3-methyl-pyrazol-4-yl)-1H-pyrrolo[2,3-b]pyridin-5-yl]pyridine-2-carboxamide,
6-[3-chloro-2-[1-(difluoromethyl)pyrazol-4-yl]-1H-pyrrolo[2,3-b]pyridin-5-yl]-N-(1-cyano-1-methyl-ethyl)pyridine-2-carboxamide,
6-[3-chloro-2-(1-isopropyl-3-methyl-pyrazol-4-yl)-1H-pyrrolo[2,3-b]pyridin-5-yl]-N-(1-cyano-1-methyl-ethyl)pyridine-2-carboxamide,
N-(1-cyano-1-methyl-ethyl)-6-[2-[1-(2,2,2-trifluoroethyl)pyrazol-4-yl]-1H-pyrrolo[2,3-b]pyridin-5-yl]pyridine-2-carboxamide,
N-(2-cyanopropan-2-yl)-6-(2-(1-(2-hydroxy-2-methylpropyl)-1H-pyrazol-4-yl)-1H-pyrrolo[2,3-b]pyridin-5-yl)picolinamide,
N-(2-cyanopropan-2-yl)-6-(2-(1-(2,2-difluoroethyl)-1H-pyrazol-4-yl)-1H-pyrrolo[2,3-b]pyridin-5-yl)picolinamide,
N-(2-cyanopropan-2-yl)-6-(2-(1-(oxetan-3-ylmethyl)-1H-pyrazol-4-yl)-1H-pyrrolo[2,3-b]pyridin-5-yl)picolinamide, and
N-(2-cyanopropan-2-yl)-6-(2-(1-((methylsulfonyl)methyl)-1H-pyrazol-4-yl)-1H-pyrrolo[2,3-b]pyridin-5-yl)picolinamide.

Embodiment 1(a) of this disclosure relates to a compound of Formula I:

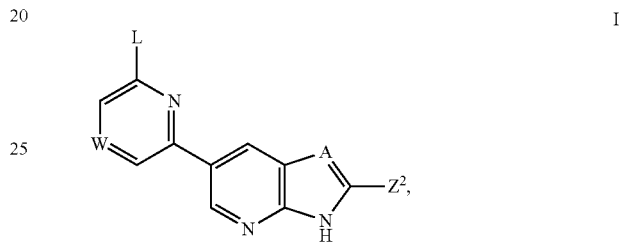

or a pharmaceutically acceptable salt, a solvate, a tautomer, an isomer, or a deuterated analog thereof, wherein:
A is N or —C(Z$^3$)=;
W is —C(R$^2$)= or N;
Z$^3$ is hydrogen or halo;
Z$^2$ is:

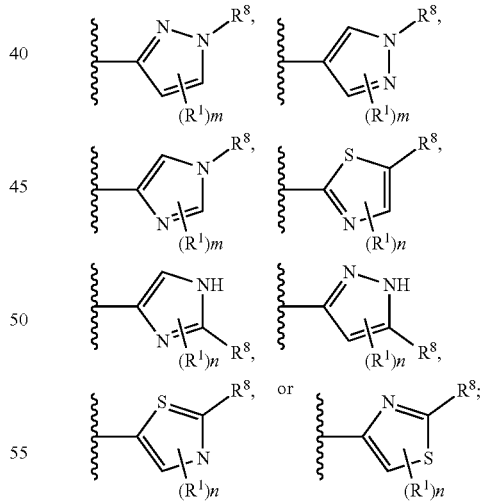

L is —SO$_2$—NR$^6$R$^7$, —NHC(O)R$^4$, or —C(O)NR$^3$R$^4$;
R$^1$ is C$_{1-6}$alkyl, halo, or halo-C$_{1-6}$alkyl;
R$^2$ is hydrogen, —CH$_3$, —CH$_2$F, —CHF$_2$, —CF$_3$, or halo;
R$^3$ is hydrogen or C$_{1-6}$alkyl;
R$^4$ is C$_{3-6}$cycloalkyl, C$_{3-6}$cycloalkyl-C$_{1-3}$alkylene, cyano-C$_{3-6}$ cycloalkyl, cyano-C$_{3-6}$ cycloalkyl-C$_{1-3}$alkyl, cyano-C$_{1-6}$alkylene, heterocycloalkyl, heteroaryl, or —(CH$_2$)—[(CR$^{10}$)]$_2$—OH, wherein the C$_{3-6}$cycloalkyl, $C_{3-6}$cycloalkyl-$C_{1-3}$alkylene, cyano-$C_{3-6}$ cycloalkyl, cyano-$C_{3-6}$ cycloalkyl-$C_{1-3}$alkyl, cyano-$C_{1-6}$alkylene, heterocycloalkyl, and heteroaryl are optionally substituted with 1-2 G groups;

or $R^3$ and $R^4$, together with the N atom to which they are attached, join to form a 4-6 membered heterocycloalkyl moiety substituted with 1-2 G groups;

$R^6$ is hydrogen, $C_{1-6}$alkyl, cyano-$C_{1-6}$alkylene optionally substituted with 1-2 G groups, or $C_{3-6}$cycloalkyl optionally substituted with 1-2 $G^2$ groups;

$R^7$ is hydrogen or $C_{1-6}$alkyl;

or $R^6$ and $R^7$, together with the N atom to which they are attached, join to form a heterocycloalkyl moiety substituted with 1-2 G groups;

$R^8$ is $C_{1-3}$alkyl, hydroxy-$C_{1-6}$alkyl, halo-$C_{1-6}$alkyl, cyano-$C_{1-6}$alkylene, —[C($R^9$)$_2$]$_{1-2}$—$C_{3-6}$cycloalkyl, —[C($R^9$)$_2$]$_{1-2}$-heterocycloalkyl, —[C($R^9$)$_2$]$_{1-2}$-heteroaryl, —[C($R^9$)$_2$]$_{1-2}$—SO$_2$—$C_{1-3}$alkyl, —[C($R^9$)$_2$]$_{1-2}$—C(O)—$C_{1-3}$alkyl, —[C($R^9$)$_2$]$_{1-2}$—C(O)—N($C_{1-3}$alkyl)$_2$, —[C($R^9$)$_2$]$_{1-2}$—C(O)—NH$_2$, —[C($R^9$)$_2$]$_{1-2}$—C(O)—$C_{3-6}$cycloalkyl, or —[C($R^9$)$_2$]$_{1-2}$—C(O)-heterocycloalkyl;

each $R^9$ is independently selected from hydrogen, $C_{1-6}$alkyl, $C_{3-6}$cycloalkyl, halo, and halo-$C_{1-6}$alkyl;

each $R^{10}$ is $C_{1-3}$alkyl or two $R^{10}$, together with the C atom to which they are attached, join to form a $C_{3-6}$ cycloalkyl;

each G is independently hydroxyl, $C_{1-6}$alkyl, $C_{3-6}$ cycloalkyl, or heterocycloalkyl;

each $G^2$ is independently $C_{1-6}$alkyl, halogen, or cyano, m is 0-2; and n is 0-1;

provided that the compound is not

N-(2-cyano-2-methyl-propyl)-6-[2-[1-(2,2,2-trifluoroethyl)pyrazol-4-yl]-1H-pyrrolo[2,3-b]pyridin-5-yl]pyridine-2-carboxamide, N-(2-cyano-2-methyl-propyl)-6-[2-[1-(difluoromethyl)pyrazol-4-yl]-1H-pyrrolo[2,3-b]pyridin-5-yl]pyridine-2-carboxamide, N-(1-cyano-1-methyl-ethyl)-6-[2-[1-(difluoromethyl)pyrazol-4-yl]-1H-pyrrolo[2,3-b]pyridin-5-yl]pyridine-2-carboxamide, N-(1-cyano-1-methyl-ethyl)-6-[2-(2-isopropyl-4-methyl-thiazol-5-yl)-1H-pyrrolo[2,3-b]pyridin-5-yl]pyridine-2-carboxamide, 6-[2-[1-(2-cyanoethyl)pyrazol-4-yl]-1H-pyrrolo[2,3-b]pyridin-5-yl]-N-(1-cyano-1-methyl-ethyl)pyridine-2-carboxamide, N-(1-cyano-1-methyl-ethyl)-6-[2-[1-(2-morpholinoethyl)pyrazol-4-yl]-1H-pyrrolo[2,3-b]pyridin-5-yl]pyridine-2-carboxamide, N-(1-cyano-1-methyl-ethyl)-6-[2-(1-isopropyl-3-methyl-pyrazol-4-yl)-1H-pyrrolo[2,3-b]pyridin-5-yl]pyridine-2-carboxamide, 6-[3-chloro-2-[1-(difluoromethyl)pyrazol-4-yl]-1H-pyrrolo[2,3-b]pyridin-5-yl]-N-(1-cyano-1-methyl-ethyl)pyridine-2-carboxamide, 6-[3-chloro-2-(1-isopropyl-3-methyl-pyrazol-4-yl)-1H-pyrrolo[2,3-b]pyridin-5-yl]-N-(1-cyano-1-methyl-ethyl)pyridine-2-carboxamide, N-(1-cyano-1-methyl-ethyl)-6-[2-[1-(2,2,2-trifluoroethyl)pyrazol-4-yl]-1H-pyrrolo[2,3-b]pyridin-5-yl]pyridine-2-carboxamide, N-(2-cyanopropan-2-yl)-6-(2-(1-(2-hydroxy-2-methylpropyl)-1H-pyrazol-4-yl)-1H-pyrrolo[2,3-b]pyridin-5-yl)picolinamide, N-(2-cyanopropan-2-yl)-6-(2-(1-(2,2-difluoroethyl)-1H-pyrazol-4-yl)-1H-pyrrolo[2,3-b]pyridin-5-yl)picolinamide, N-(2-cyanopropan-2-yl)-6-(2-(1-(oxetan-3-ylmethyl)-1H-pyrazol-4-yl)-1H-pyrrolo[2,3-b]pyridin-5-yl)picolinamide, and N-(2-cyanopropan-2-yl)-6-(2-(1-((methylsulfonyl)methyl)-1H-pyrazol-4-yl)-1H-pyrrolo[2,3-b]pyridin-5-yl)picolinamide.

Embodiment 1(b) of this disclosure relates to a compound of Formula I:

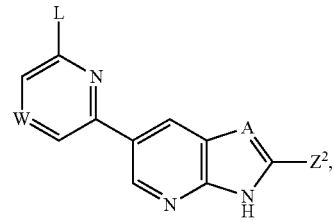

or a pharmaceutically acceptable salt, a solvate, a tautomer, an isomer, or a deuterated analog thereof, wherein:

A is N or —C($Z^3$)=;

W is —C($R^2$)= or N;

$Z^3$ is hydrogen or halo;

$Z^2$ is:

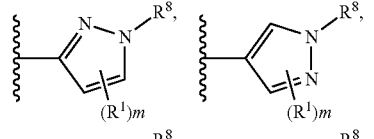

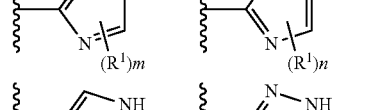

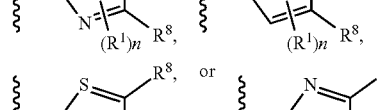

L is —SO$_2$—NR$^6$R$^7$, —NHC(O)R$^4$, or —C(O)NR$^3$R$^4$;

$R^1$ is $C_{1-6}$alkyl, halo, or halo-$C_{1-6}$alkyl;

$R^2$ is hydrogen, —CH$_3$, —CH$_2$F, —CHF$_2$, —CF$_3$, or halo;

$R^3$ is hydrogen or $C_{1-6}$alkyl;

$R^4$ is $C_{1-6}$cycloalkyl, $C_{1-6}$cycloalkyl-$C_{1-3}$alkylene, cyano-$C_{3-6}$ cycloalkyl, cyano-$C_{1-6}$ cycloalkyl-$C_{1-3}$alkyl, cyano-$C_{1-6}$alkylene, heterocycloalkyl, heteroaryl, or —(CH$_2$)—[(CR$^{10}$)]$_2$—OH, wherein the $C_{1-6}$cycloalkyl, $C_{1-6}$cycloalkyl-$C_{1-3}$alkylene, cyano-$C_{3-6}$ cycloalkyl, cyano-$C_{1-6}$ cycloalkyl-$C_{1-3}$alkyl, cyano-$C_{1-6}$alkylene, heterocycloalkyl, and heteroaryl are optionally substituted with 1-2 G groups;

or $R^3$ and $R^4$, together with the N atom to which they are attached, join to form a 4-6 membered heterocycloalkyl moiety substituted with 1-2 G groups;

$R^6$ is hydrogen, $C_{1-6}$alkyl, cyano-$C_{1-6}$alkylene optionally substituted with 1-2 G groups, or $C_{3-6}$cycloalkyl optionally substituted with 1-2 $G^2$ groups;

$R^7$ is hydrogen or $C_{1-6}$alkyl;

or $R^6$ and $R^7$, together with the N atom to which they are attached, join to form a heterocycloalkyl moiety substituted with 1-2 G groups;

$R^8$ is $C_{1-3}$alkyl, hydroxy-$C_{1-6}$alkyl, halo-$C_{1-6}$alkyl, cyano-$C_{1-6}$alkylene, —[C($R^9$)$_2$]$_{1-2}$—$C_{3-6}$cycloalkyl, —[C($R^9$)$_2$]$_{1-2}$-heterocycloalkyl, —[C($R^9$)$_2$]$_{1-2}$-heteroaryl, —[C($R^9$)$_2$]$_{1-2}$—SO$_2$—$C_{1-3}$alkyl, —[C($R^9$)$_2$]$_{1-2}$—C(O)—$C_{1-3}$alkyl, —[C($R^9$)$_2$]$_{1-2}$—C(O)—N($C_{1-3}$alkyl)$_2$, —[C($R^9$)$_2$]$_{1-2}$—C(O)—NH$_2$, —[C($R^9$)$_2$]$_{1-2}$—C(O)—$C_{3-6}$cycloalkyl, or —[C($R^9$)$_2$]$_{1-2}$—C(O)-heterocycloalkyl;

each $R^9$ is independently selected from hydrogen, $C_{1-6}$alkyl, $C_{3-6}$cycloalkyl, halo, and halo-$C_{1-6}$alkyl;

each $R^{10}$ is $C_{1-3}$alkyl or two $R^{10}$, together with the C atom to which they are attached, join to form a $C_{3-6}$ cycloalkyl;

each G is independently hydroxyl, $C_{1-6}$alkyl, $C_{3-6}$ cycloalkyl, or heterocycloalkyl;

each $G^2$ is independently $C_{1-6}$alkyl, halogen, or cyano;

m is 0-2; and n is 0-1.

Embodiment 2 of this disclosure relates to the compound according to Embodiment 1, 1(a), or 1(b), wherein W is —C($R^2$)=, and $R^2$ is —CH$_3$, F, Cl, or Br.

Embodiment 2(a) of this disclosure relates to the compound according to Embodiment 1, 1(a), or 1(b), wherein W is —C($R^2$)=, and $R^2$ is —CH$_3$.

Embodiment 2(b) of this disclosure relates to the compound according to Embodiment 1, 1(a), or 1(b), wherein W is —C($R^2$)=, and $R^2$ is F, Cl, or Br.

Embodiment 2(c) of this disclosure relates to the compound according to Embodiment 1, 1(a), or 1(b), wherein W is —C($R^2$)=, $R^2$ is —CH$_3$, F, Cl, or Br, and $Z^3$ is halo.

Embodiment 3 of this disclosure relates to the compound according to Embodiment 1, 1(a), or 1(b), wherein W is —C($R^2$)=, and $R^2$ is hydrogen.

Embodiment 4 of this disclosure relates to the compound according to Embodiment 1, 1(a), or 1(b), wherein W is N.

Embodiment 5 of this disclosure relates to the compound according to any one of Embodiments 1-4, wherein A is —C($Z^3$)= and L is —C(O)NR$^3$R$^4$.

Embodiment 5(a) of this disclosure relates to the compound according to any one of Embodiments 1-4, wherein A is —C($Z^3$)=, L is —C(O)NR$^3$R$^4$, $R^3$ is hydrogen or $C_{1-3}$alkyl, and $R^4$ is cyano-$C_{1-6}$alkylene optionally substituted with $C_3$-$C_6$cycloalkyl.

Embodiment 5(b) of this disclosure relates to the compound according to any one of Embodiments 1-4, wherein A is —C($Z^3$)=, L is —C(O)NR$^3$R$^4$, and $R^3$ and $R^4$, together with the N atom to which they are attached, join to form a 4-6 membered heterocycloalkyl moiety substituted with 1-2 G groups.

Embodiment 5(c) of this disclosure relates to the compound according to any one of Embodiments 1-4, wherein A is —C($Z^3$)=, L is —C(O)NR$^3$R$^4$, $R^3$ is hydrogen or $C_{1-3}$alkyl, and $R^4$ is heterocycloalkyl optionally substituted with 1-3 G groups.

Embodiment 5(d) of this disclosure relates to the compound according to any one of Embodiments 1-4, wherein A is —C($Z^3$)=, L is —C(O)NR$^3$R$^4$, $R^3$ is hydrogen or $C_{1-3}$alkyl, and $R^4$ is 1,1-dioxidothietan-3-yl, oxetan-3yl, or 1-methylazetinid-3-yl.

Embodiment 5(e) of this disclosure relates to the compound according to any one of Embodiments 1-4, wherein A is —C($Z^3$)=, L is —C(O)NR$^3$R$^4$, $R^3$ is hydrogen or $C_{1-3}$alkyl, and $R^4$ is cycloalkyl optionally substituted with hydroxyl.

Embodiment 5(f) of this disclosure relates to the compound according to any one of Embodiments 1-4, wherein A is —C($Z^3$)=, L is —C(O)NR$^3$R$^4$, $R^3$ is hydrogen or $C_{1-3}$alkyl, and $R^4$ is heteroaryl.

Embodiment 5(g) of this disclosure relates to the compound according to any one of Embodiments 1-4, wherein A is —C($Z^3$)=, L is —C(O)NR$^3$R$^4$, $R^3$ is hydrogen or $C_{1-3}$alkyl, and $R^4$ is imidazol-2-yl, imidazol-5-yl, pyrazol-5-yl, triazol-3-yl, or tetrazol-5-yl.

Embodiment 5(h) of this disclosure relates to the compound according to any one of Embodiments 1-4, wherein A is —C($Z^3$)=, L is —C(O)NR$^3$R$^4$, $R^3$ is hydrogen or $C_{1-3}$alkyl, and $R^4$ is —(CH$_2$)—[(CR$^{10}$)]$_2$—OH.

Embodiment 5(i) of this disclosure relates to the compound according to any one of Embodiments 1-4, wherein A is —C($Z^3$)=, L is —C(O)NR$^3$R$^4$, $R^3$ is hydrogen or $C_{1-3}$alkyl, $R^4$ is —(CH$_2$)—[(CR$^{10}$)]$_2$—OH, and each $R^{10}$ is methyl.

Embodiment 5(j) of this disclosure relates to the compound according to any one of Embodiments 1-4, wherein A is —C($Z^3$)=, L is —C(O)NR$^3$R$^4$, $R^3$ is hydrogen or $C_{1-3}$alkyl, $R^4$ is —(CH$_2$)—[(CR$^{10}$)]$_2$—OH, and two $R^{10}$, together with the carbon to which they are attached, join to form a $C_{3-4}$ cycloalkyl.

Embodiment 5(k) of this disclosure relates to the compound according to any one of Embodiments 1-4, wherein A is —C($Z^3$)= and L is —SO$_2$—NR$^6$R$^7$.

Embodiment 5(l) of this disclosure relates to the compound according to any one of Embodiments 1-4, wherein A is —C($Z^3$)=, L is —SO$_2$—NR$^6$R$^7$, $R^7$ is hydrogen or $C_{1-3}$alkyl, and $R^6$ is $C_{1-3}$alkyl.

Embodiment 5(m) of this disclosure relates to the compound according to any one of Embodiments 1-4, wherein A is —C($Z^3$)=, L is —SO$_2$—NR$^6$R$^7$, $R^7$ is hydrogen or $C_{1-3}$alkyl, and $R^6$ is cyano-$C_{1-6}$alkylene optionally substituted with $C_3$-$C_6$cycloalkyl.

Embodiment 6 of this disclosure relates to the compound according to any one of Embodiments 1-4, wherein A is —C($Z^3$)=, and L is:

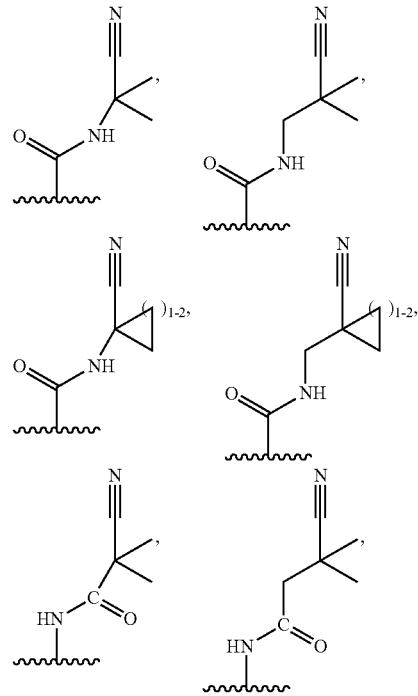

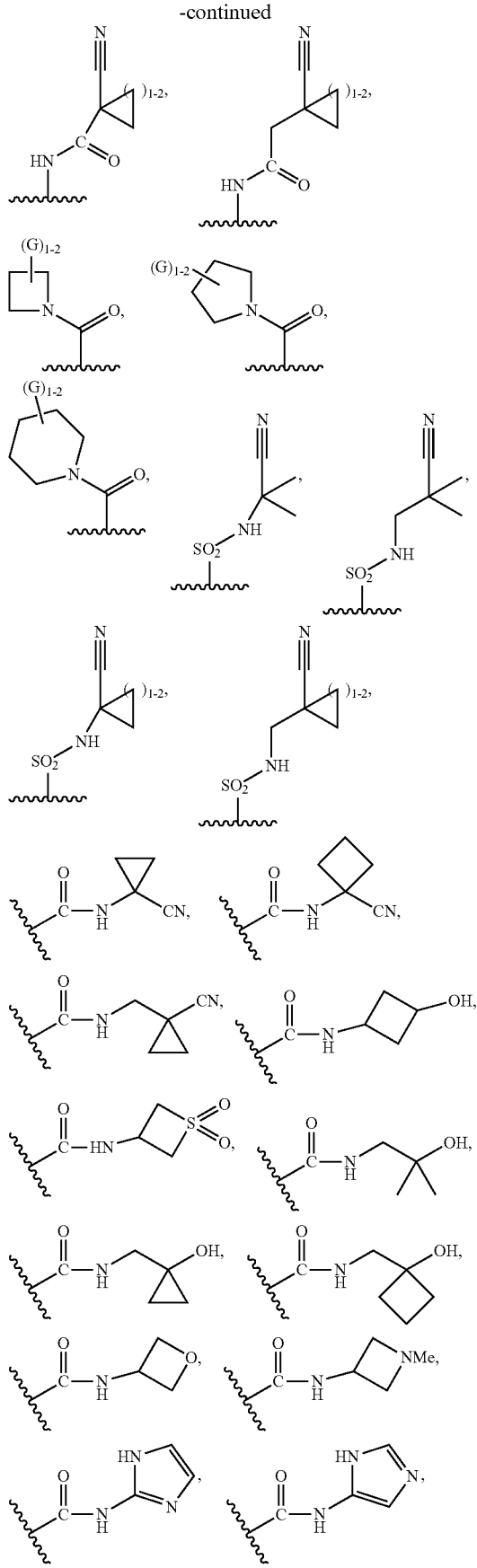
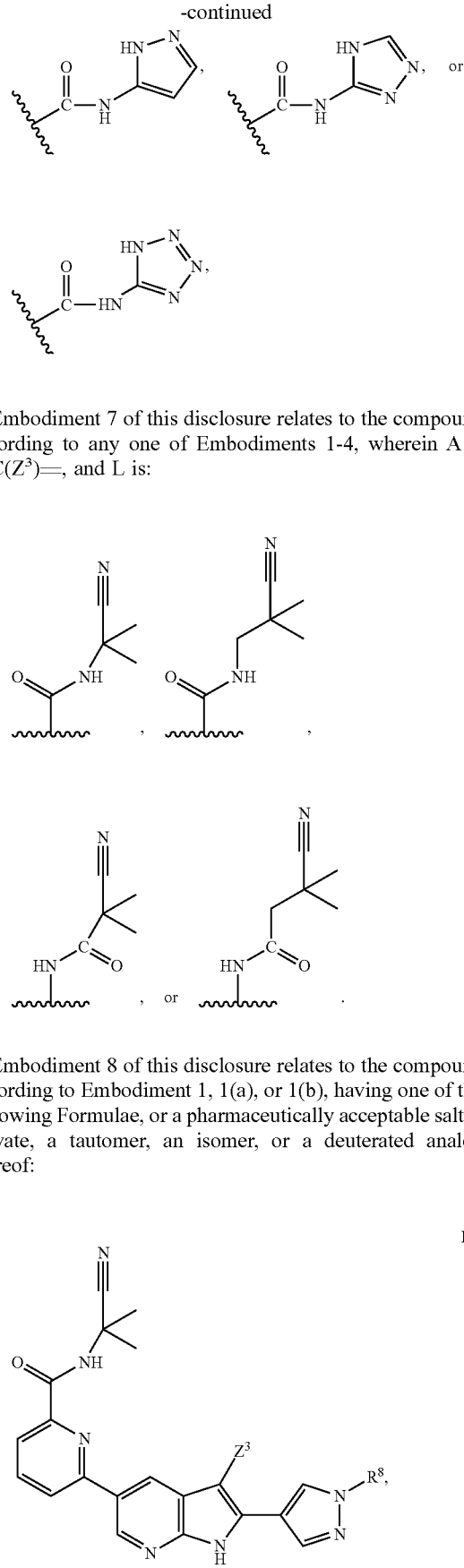
Embodiment 7 of this disclosure relates to the compound according to any one of Embodiments 1-4, wherein A is —C($Z^3$)=, and L is:
Embodiment 8 of this disclosure relates to the compound according to Embodiment 1, 1(a), or 1(b), having one of the following Formulae, or a pharmaceutically acceptable salt, a solvate, a tautomer, an isomer, or a deuterated analog thereof:
I(a)

-continued
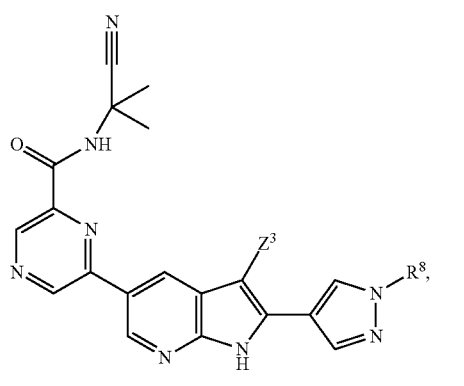
I(b)
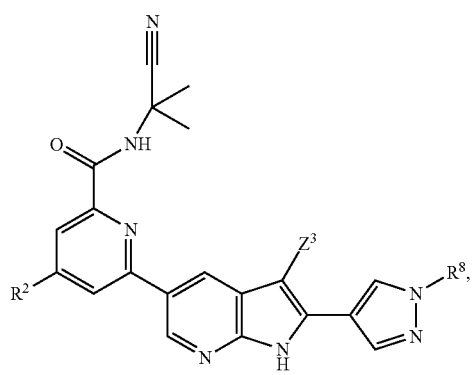
I(c)
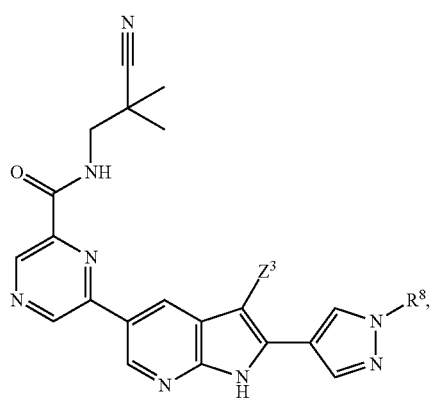
I(d)
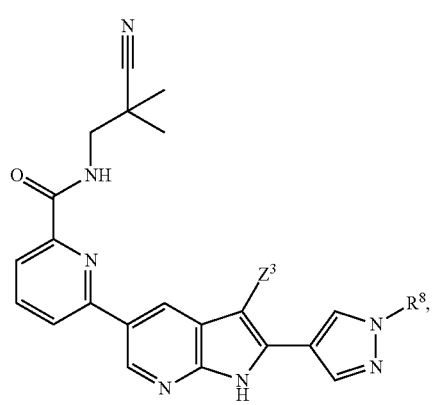
I(e)
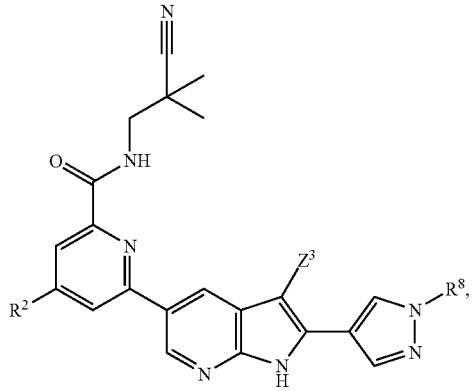
I(f)
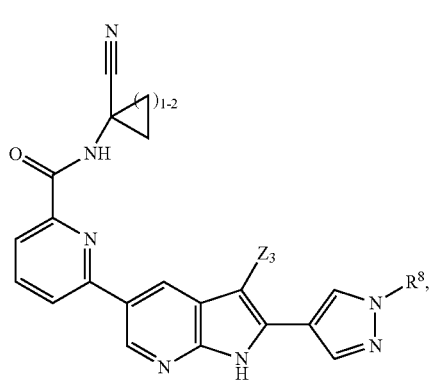
I(g)
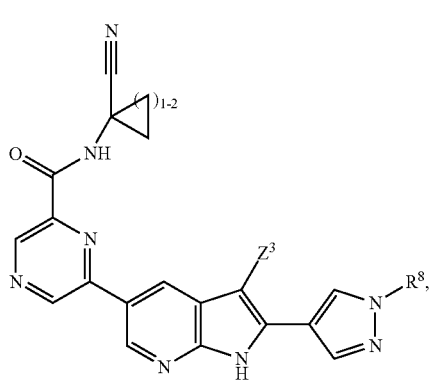
I(h)
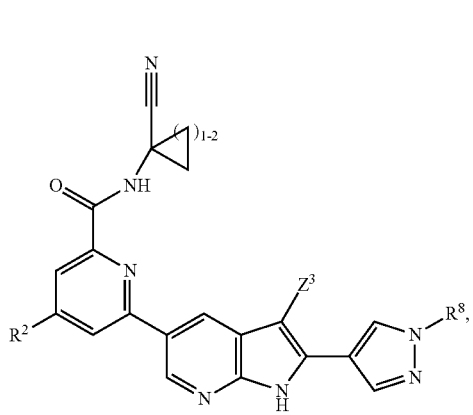
I(i)

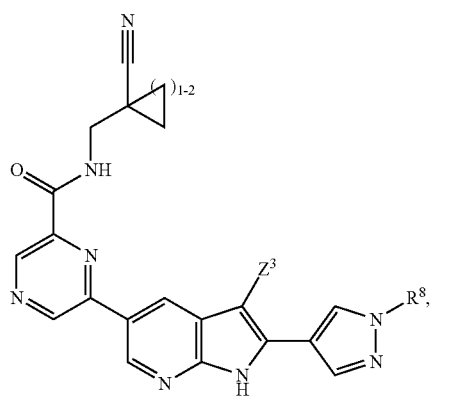
I(j)
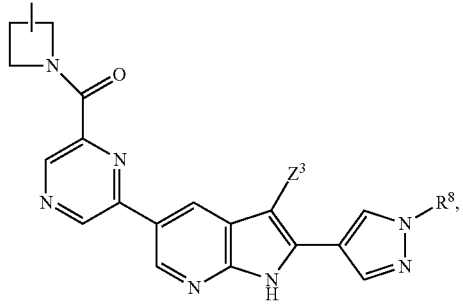
I(n)
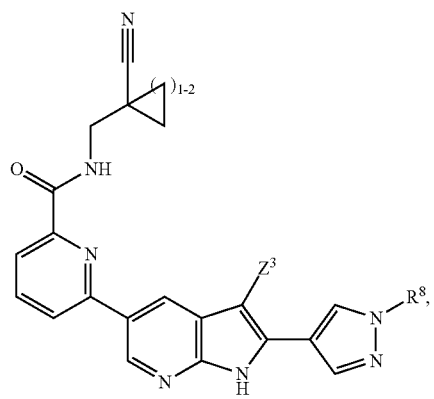
I(k)
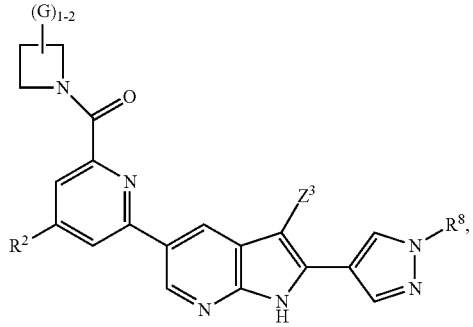
I(o)
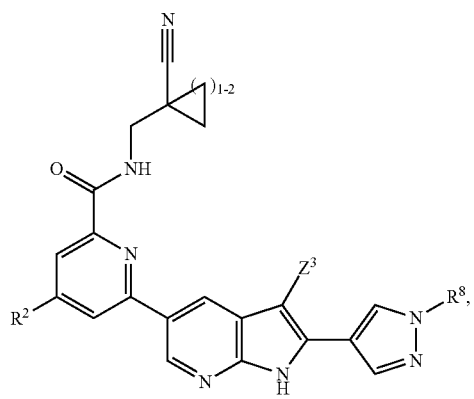
I(l)
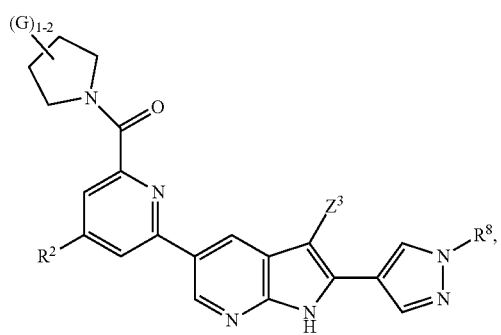
I(q)
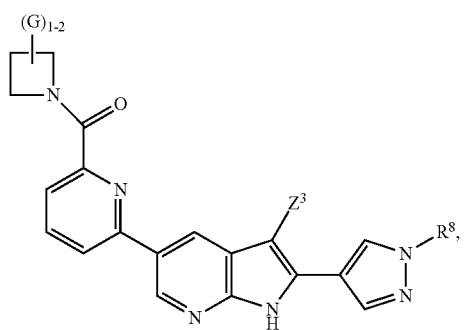
I(m)
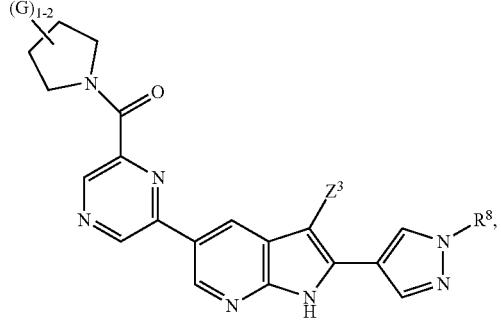
I(r)

I(t)
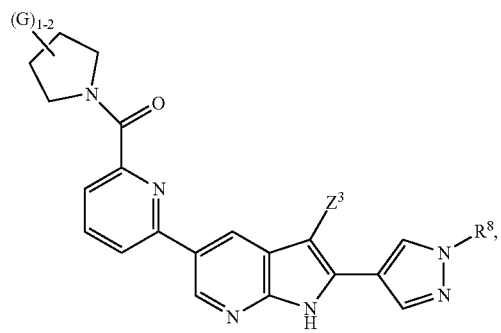
I(u)
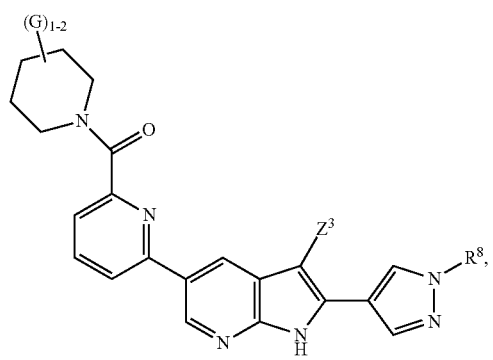
I(v)
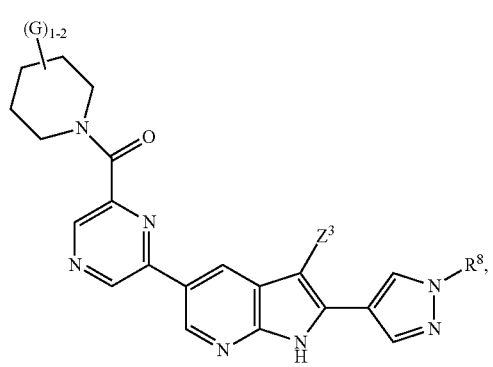
I(w)
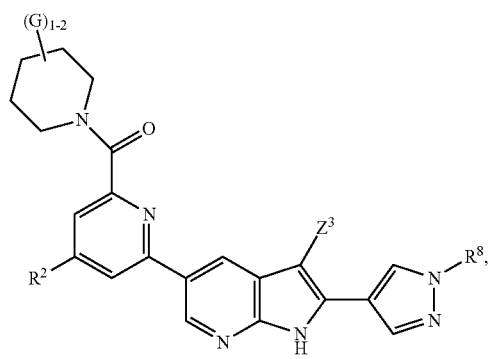
I(x)
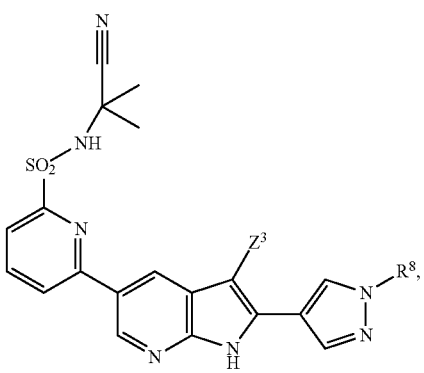
I(y)
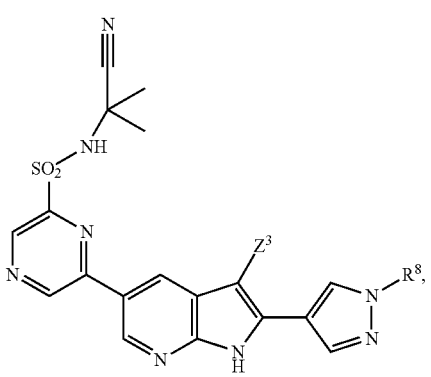
I(z)
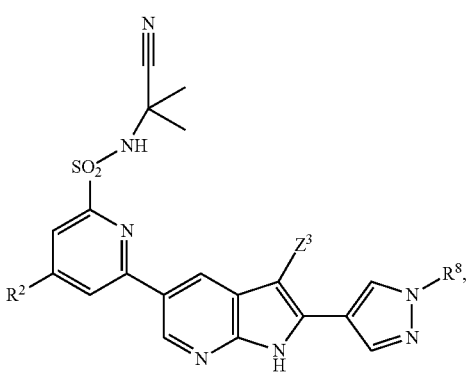
I(aa)
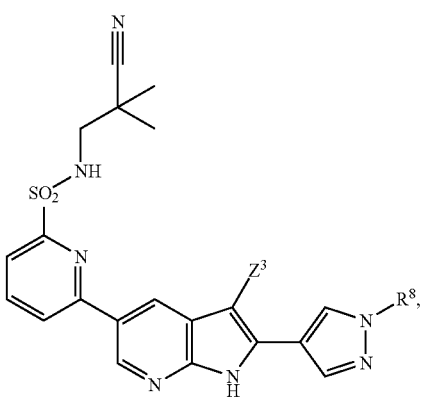

-continued
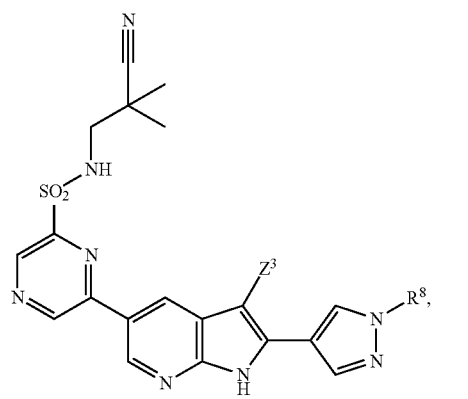
I(bb)
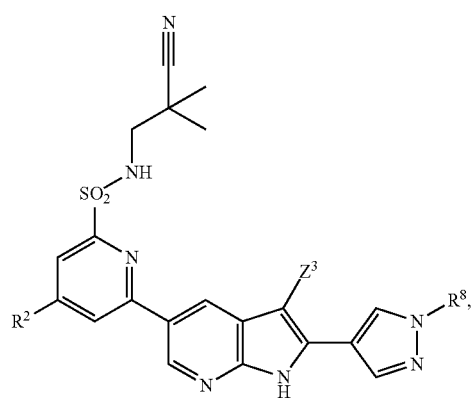
I(cc)
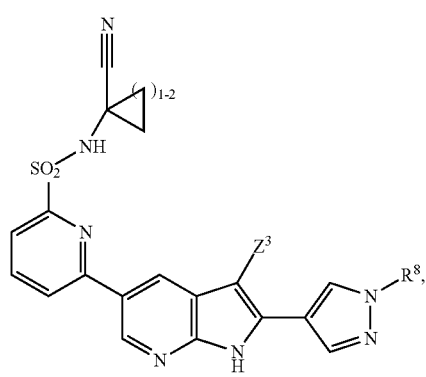
I(dd)
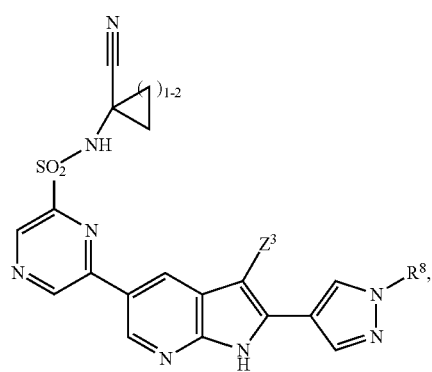
I(ee)
-continued
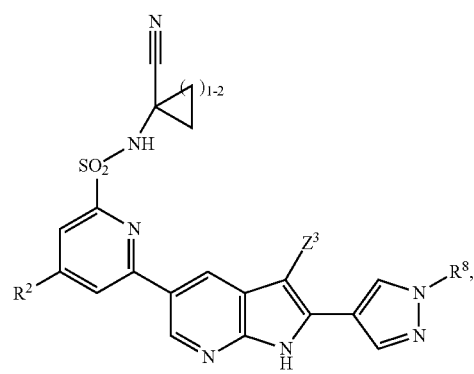
I(ff)
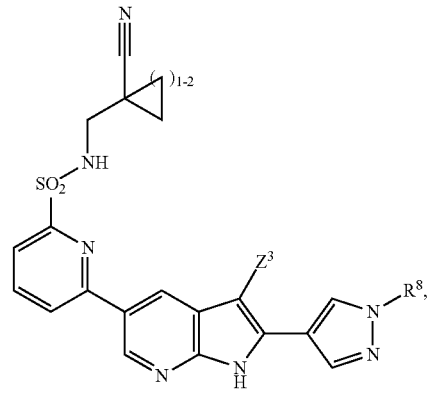
I(gg)
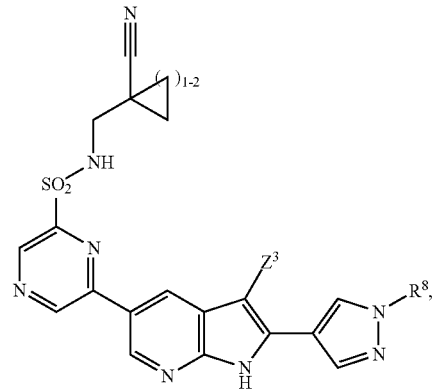
I(hh)
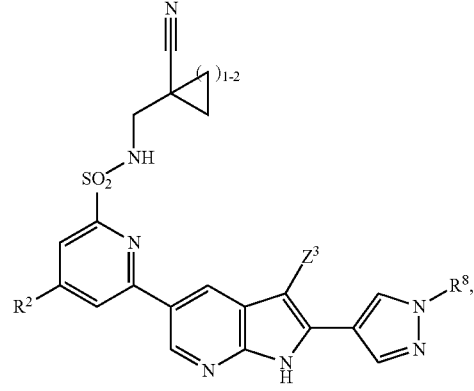
I(ii)

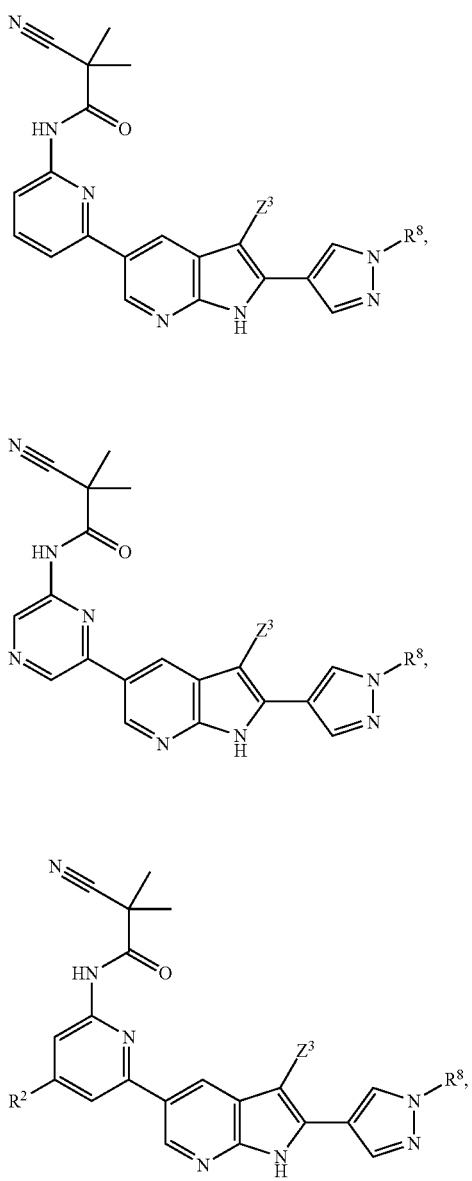

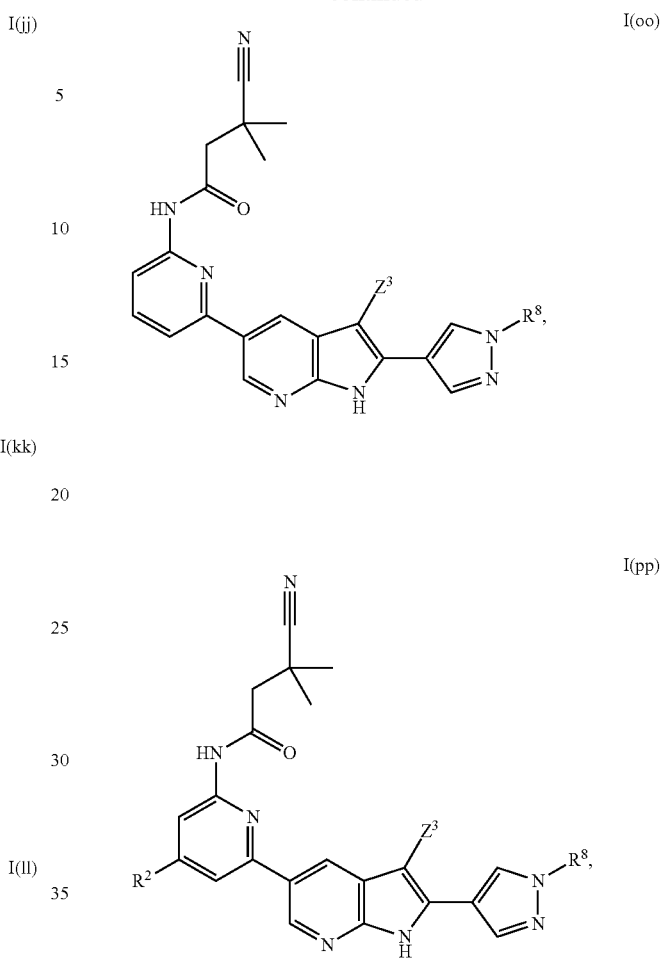

wherein R² is —CH₃, Cl, or F.

Embodiment 8(a) of this disclosure relates to the compound according to Embodiment 8, having one of Formulae I(g), I(h), I(i), I(j), I(k), or I(l).

Embodiment 8(b) of this disclosure relates to the compound according to Embodiment 8, having one of Formulae I(m), I(n), I(o), I(q), I(r), I(t), I(u), I(v), or I(w).

Embodiment 8(c) of this disclosure relates to the compound according to Embodiment 8, having one of Formulae I(x), I(y), I(z), I(aa), I(bb), I(cc), I(dd), I(ee), I(ff), I(gg), I(hh), or I(ii).

Embodiment 8(d) of this disclosure relates to the compound according to Embodiment 8, having one of Formulae I(jj), I(kk), I(ll), I(mm), I(oo), or I(pp).

Embodiment 8(e) of this disclosure relates to the compound according to Embodiment 1, 1(a), or 1(b), having one of the following Formulae, or a pharmaceutically acceptable salt, a solvate, a tautomer, an isomer, or a deuterated analog thereof:

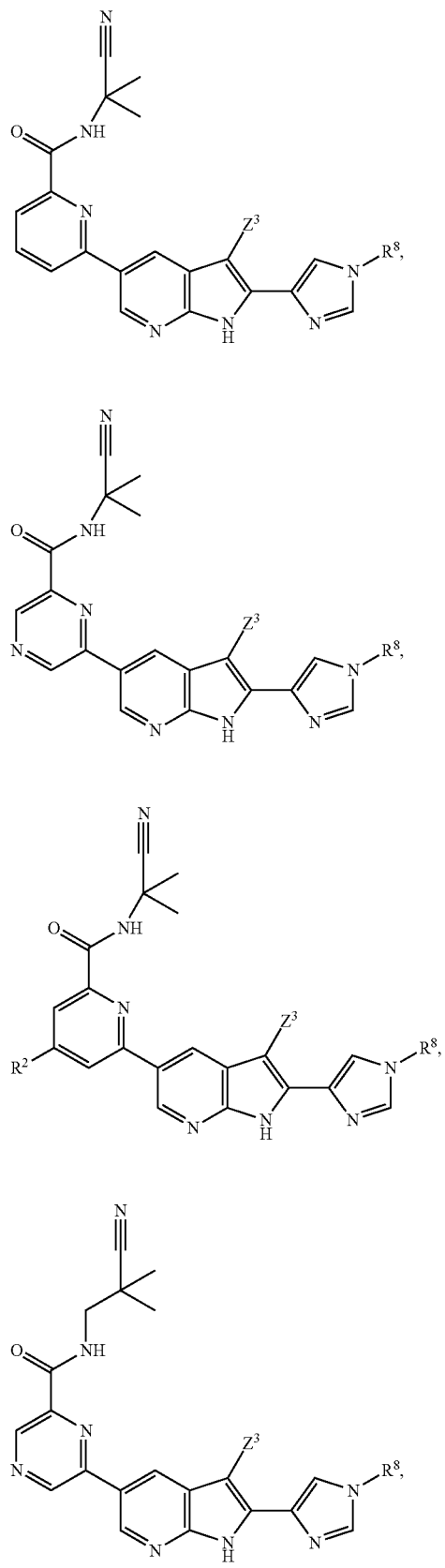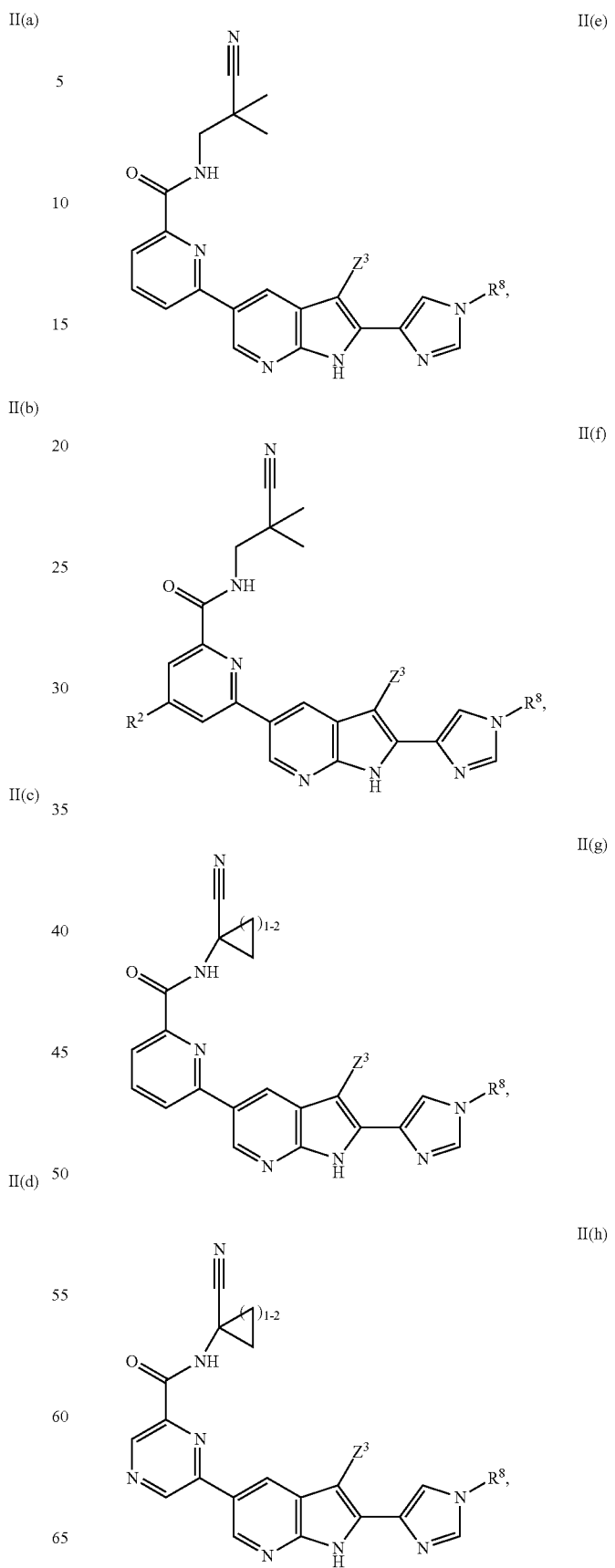

II(i)
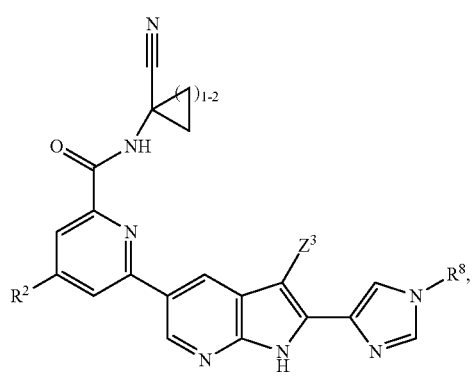
II(j)
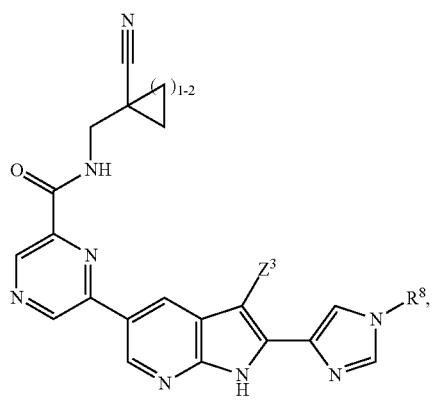
II(k)
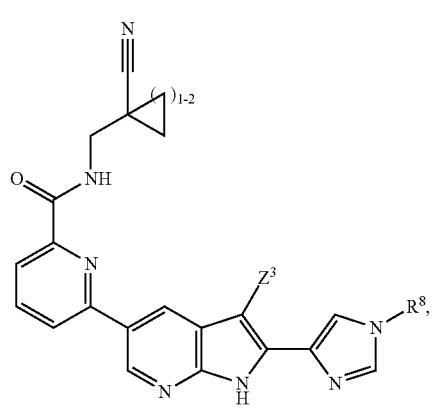
II(l)
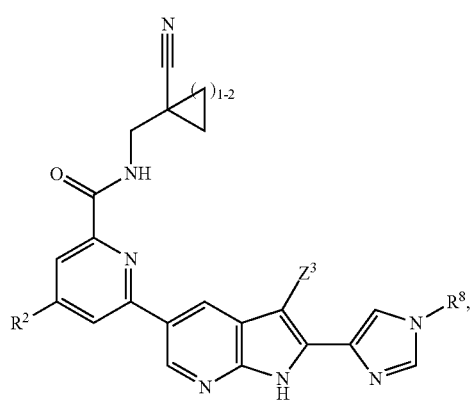
II(m)
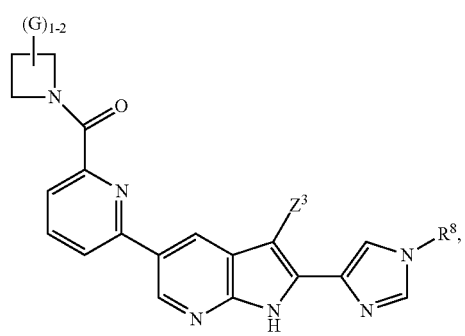
II(n)
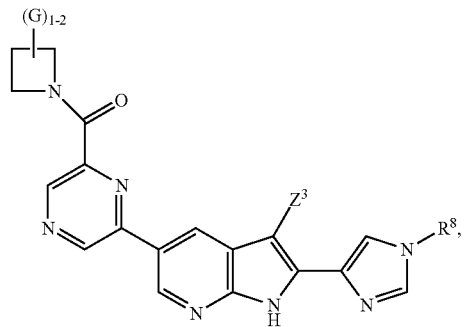
II(o)
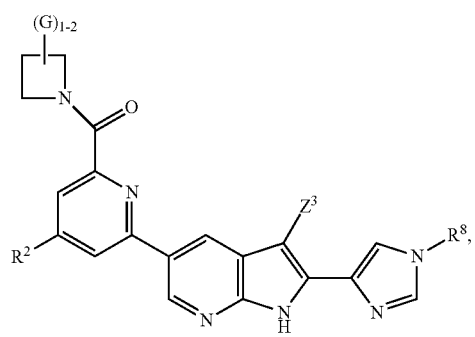
II(q)
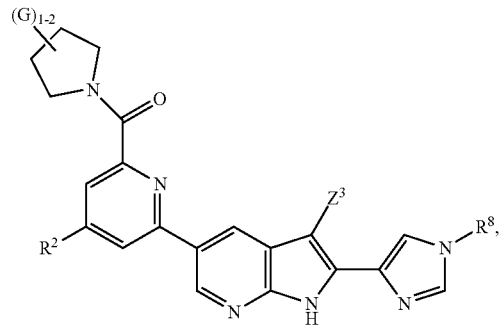

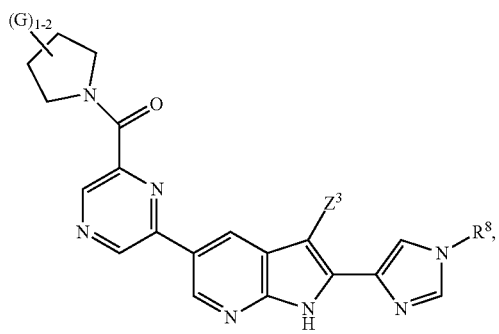
II(r)
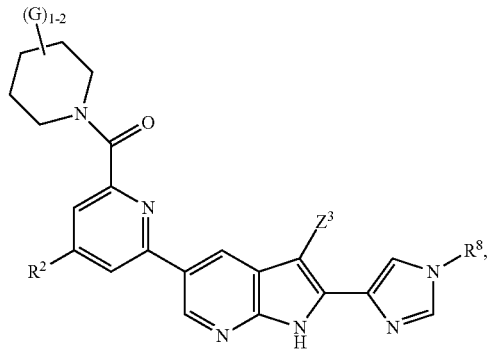
II(w)
II(t)
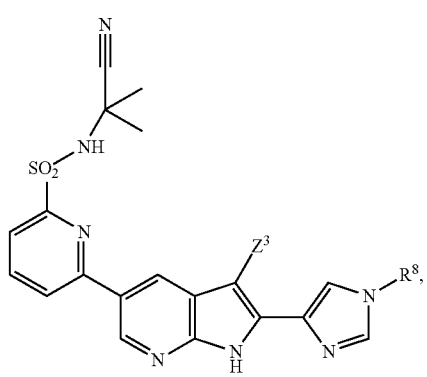
II(x)
II(u)
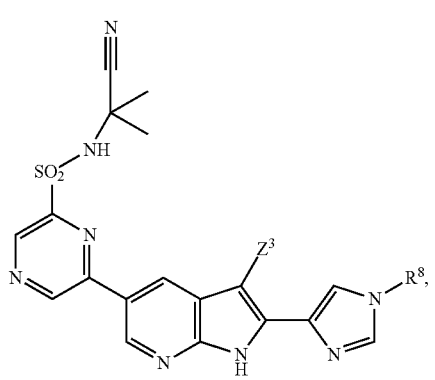
II(y)
II(v)
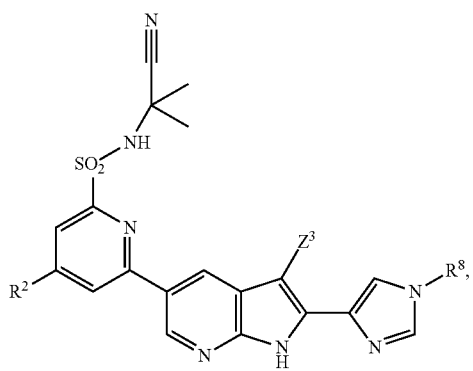
II(z)

II(aa)
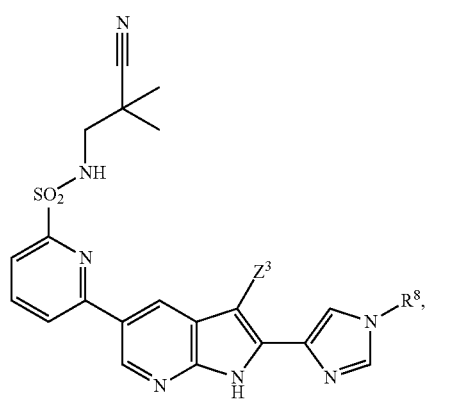
II(bb)
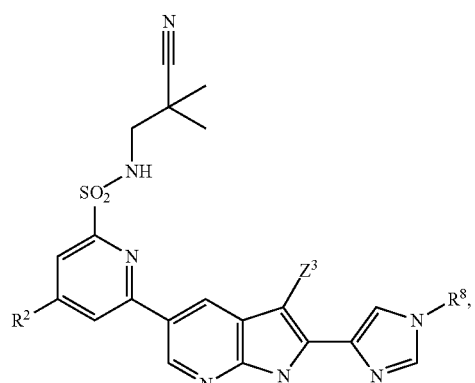
II(cc)
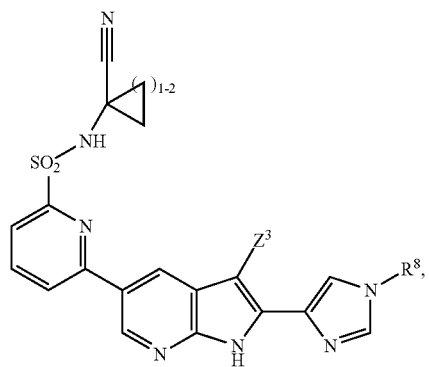
II(dd)
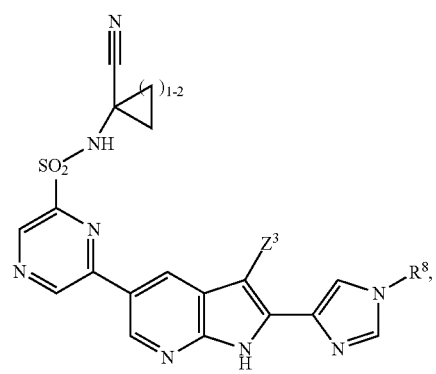
II(ee)
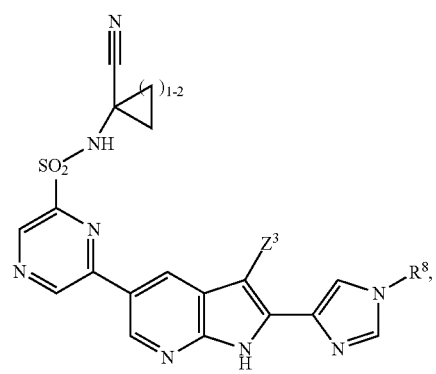
II(ff)
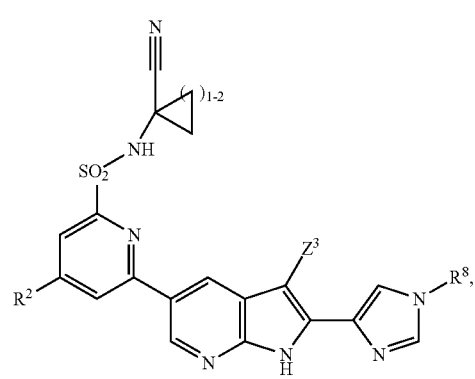
II(gg)
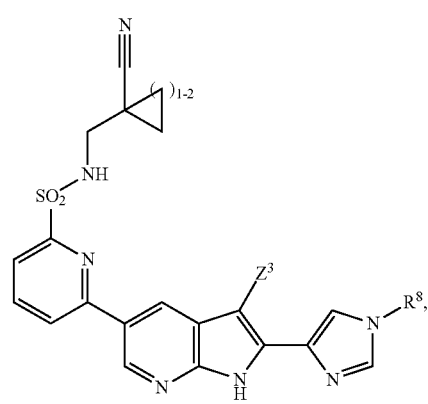
II(hh)
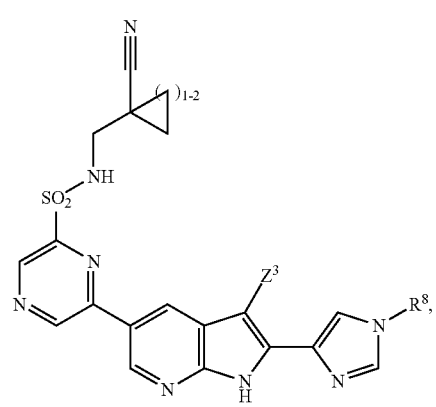

II(ii)
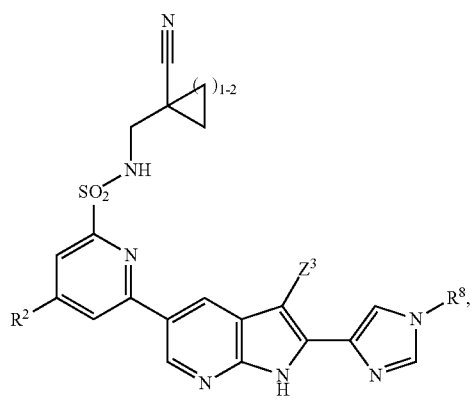
wherein R² is Cl or F.
Embodiment 8(f) of this disclosure relates to the compound according to Embodiment 1, 1(a), or 1(b), having one of the following Formulae, or a pharmaceutically acceptable salt, a solvate, a tautomer, an isomer, or a deuterated analog thereof:
III(a)
[structure]
III(b)
[structure]
III(c)
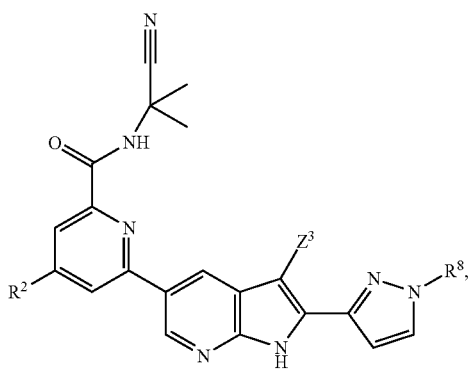
III(d)
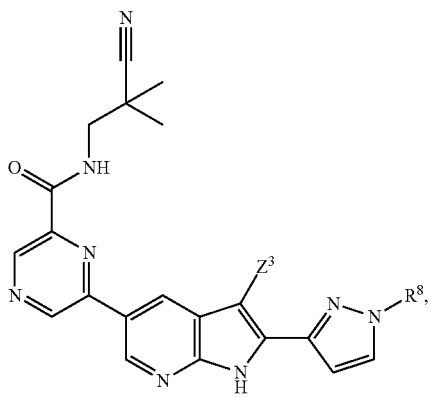
III(e)
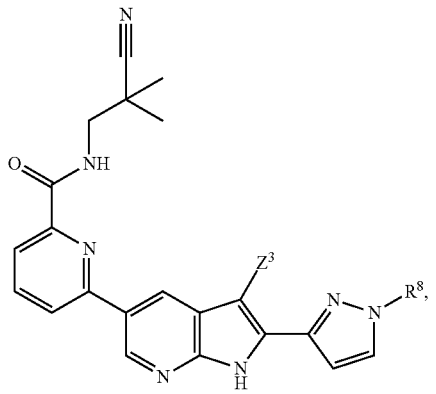
III(f)
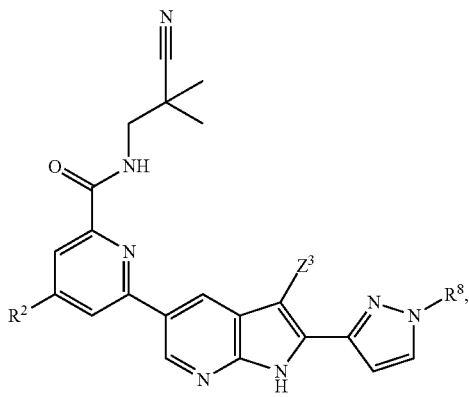

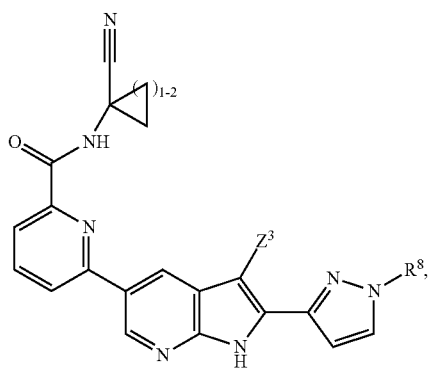
III(g)
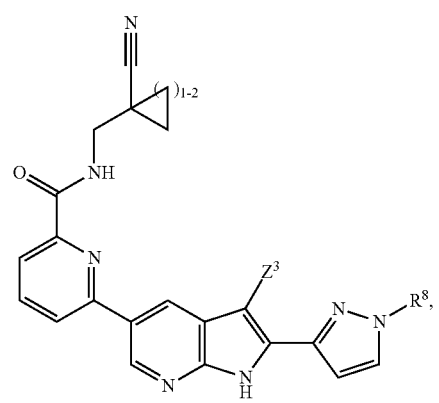
III(k)
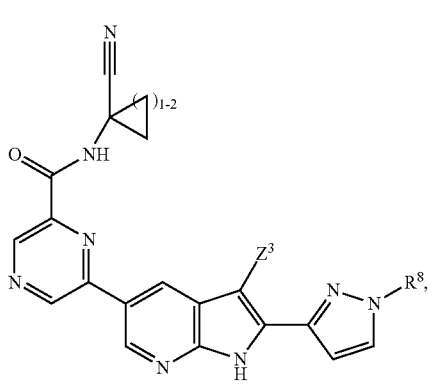
III(h)
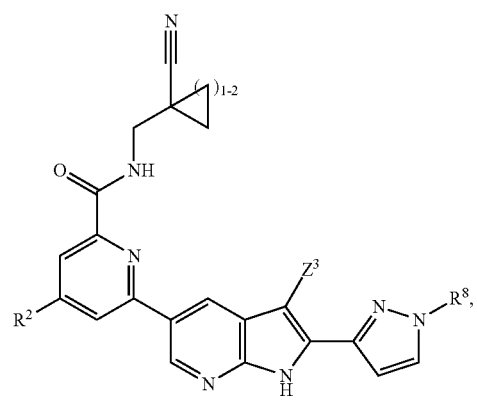
III(l)
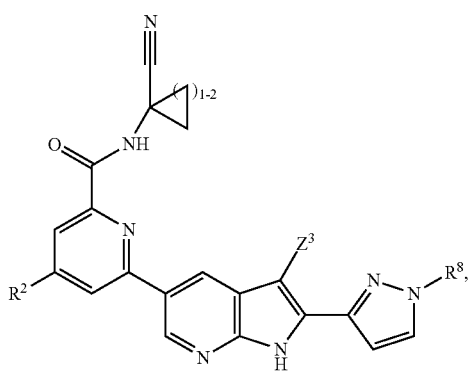
III(i)
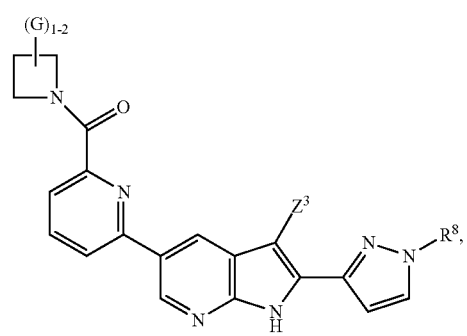
III(m)
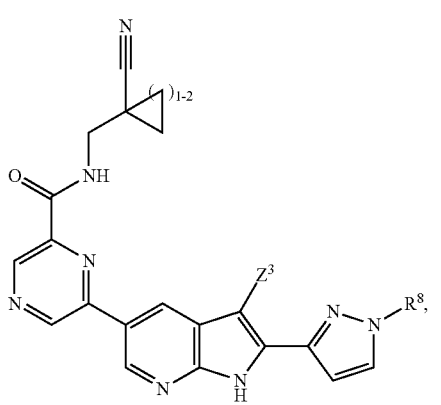
III(j)
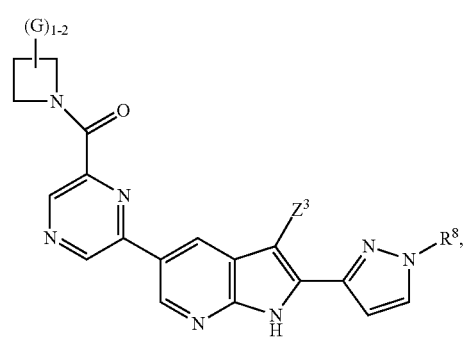
III(n)

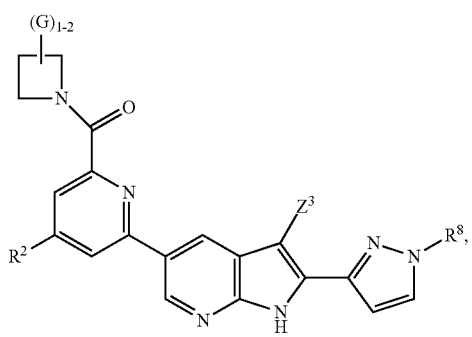
III(o)
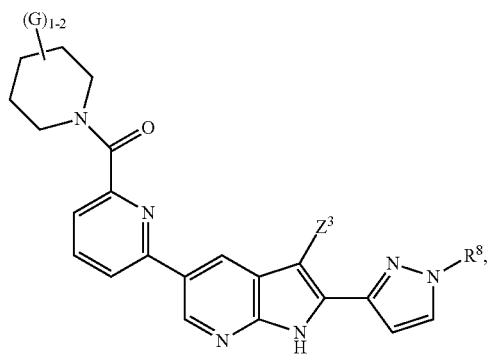
III(u)
III(q)
III(v)
III(r)
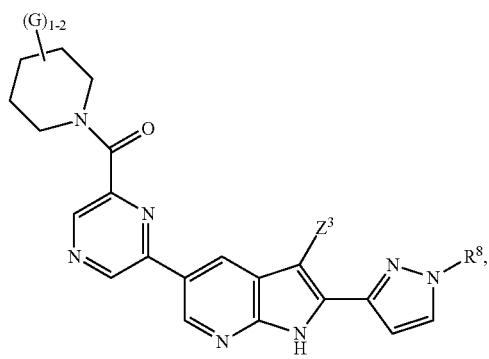
III(w)
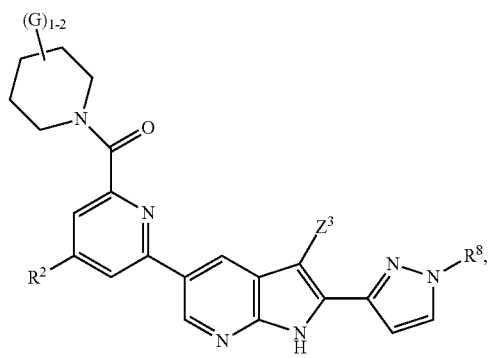
III(x)
III(t)
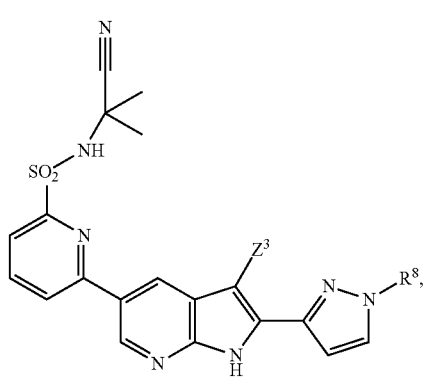

III(y)
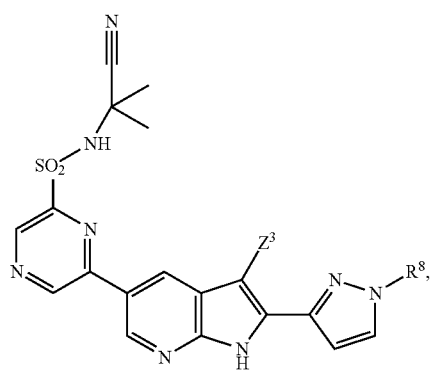
III(z)
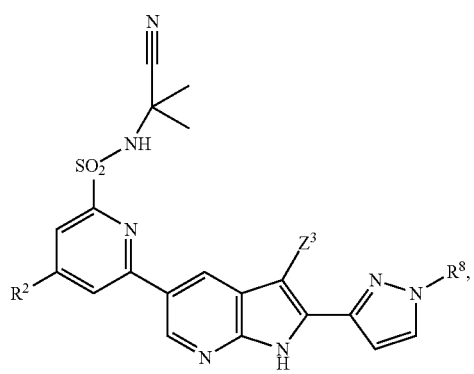
III(aa)
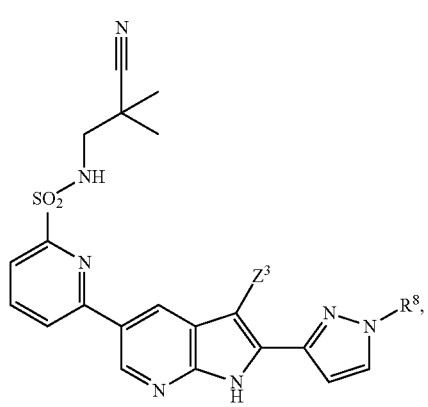
III(bb)
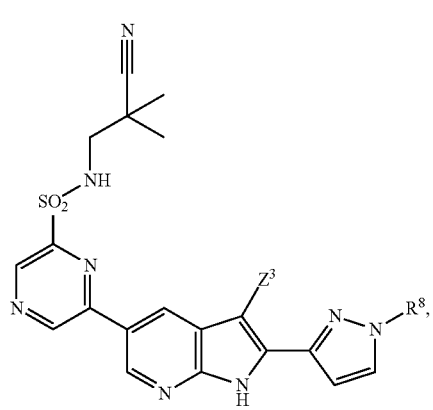
III(cc)
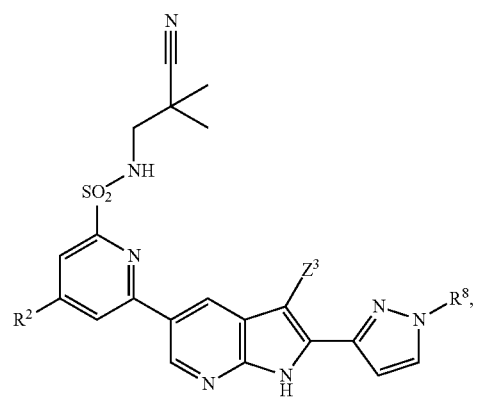
III(dd)
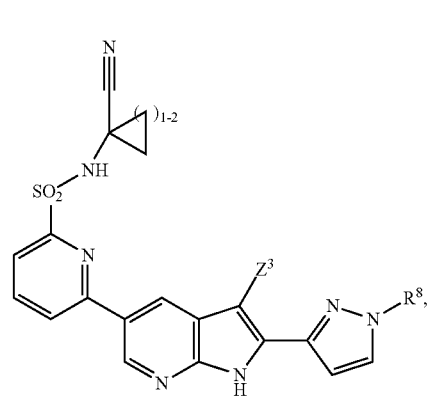
III(ee)
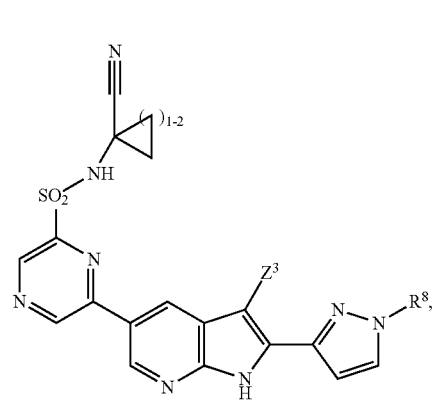
III(ff)
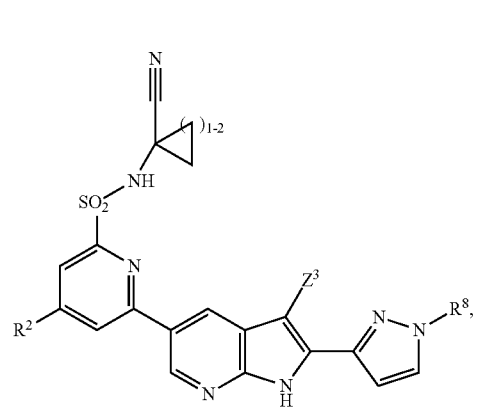

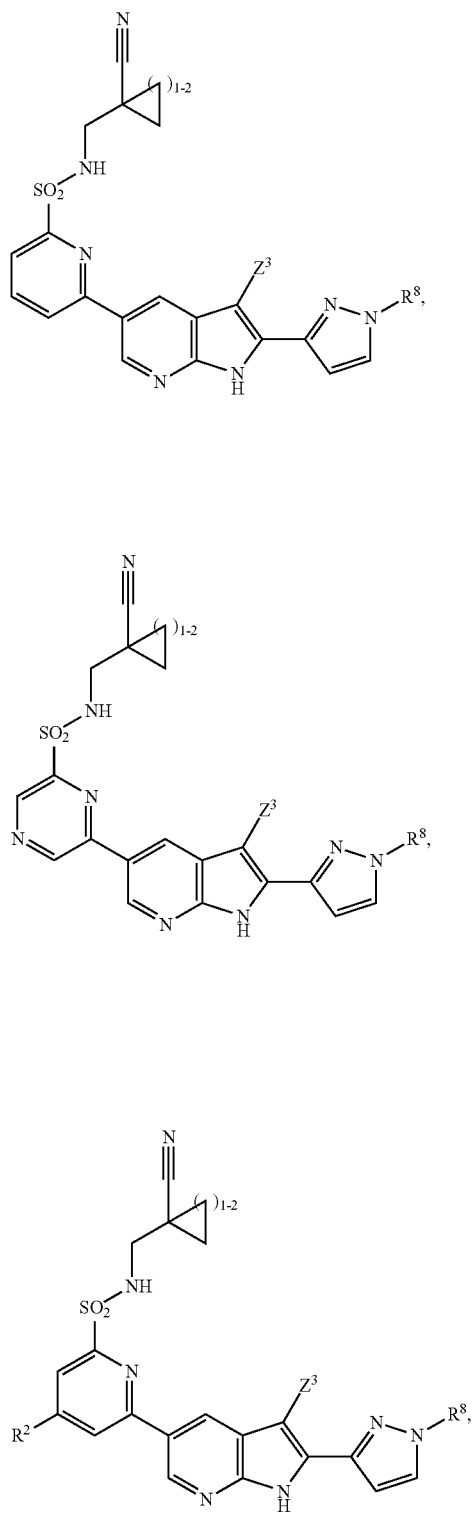
wherein R² is Cl or F.
Embodiment 8(g) of this disclosure relates to the compound according to Embodiment 1, 1(a), or 1(b), having one of the following Formulae, or a pharmaceutically acceptable salt, a solvate, a tautomer, an isomer, or a deuterated analog thereof:

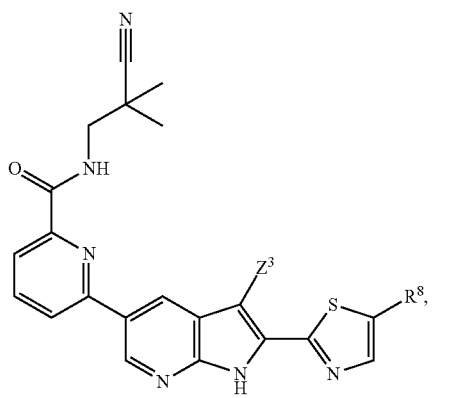
IV(e)
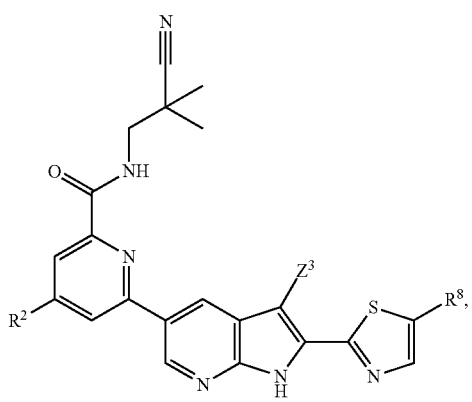
IV(f)
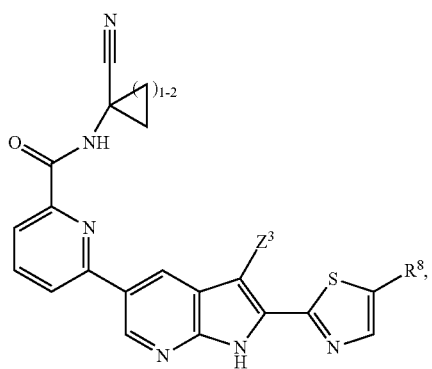
IV(g)
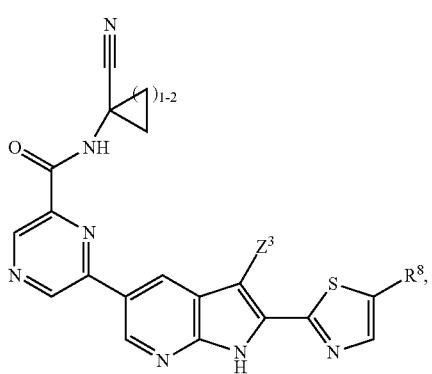
IV(h)
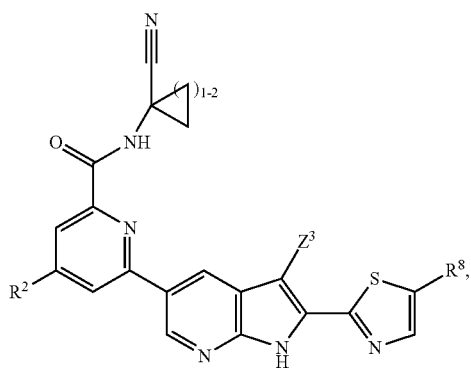
IV(i)
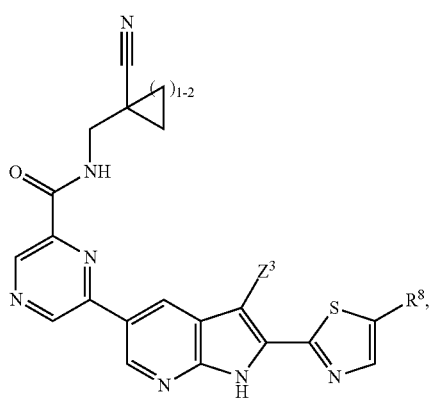
IV(j)
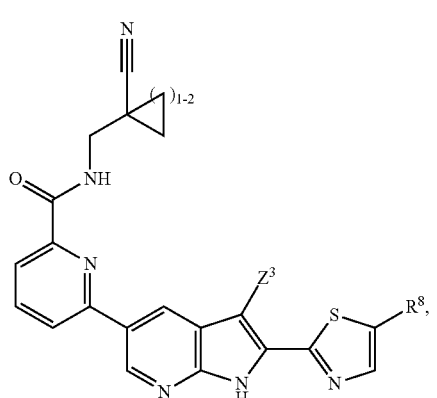
IV(k)
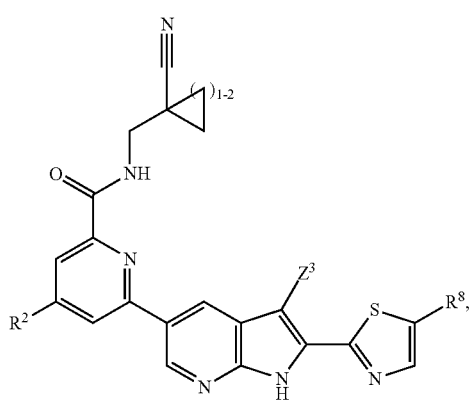
IV(l)

IV(m)
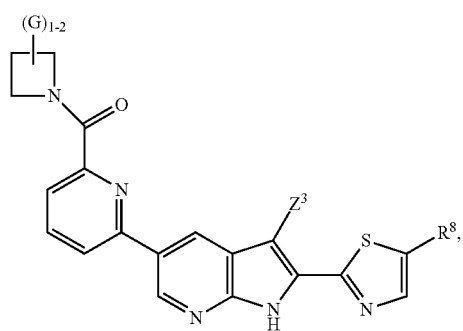
IV(o)
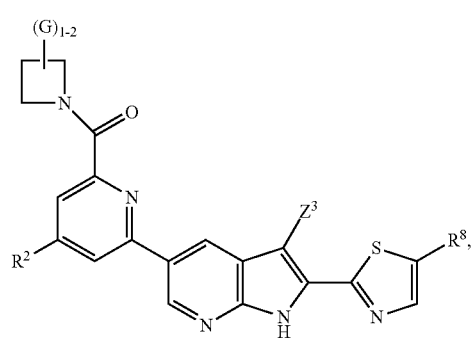
IV(p)
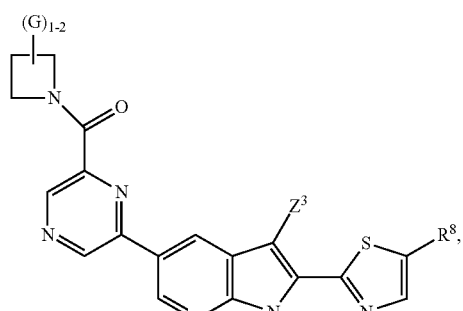
IV(q)
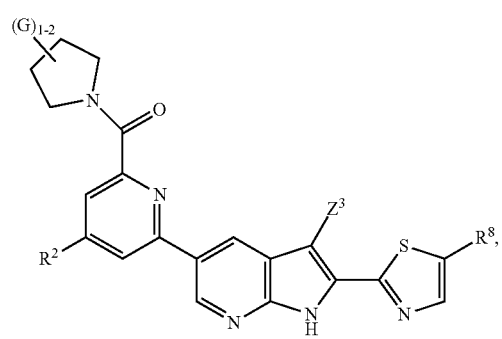
IV(r)
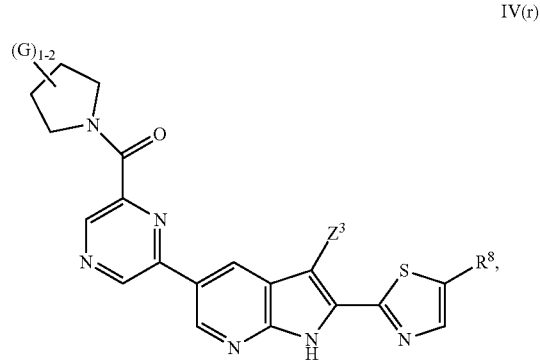
IV(t)
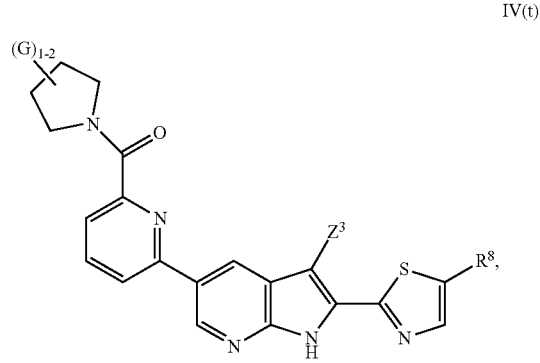
IV(u)
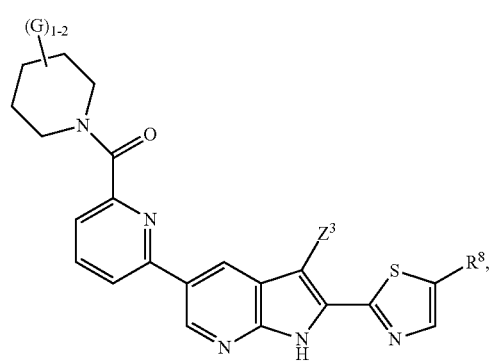
IV(v)
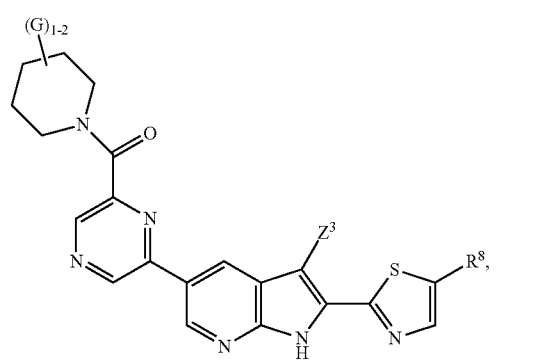

IV(w)
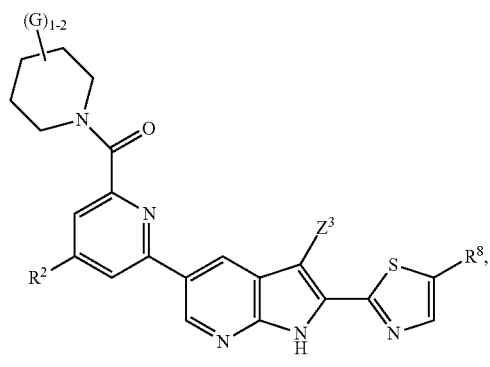
IV(aa)
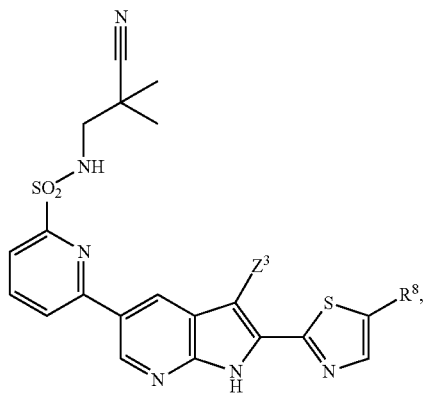
IV(x)
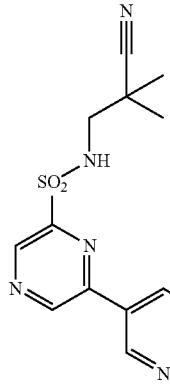
IV(bb)
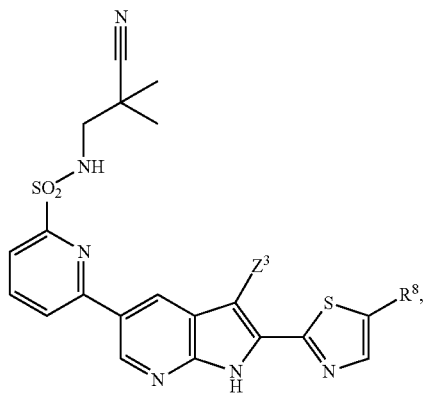
IV(y)
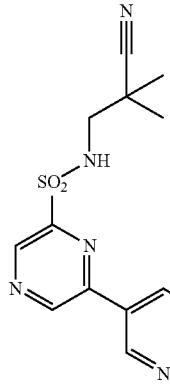
IV(cc)
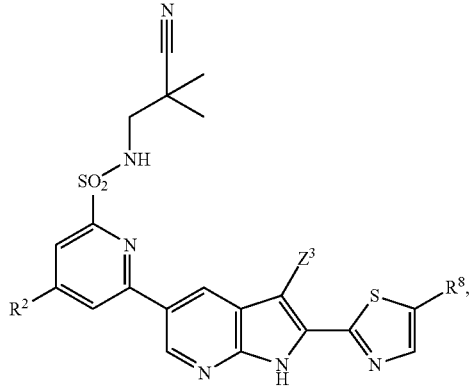
IV(z)
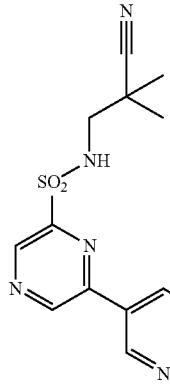
IV(dd)
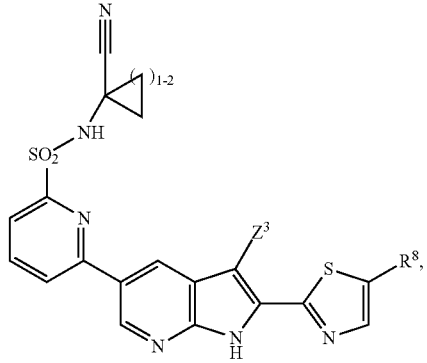

IV(ee)
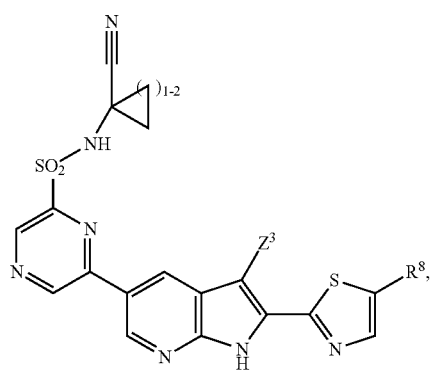
IV(ff)
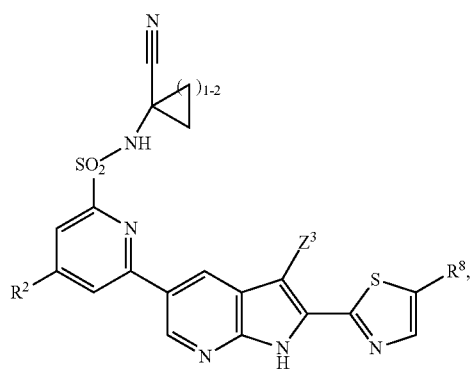
IV(gg)
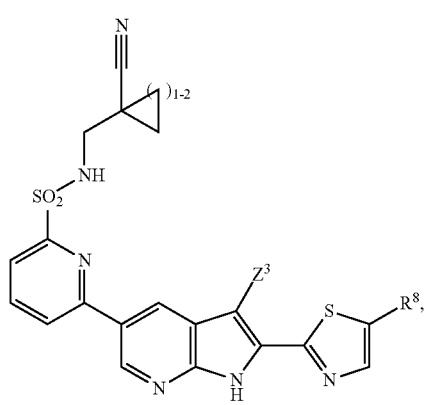
IV(hh)
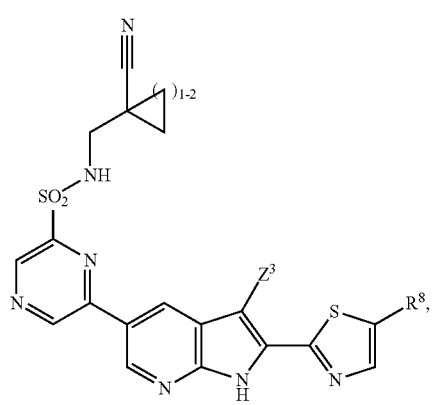
IV(ii)
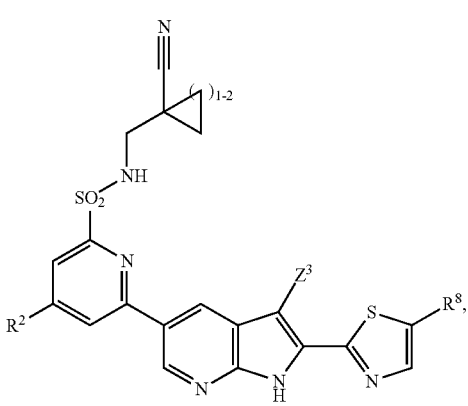
wherein $R^2$ is Cl or F.
Embodiment 8(h) of this disclosure relates to the compound according to Embodiment 1, 1(a), or 1(b), having one of the following Formulae, or a pharmaceutically acceptable salt, a solvate, a tautomer, an isomer, or a deuterated analog thereof:
V(a)
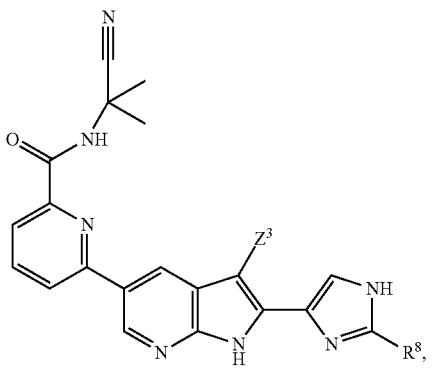
V(b)
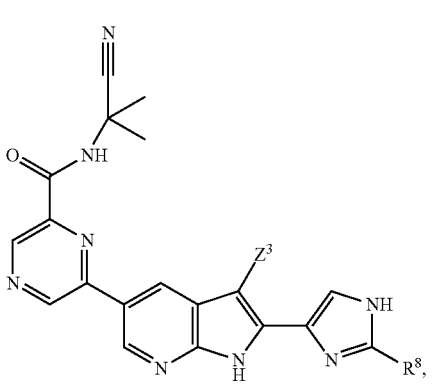

-continued
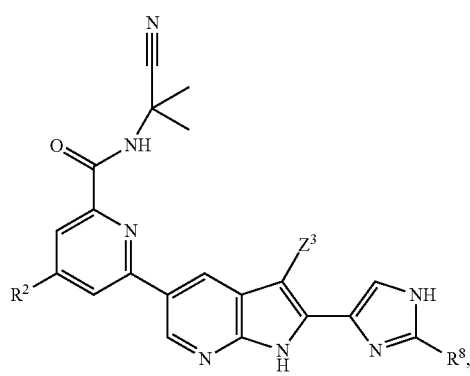
V(c)
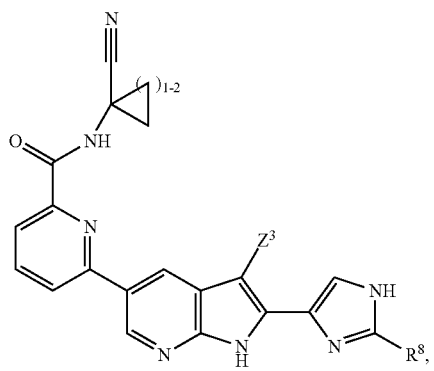
V(g)
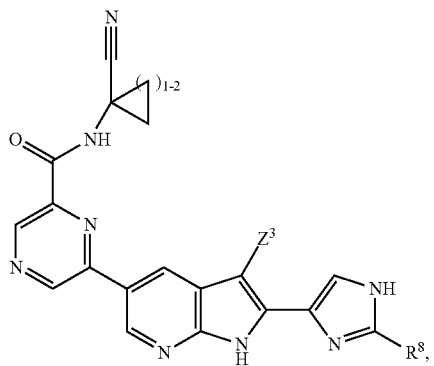
V(d)
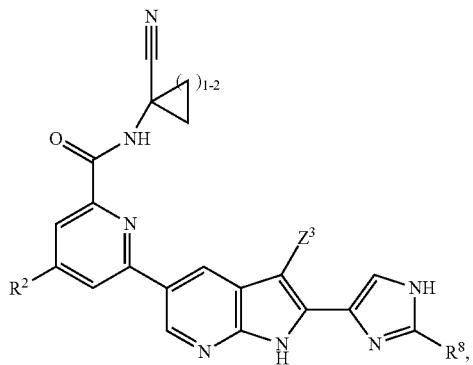
V(h)
V(e)
V(i)
V(f)
V(j)
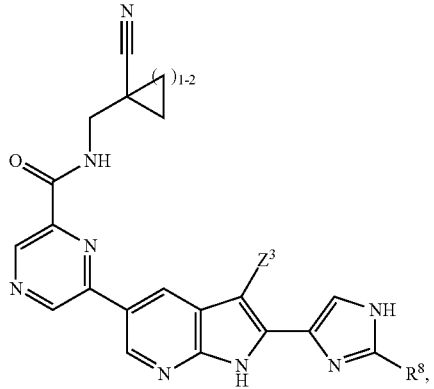

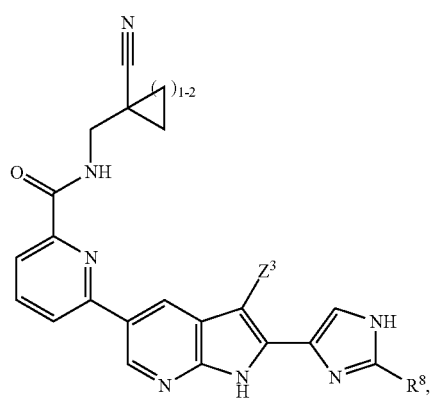 V(k)
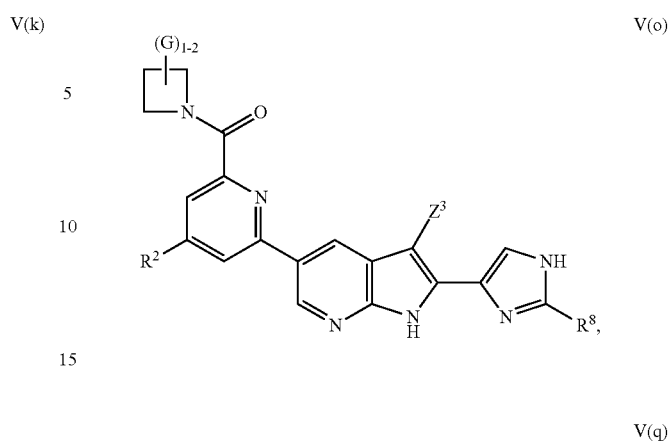 V(o)
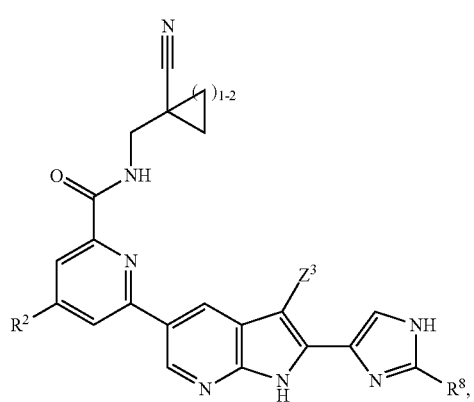 V(l)
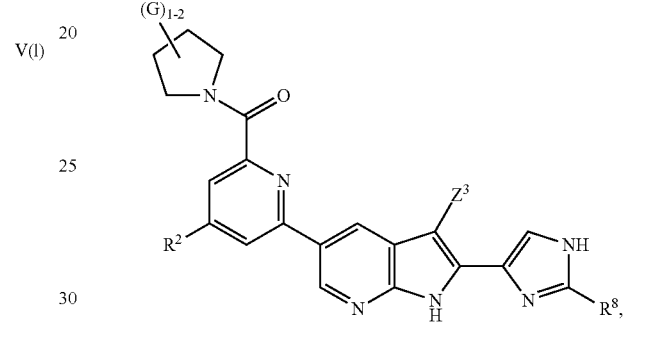 V(q)
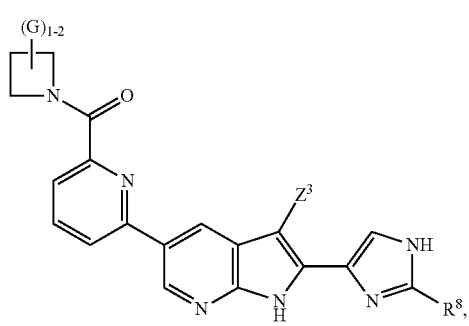 V(m)
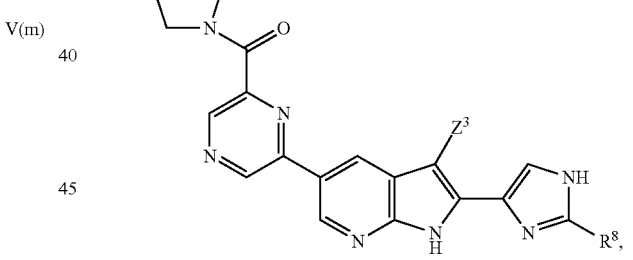 V(r)
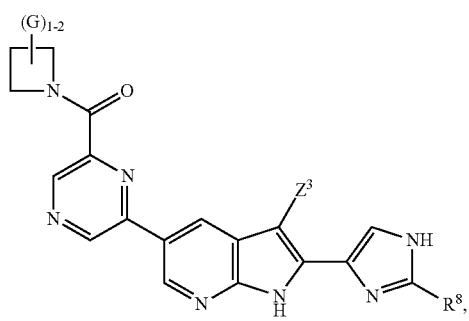 V(n)
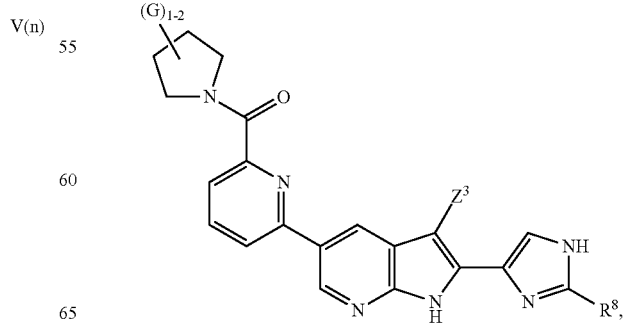 V(t)

V(u)
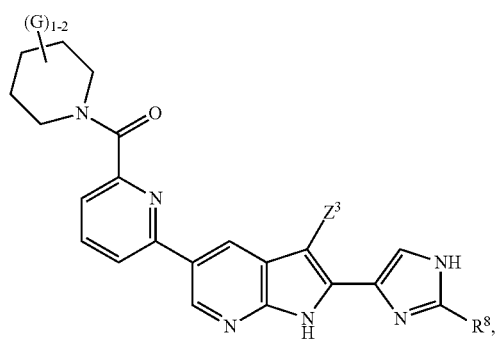
V(v)
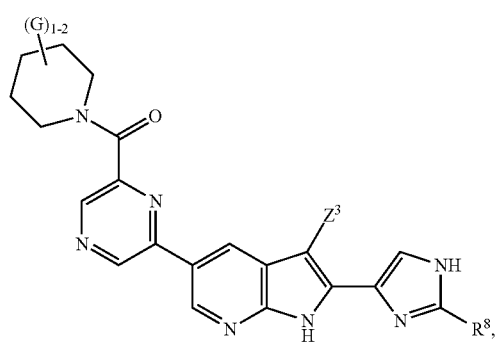
V(w)
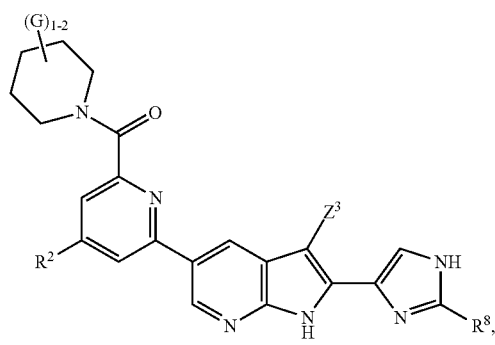
V(x)
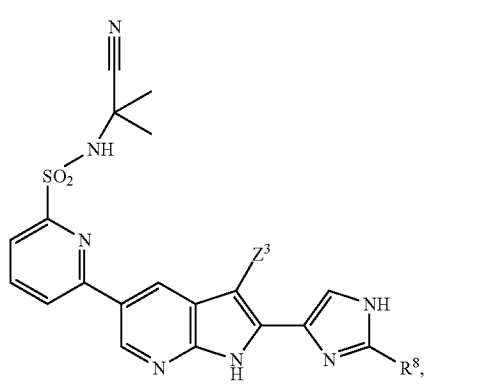
V(y)
V(z)
V(aa)
V(bb)
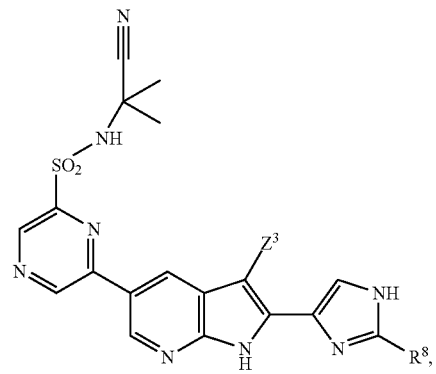

V(cc)
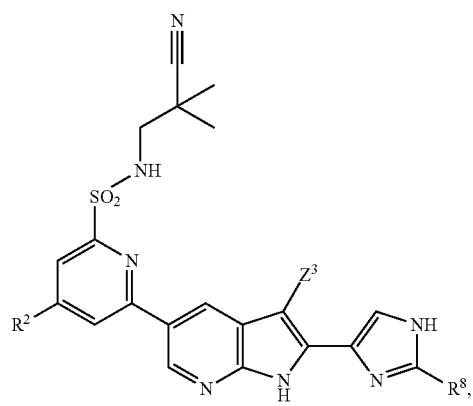
V(dd)
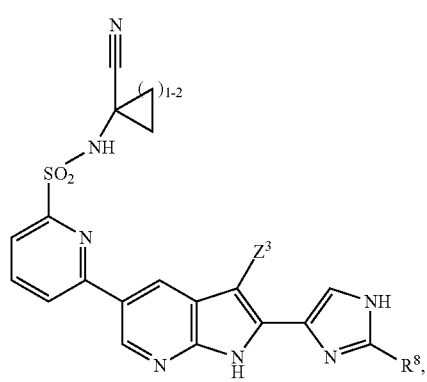
V(ee)
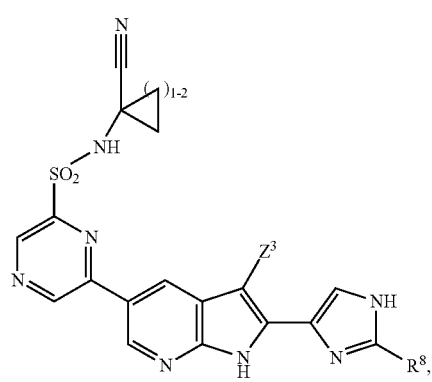
V(ff)
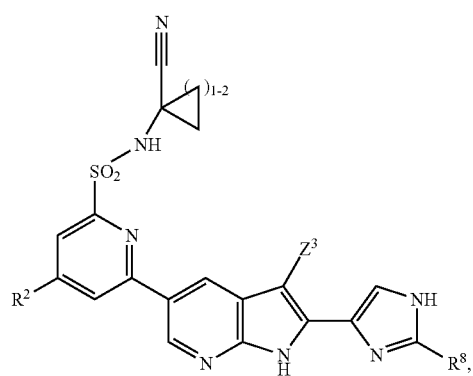
V(gg)
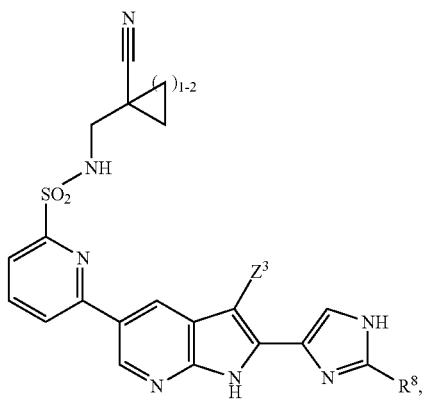
V(hh)
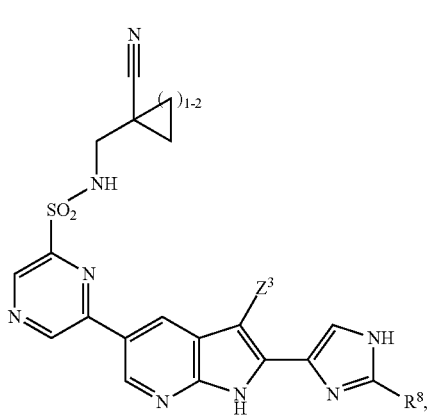
V(ii)
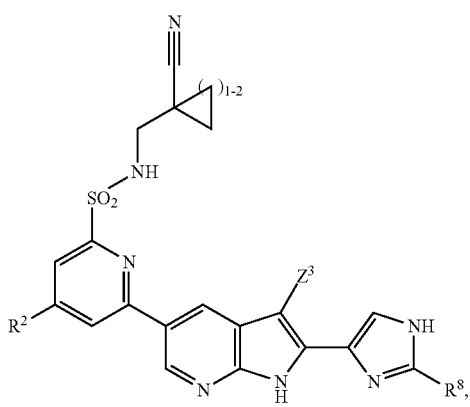
wherein R² is Cl or F.
Embodiment 8(i) of this disclosure relates to the compound according to Embodiment 1, 1(a), or 1(b), having one of the following Formulae, or a pharmaceutically acceptable salt, a solvate, a tautomer, an isomer, or a deuterated analog thereof:

VI(a)
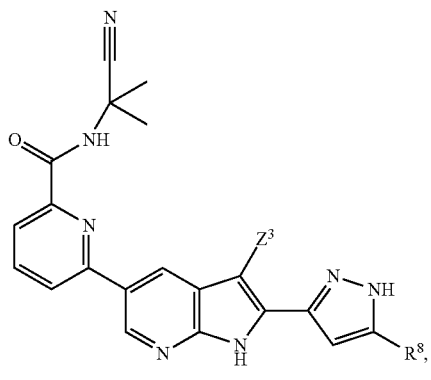
VI(e)
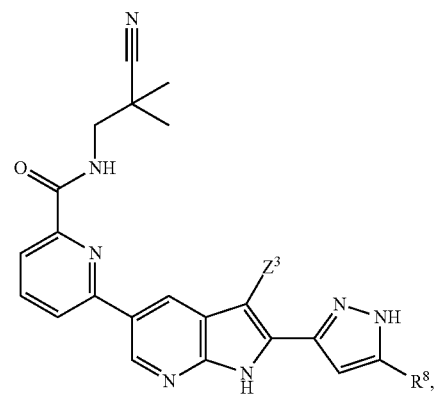
VI(b)
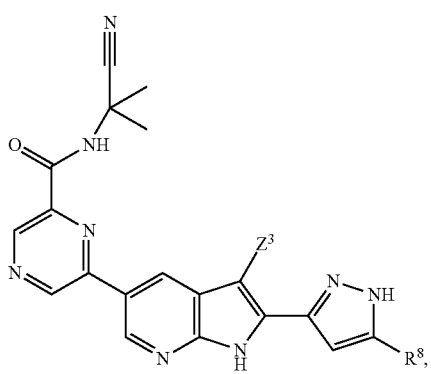
VI(f)
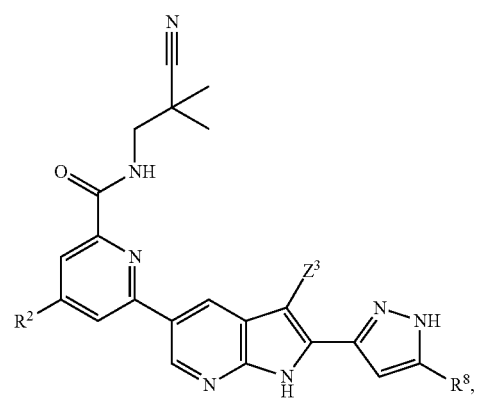
VI(c)
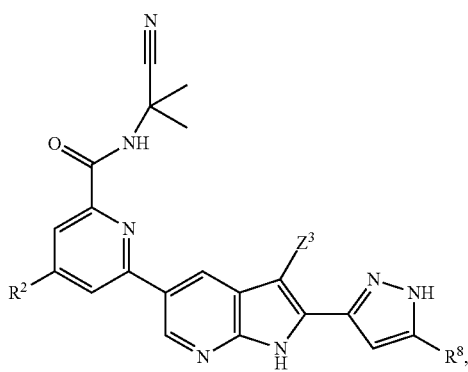
VI(g)
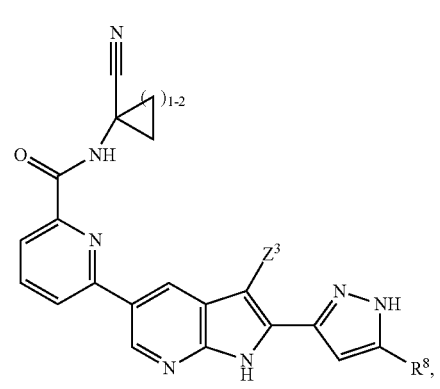
VI(d)
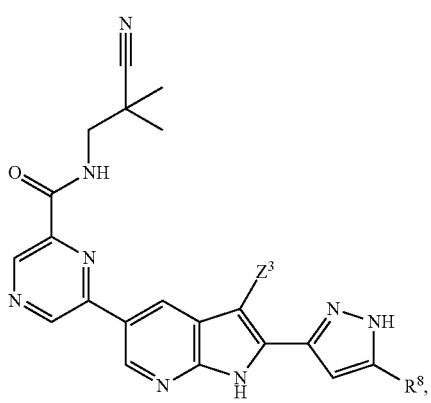
VI(h)
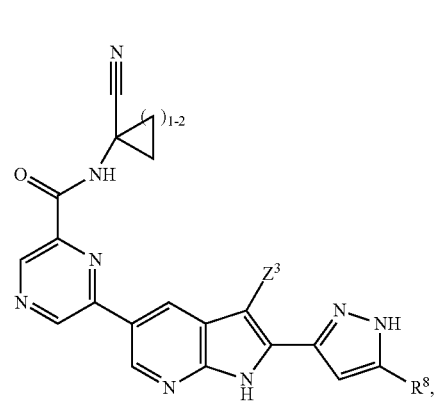

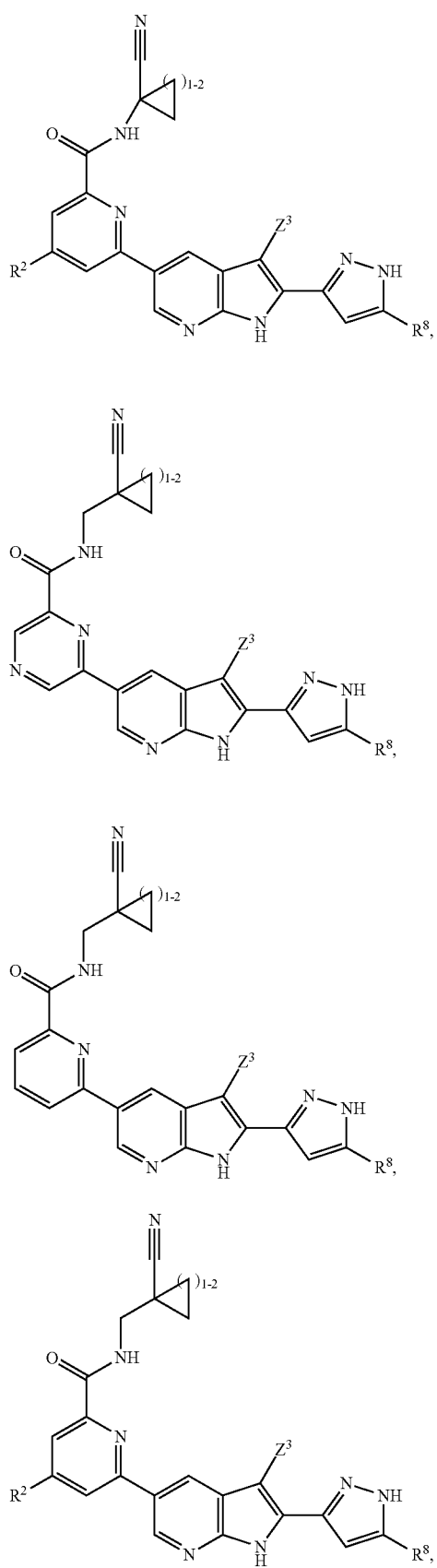
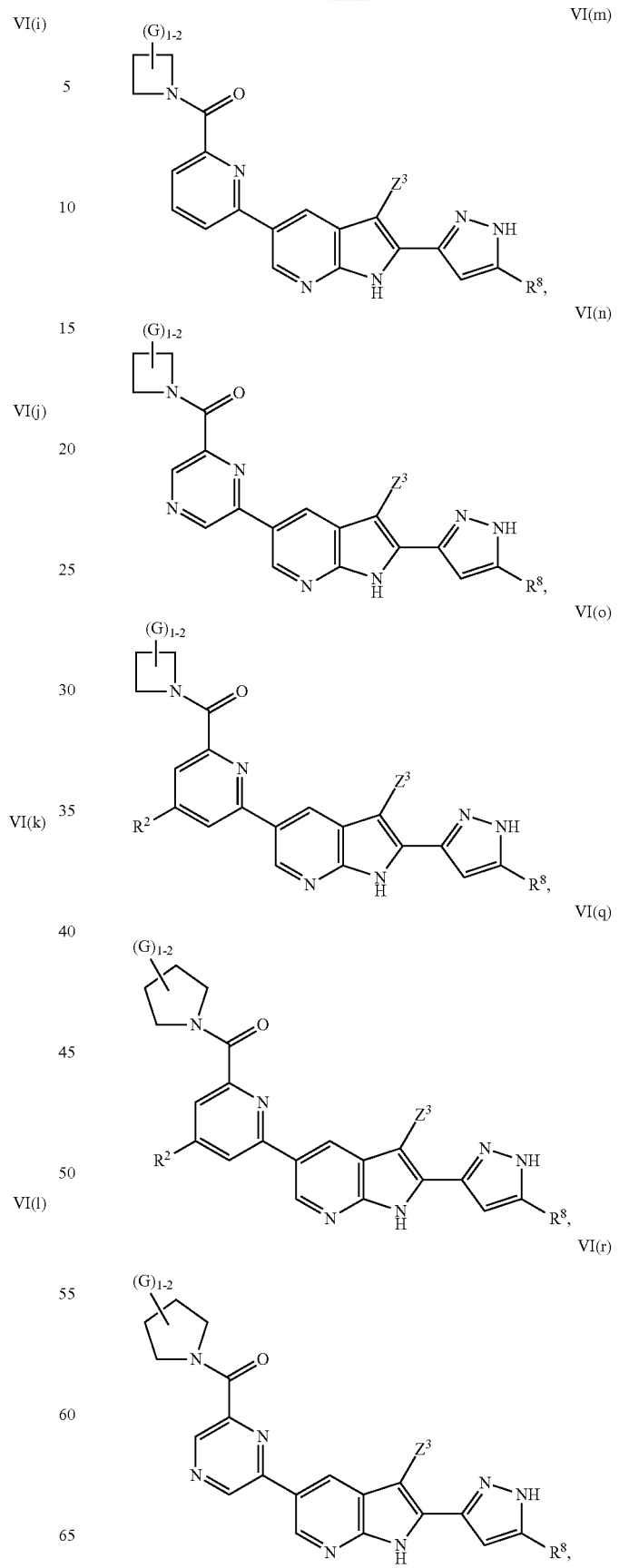

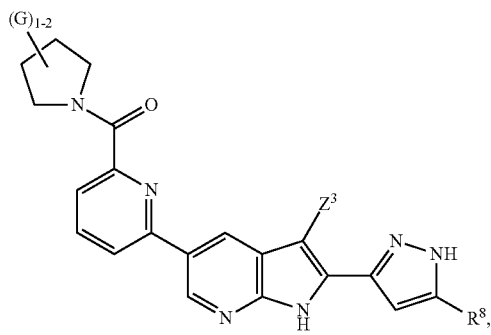
VI(t)
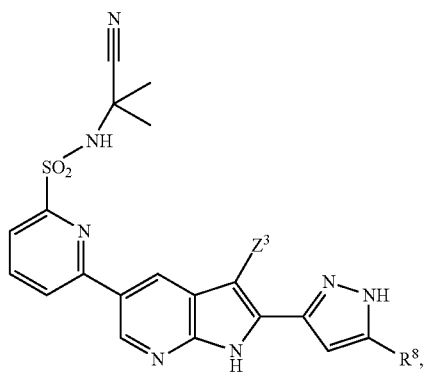
VI(x)
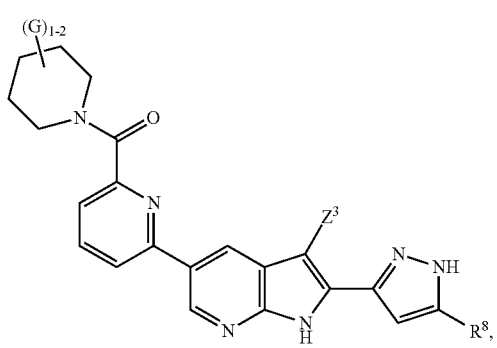
VI(u)
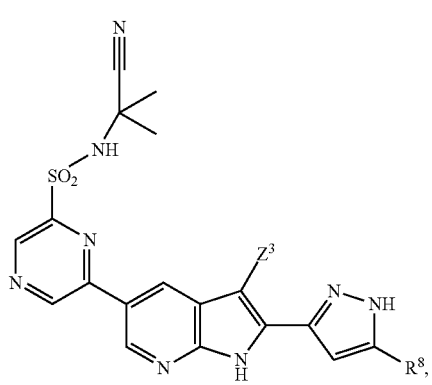
VI(y)
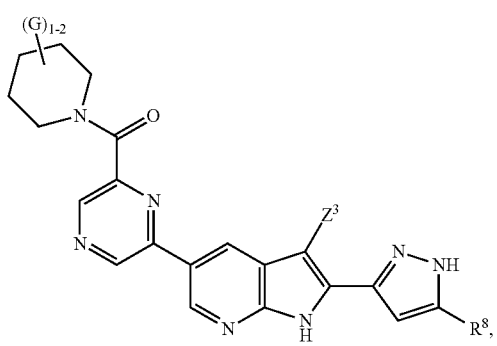
VI(v)
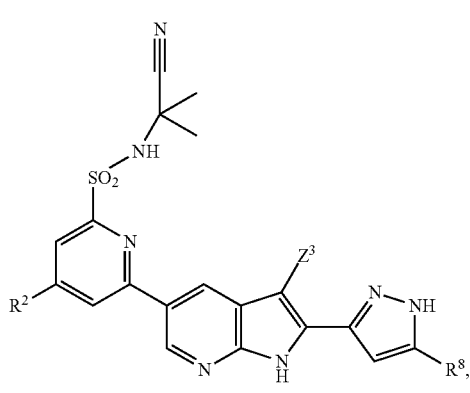
VI(z)
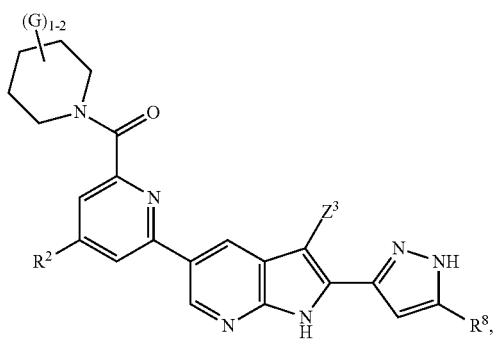
VI(w)
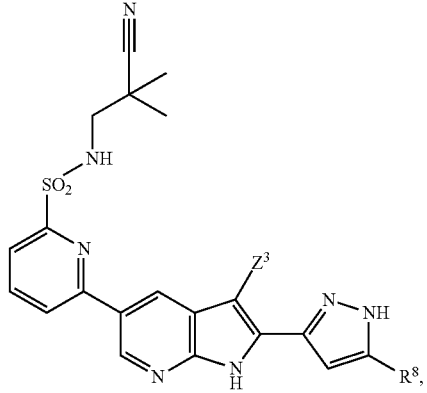
VI(aa)

VI(bb)
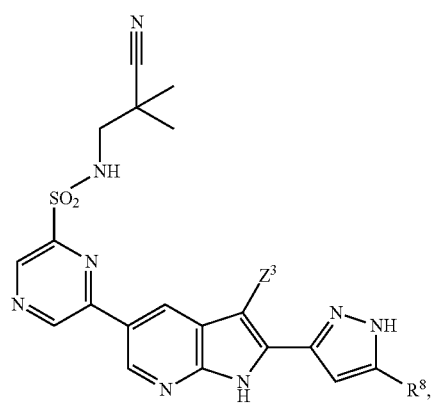
VI(cc)
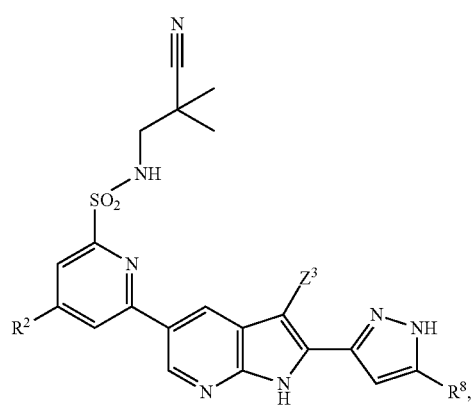
VI(dd)
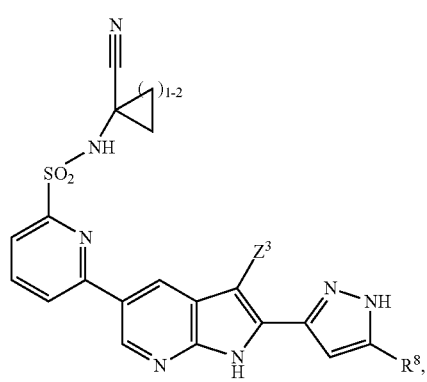
VI(ee)
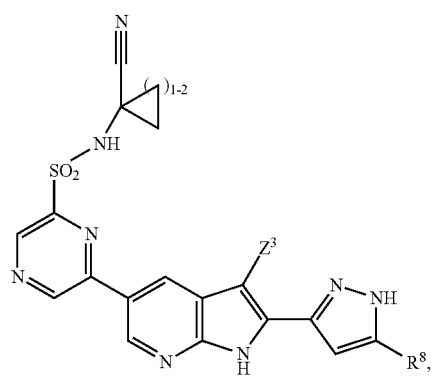
VI(ff)
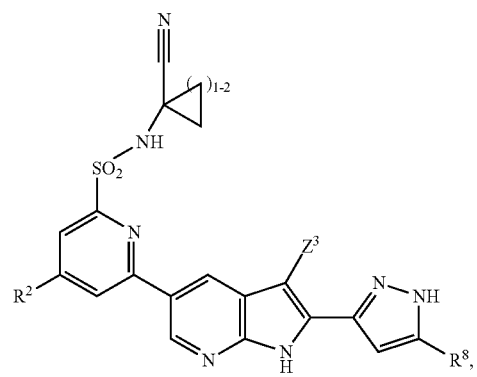
VI(gg)
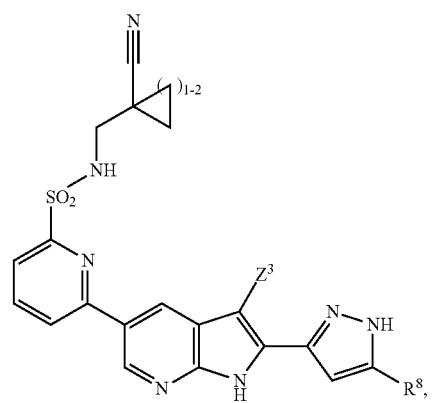
VI(hh)
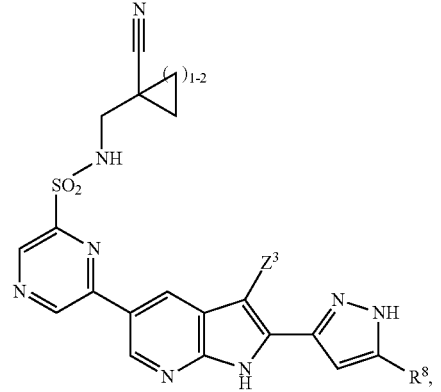
VI(ii)
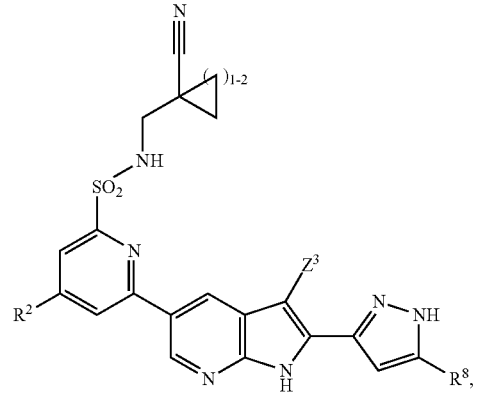
wherein R² is Cl or F.

Embodiment 8(j) of this disclosure relates to the compound according to Embodiment 1, 1(a), or 1(b), having one of the following Formulae, or a pharmaceutically acceptable salt, a solvate, a tautomer, an isomer, or a deuterated analog thereof:
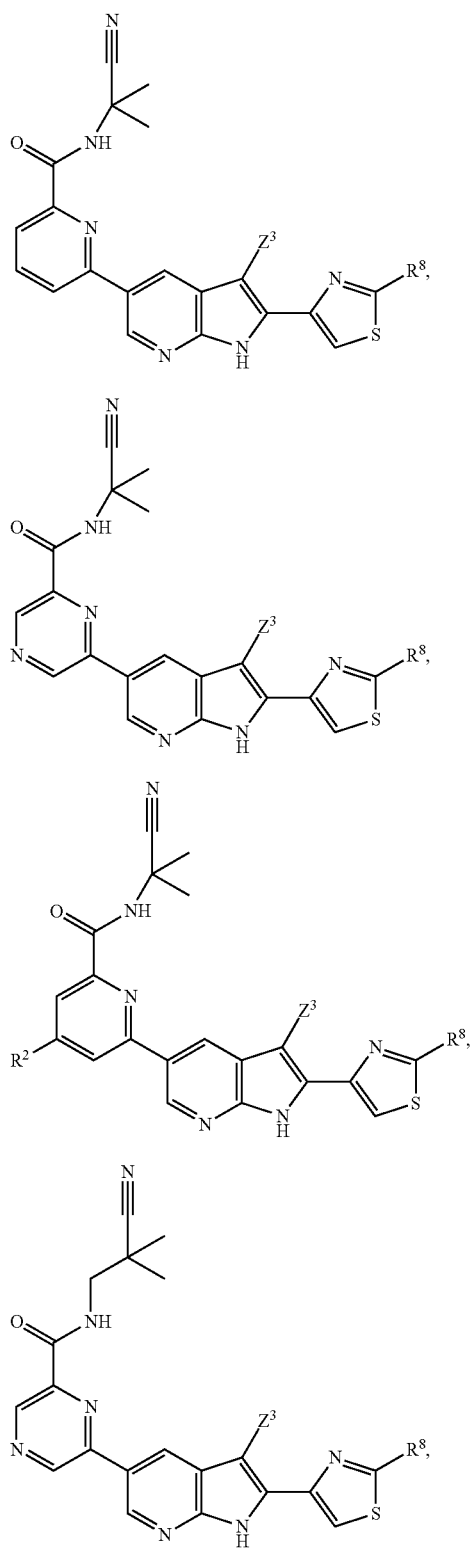
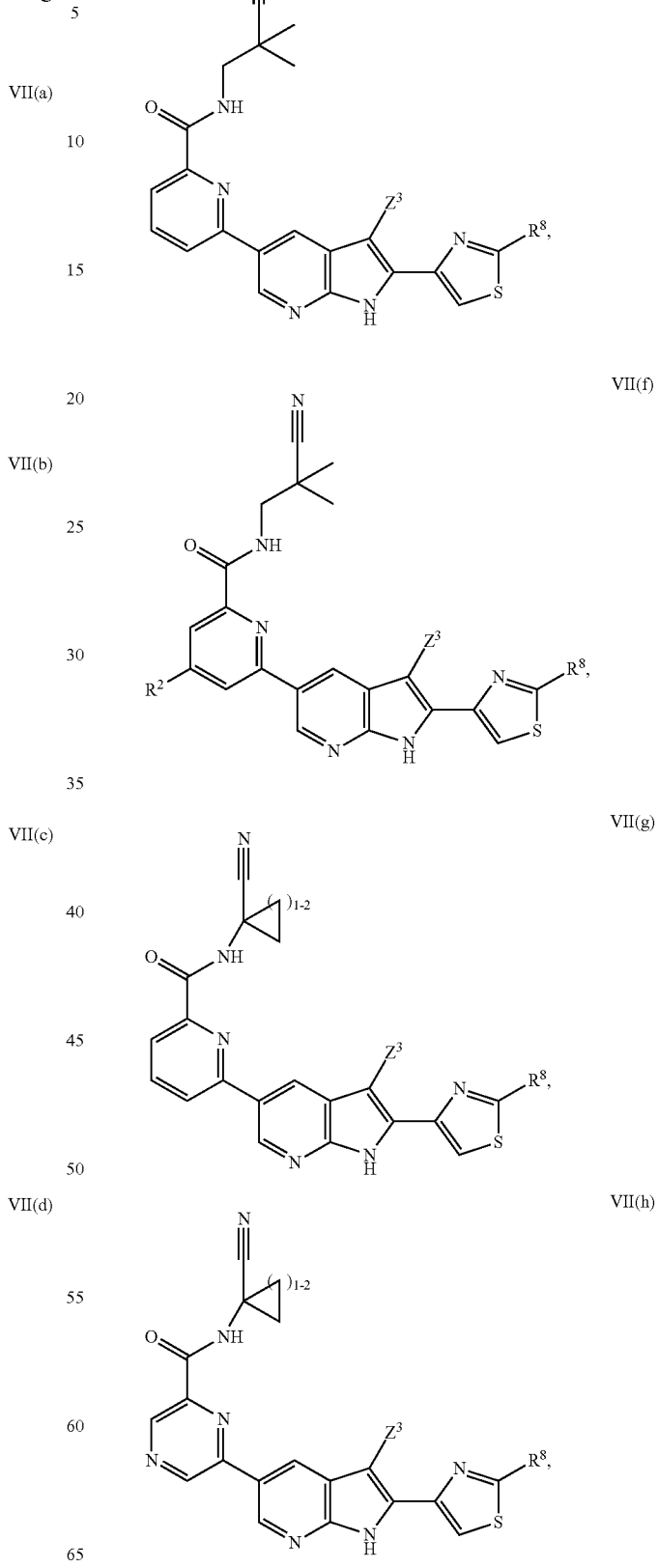

VII(i)
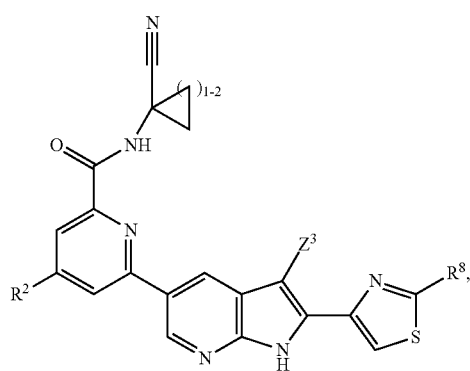
VII(j)
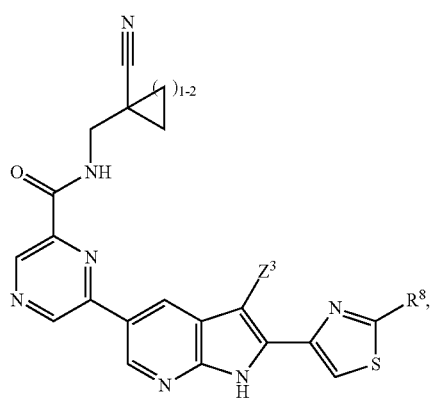
VII(k)
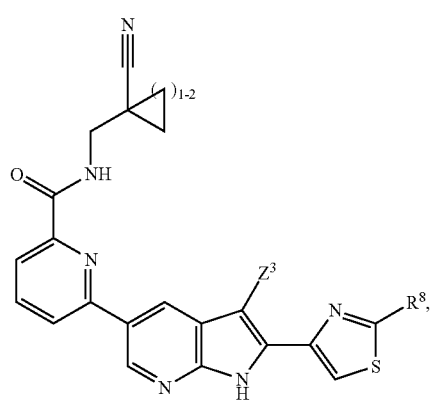
VII(l)
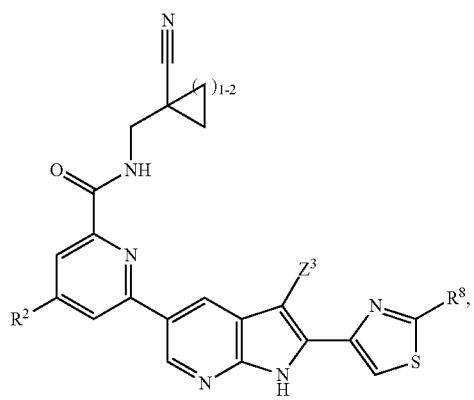
VII(m)
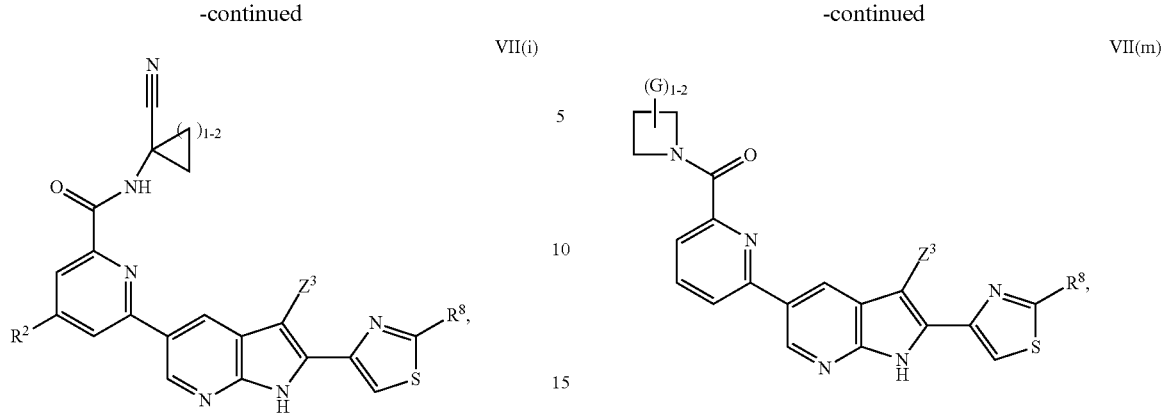
VII(n)
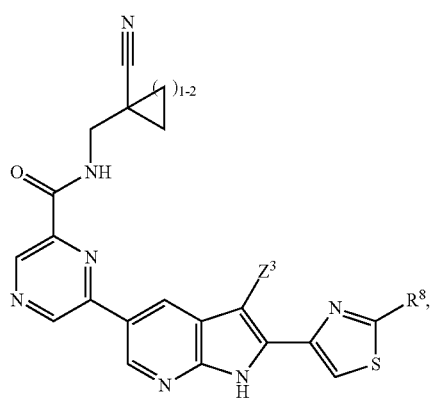
VII(o)
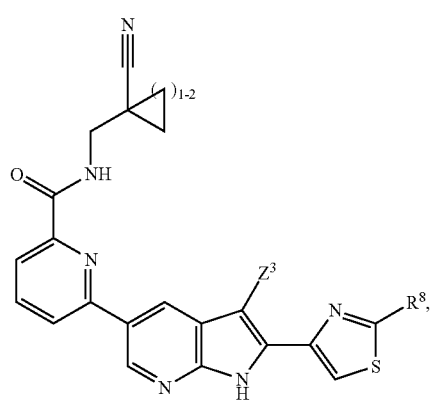
VII(q)
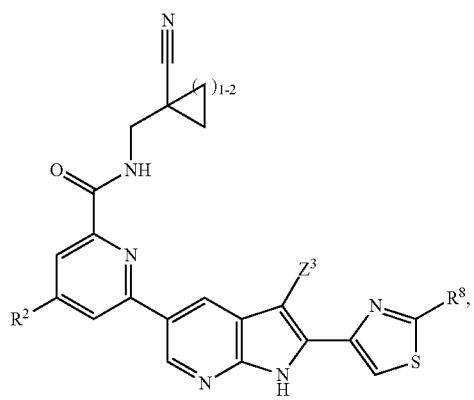

VII(r)
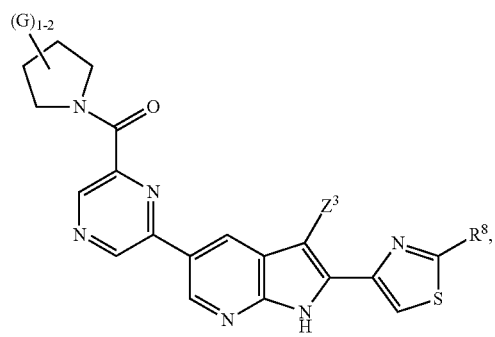
VII(w)
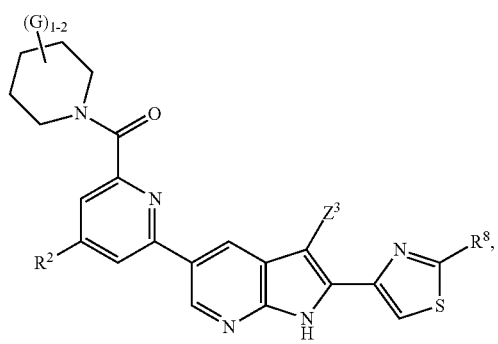
VII(t)
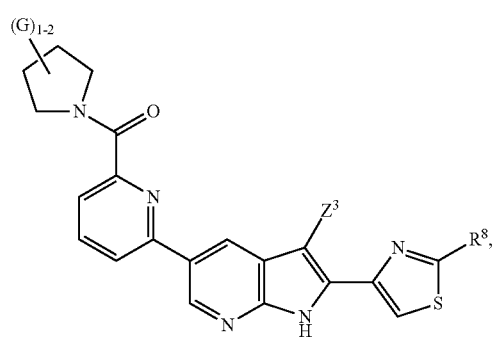
VII(x)
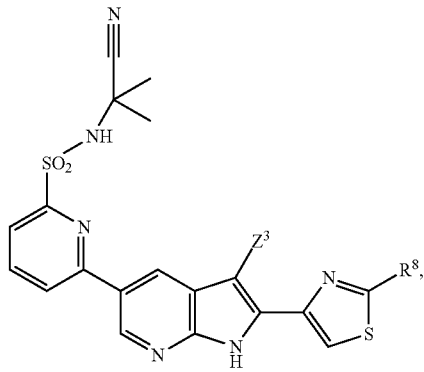
VII(u)
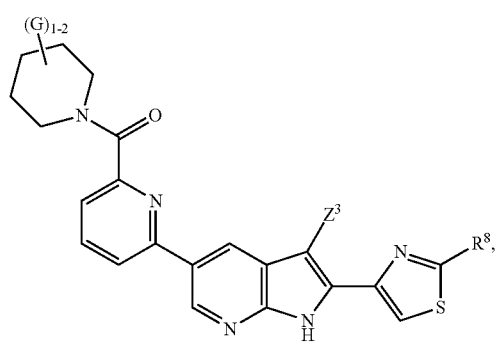
VII(y)
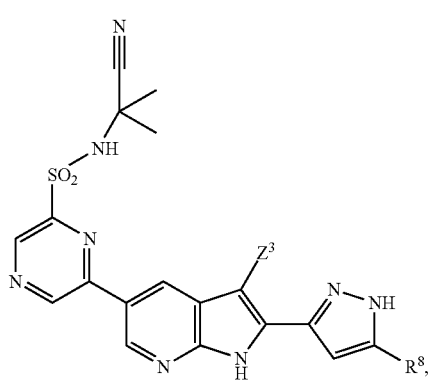
VII(v)
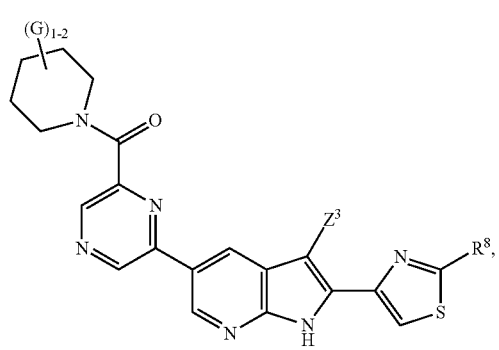
VII(z)
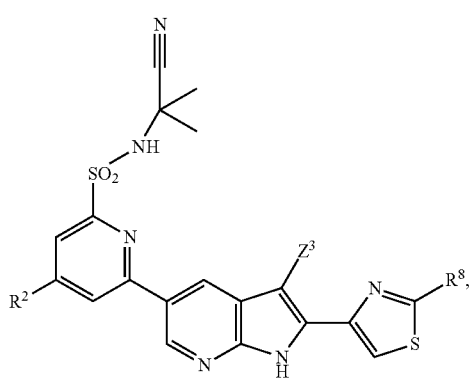

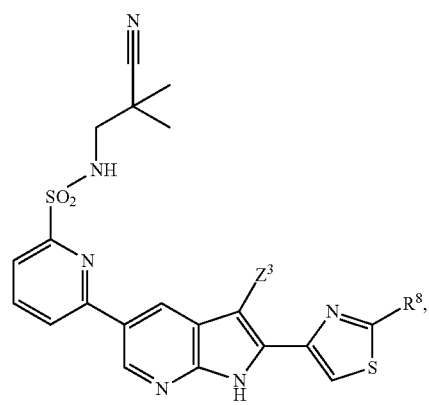
VII(aa)
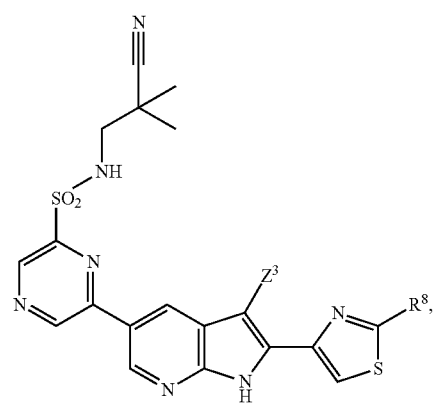
VII(bb)
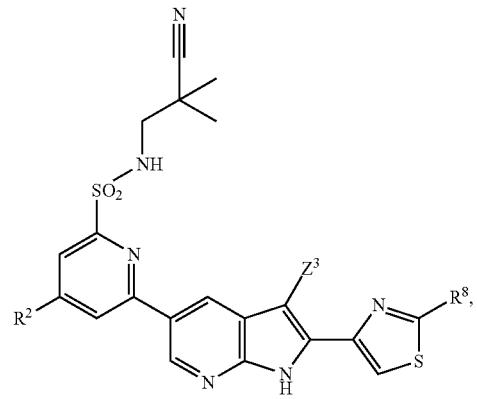
VII(cc)
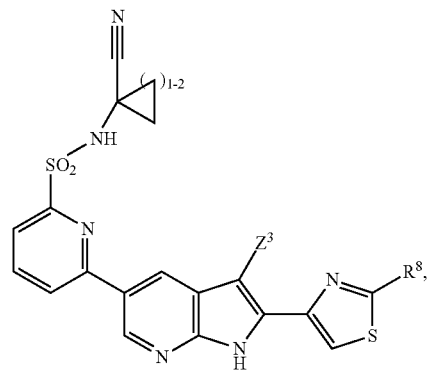
VII(dd)
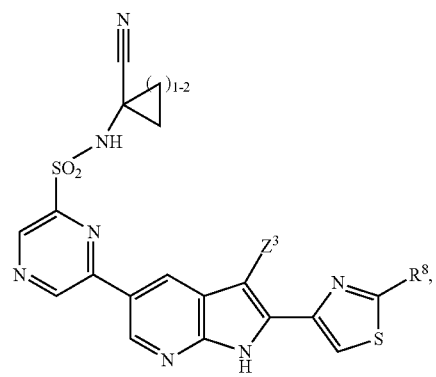
VII(ee), VII(ff), VII(gg), VII(hh)

-continued

VII(ii)

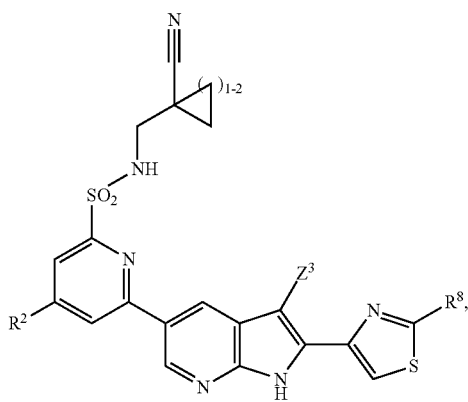

wherein R² is Cl or F.

Embodiment 9 of this disclosure relates to the compound according to Embodiment 8, having one of Formulae I(a), I(e), I(g), I(k), I(m), I(t), I(u), I(x), I(aa), I(dd), I(gg), I(jj), or I(oo).

Embodiment 10 of this disclosure relates to the compound according to Embodiment 8, having one of Formulae I(c), I(f), I(i), I(l), I(o), I(q), I(w), I(z), I(cc), I(ff), I(ii), I(ll), or I(pp).

Embodiment 11 of this disclosure relates to the compound according to Embodiment 8, having one of Formulae I(b), I(d), I(h), I(j), I(n), I(r), I(v), I(y), I(bb), I(ee), I(hh), I(kk), or I(mm).

Embodiment 12 of this disclosure relates to the compound according to Embodiment 8, having one of Formulae I(a), I(b), I(c), I(d), I(e), or I(f).

Embodiment 13 of this disclosure relates to the compound according to any one of Embodiments 1 to 12, wherein $R^8$ is —$CH_3$, —$CH_2F$, —$CHF_2$, —$CF_3$, —$CH_2CH_3$, —$CH_2CH_2F$, —$CH_2CHF_2$, —$CH_2CF_3$, —$C(CH_3)_2$—OH, —$CH_2C(CH_3)_2$—OH, —$CH_2$—$S(O)_2$—$CH_3$, —$CH_2$—CN, —$CH_2$-oxetanyl, —$CH_2$—C(O)—$NH_2$, —$CH_2$—C(O)—N($C_1$-$C_3$alkyl)$_2$, or —$CH_2$—C(O)-heterocycloalkyl.

Embodiment 14 of this disclosure relates to the compound according to any one of Embodiments 1 to 12, wherein $R^8$ is —$CHF_2$, —$C(CH_3)_2$—OH, —$CH_2C(CH_3)_2$—OH, —$CH_2$—$S(O)_2$—$CH_3$, —$CH_2$—C(O)—$NH_2$, —$CH_2$—C(O)—N($CH_3$)$_2$, or —$CH_2$—C(O)-pyridyl.

Embodiment 15 of this disclosure relates to the compound according to any one of Embodiments 1 to 14, wherein $Z^3$ is F or $C_1$.

Embodiment 15(a) of this disclosure relates to the compound according to any one of Embodiments 1 to 2(b) and 3-14, wherein $Z^3$ is hydrogen.

Embodiment 15(b) of this disclosure relates to the compound according to any one of Embodiments 1 to 14, wherein $Z^3$ is F, Cl, or Br.

Embodiment 16 of this disclosure relates to a compound, or a pharmaceutically acceptable salt, a solvate, a tautomer, an isomer, or a deuterated analog thereof, of Table I:

TABLE I

| Number | Compound | Name | M − H | M + H |
|---|---|---|---|---|
| P-001 |  | 6-(2-(1-(cyanomethyl)-1H-pyrazol-4-yl)-1H-pyrrolo[2,3-b]pyridin-5-yl)-N-(2-cyanopropan-2-yl)picolinamide |  | 410.95 |
| P-002 |  | N-(2-cyanopropan-2-yl)-6-(2-(4-(2-hydroxypropan-2-yl)phenyl)-1H-pyrrolo[2,3-b]pyridin-5-yl)picolinamide |  |  |

TABLE I-continued

| Number | Name | M − H | M + H |
|---|---|---|---|
| P-003 | N-(1-cyano-1-methyl-ethyl)-6-[2-[1-(difluoromethyl)-3,5-difluoro-pyrazol-4-yl]-3-fluoro-1H-pyrrolo[2,3-b]pyridin-5-yl]pyridine-2-carboxamide | | 476.1 |
| P-004 | N-(1-cyano-1-methyl-ethyl)-6-[2-[1-(difluoromethyl)pyrazol-4-yl]-3-fluoro-1H-pyrrolo[2,3-b]pyridin-5-yl]pyridine-2-carboxamide | 437.95 | |
| P-005 | 6-[3-bromo-2-[1-(difluoromethyl)pyrazol-4-yl]-1H-pyrrolo[2,3-b]pyridin-5-yl]-N-(1-cyano-1-methyl-ethyl)pyridine-2-carboxamide | 499.8 | |
| P-006 | N-(1-cyanocyclopropyl)-6-(2-(1-(difluoromethyl)-1H-pyrazol-4-yl)-1H-pyrrolo[2,3-b]pyridin-5-yl)picolinamide | | 420.1 |

TABLE I-continued

| Number | Compound | Name | M − H | M + H |
|---|---|---|---|---|
| P-007 | | N-(1-cyanocyclobutyl)-6-(2-(1-(difluoromethyl)-1H-pyrazol-4-yl)-1H-pyrrolo[2,3-b]pyridin-5-yl)picolinamide | | 434.1 |
| P-008 | | N-((1-cyanocyclopropyl)methyl)-6-(2-(1-(difluoromethyl)-1H-pyrazol-4-yl)-1H-pyrrolo[2,3-b]pyridin-5-yl)picolinamide | | 434.1 |
| P-009 | | 6-(2-(1-(difluoromethyl)-1H-pyrazol-4-yl)-1H-pyrrolo[2,3-b]pyridin-5-yl)-N-(3-hydroxycyclobutyl)picolinamide | | 425.1 |
| P-010 | | 6-(2-(1-(difluoromethyl)-1H-pyrazol-4-yl)-1H-pyrrolo[2,3-b]pyridin-5-yl)-N-(1,1-dioxidothietan-3-yl)picolinamide | | 459.1 |

TABLE I-continued

| Number | Compound | Name | M − H | M + H |
|---|---|---|---|---|
| P-011 | | 6-(2-(1-(difluoromethyl)-1H-pyrazol-4-yl)-1H-pyrrolo[2,3-b]pyridin-5-yl)-N-(2-hydroxy-2-methylpropyl)picolinamide | | 427.1 |
| P-012 | | 6-(2-(1-(difluoromethyl)-1H-pyrazol-4-yl)-1H-pyrrolo[2,3-b]pyridin-5-yl)-N-((1-hydroxycyclopropyl)methyl)picolinamide | | 425.1 |
| P-013 | | 6-(2-(1-(difluoromethyl)-1H-pyrazol-4-yl)-1H-pyrrolo[2,3-b]pyridin-5-yl)-N-((1-hydroxycyclobutyl)methyl)picolinamide | | 439.1 |
| P-014 | | 6-(2-(1-(difluoromethyl)-1H-pyrazol-4-yl)-1H-pyrrolo[2,3-b]pyridin-5-yl)-N-(oxetan-3-yl)picolinamide | | 411.1 |

TABLE I-continued

| Number | Compound | Name | M − H | M + H |
|---|---|---|---|---|
| P-015 | | 6-(2-(1-(difluoromethyl)-1H-pyrazol-4-yl)-1H-pyrrolo[2,3-b]pyridin-5-yl)-N-(1-methylazetidin-3-yl)picolinamide | | 421.4 |
| P-016 | | 6-(2-(1-(difluoromethyl)-1H-pyrazol-4-yl)-1H-pyrrolo[2,3-b]pyridin-5-yl)-N-(1H-imidazol-2-yl)picolinamide | | 421.1 |
| P-017 | | 6-(2-(1-(difluoromethyl)-1H-pyrazol-4-yl)-1H-pyrrolo[2,3-b]pyridin-5-yl)-N-(1H-imidazol-5-yl)picolinamide | | 421.1 |
| P-018 | | 6-(2-(1-(difluoromethyl)-1H-pyrazol-4-yl)-1H-pyrrolo[2,3-b]pyridin-5-yl)-N-(1H-pyrazol-5-yl)picolinamide | | 421.2 |

TABLE I-continued

| Number | Compound | Name | M − H | M + H |
|---|---|---|---|---|
| P-019 | 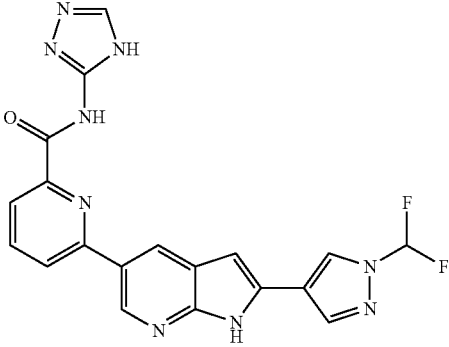 [SMILES: O=C(Nc1nnc[nH]1)c1cccc(-c2cnc3[nH]c(-c4cnn(C(F)F)c4)cc3c2)n1] | 6-(2-(1-(difluoromethyl)-1H-pyrazol-4-yl)-1H-pyrrolo[2,3-b]pyridin-5-yl)-N-(4H-1,2,4-triazol-3-yl)picolinamide | | 423.1 |
| P-020 | 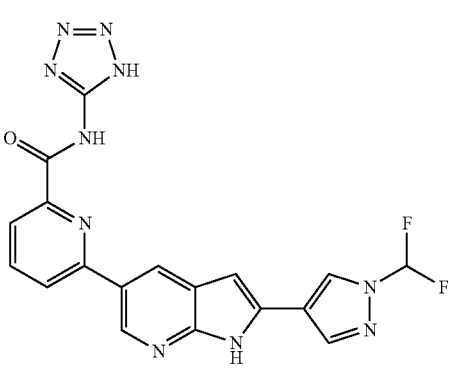 [SMILES: O=C(Nc1nnn[nH]1)c1cccc(-c2cnc3[nH]c(-c4cnn(C(F)F)c4)cc3c2)n1] | 6-(2-(1-(difluoromethyl)-1H-pyrazol-4-yl)-1H-pyrrolo[2,3-b]pyridin-5-yl)-N-(1H-tetrazol-5-yl)picolinamide | | |
| P-021 | 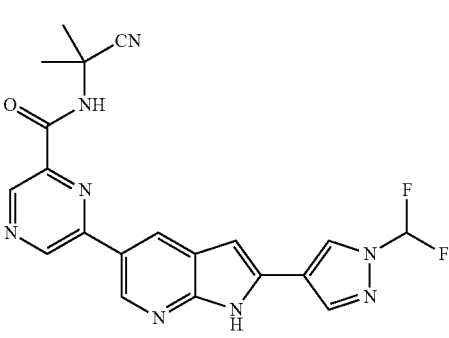 [SMILES: CC(C)(C#N)NC(=O)c1cncc(-c2cnc3[nH]c(-c4cnn(C(F)F)c4)cc3c2)n1] | N-(2-cyanopropan-2-yl)-6-(2-(1-(difluoromethyl)-1H-pyrazol-4-yl)-1H-pyrrolo[2,3-b]pyridin-5-yl)pyrazine-2-carboxamide | | 423.1 |
| P-022 | 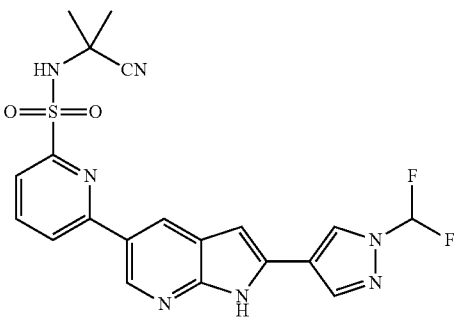 [SMILES: CC(C)(C#N)NS(=O)(=O)c1cccc(-c2cnc3[nH]c(-c4cnn(C(F)F)c4)cc3c2)n1] | N-(2-cyanopropan-2-yl)-6-(2-(1-(difluoromethyl)-1H-pyrazol-4-yl)-1H-pyrrolo[2,3-b]pyridin-5-yl)pyridine-2-sulfonamide | | |

TABLE I-continued

| Number | Compound | Name | M − H | M + H |
|---|---|---|---|---|
| P-023 | | N-(cyanomethyl)-6-(2-(1-(difluoromethyl)-1H-pyrazol-4-yl)-1H-pyrrolo[2,3-b]pyridin-5-yl)pyridine-2-sulfonamide | | |
| P-024 | | N-(2-cyanopropan-2-yl)-6-(2-(1-(difluoromethyl)-1H-pyrazol-4-yl)-1H-pyrrolo[2,3-b]pyridin-5-yl)-4-fluoropicolinamide | | 440.05 |
| P-025 | | N-(2-cyano-2-methylpropyl)-6-(2-(1-(difluoromethyl)-1H-pyrazol-4-yl)-1H-pyrrolo[2,3-b]pyridin-5-yl)-4-fluoropicolinamide | | |
| P-026 | | N-(1-cyanocyclopropyl)-6-(2-(1-(difluoromethyl)-1H-pyrazol-4-yl)-1H-pyrrolo[2,3-b]pyridin-5-yl)pyridine-2-sulfonamide | | |
| P-027 | | 2-(4-(5-(6-(N-(1-cyanocyclopropyl)sulfamoyl)pyridin-2-yl)-1H-pyrrolo[2,3-b]pyridin-2-yl)-1H-pyrazol-1-yl)-N,N-dimethylacetamide | | |

TABLE I-continued

| Number | Compound | Name | M − H | M + H |
|---|---|---|---|---|
| P-028 | | N-(2-cyanopropan-2-yl)-6-(2-(1-(2-(dimethylamino)-2-oxoethyl)-1H-pyrazol-4-yl)-1H-pyrrolo[2,3-b]pyridin-5-yl)picolinamide | | |
| P-029 | | 6-(2-(1-(2-amino-2-oxoethyl)-1H-pyrazol-4-yl)-1H-pyrrolo[2,3-b]pyridin-5-yl)-N-(2-cyanopropan-2-yl)picolinamide | | |
| P-030 | | N-(2-cyanopropan-2-yl)-6-(2-(1-(difluoromethyl)-1H-pyrazol-4-yl)-3H-imidazo[4,5-b]pyridin-6-yl)picolinamide | | |
| P-031 | | N-(2-cyanopropan-2-yl)-6-(2-(1-(2-oxo-2-(piperidin-1-yl)ethyl)-1H-pyrazol-4-yl)-1H-pyrrolo[2,3-b]pyridin-5-yl)picolinamide | | |
| P-032 | | N-(2-cyanopropan-2-yl)-6-(2-(1-methyl-1H-imidazol-4-yl)-1H-pyrrolo[2,3-b]pyridin-5-yl)picolinamide | | |

TABLE I-continued

| Number | Compound | Name | M − H | M + H |
|---|---|---|---|---|
| P-033 | | 4-chloro-N-(2-cyanopropan-2-yl)-6-(2-(1-(difluoromethyl)-1H-pyrazol-4-yl)-1H-pyrrolo[2,3-b]pyridin-5-yl)picolinamide | | |
| P-034 | | N-(2-cyanopropan-2-yl)-6-(2-(1-(difluoromethyl)-1H-pyrazol-4-yl)-1H-pyrrolo[2,3-b]pyridin-5-yl)-4-methylpicolinamide | | |
| P-035 | | N-(2-cyanopropan-2-yl)-6-(2-(2-methylthiazol-4-yl)-1H-pyrrolo[2,3-b]pyridin-5-yl)picolinamide | | |
| P-036 | | N-(2-cyanopropan-2-yl)-6-(2-(2-methylthiazol-5-yl)-1H-pyrrolo[2,3-b]pyridin-5-yl)picolinamide | | |

TABLE I-continued

| Number | Compound | Name | M − H | M + H |
|---|---|---|---|---|
| P-037 | | N-(2-cyanopropan-2-yl-1,1,1,3,3,3-d6)-6-(2-(1-(difluoromethyl)-1H-pyrazol-4-yl)-1H-pyrrolo[2,3-b]pyridin-5-yl)picolinamide | | |

Embodiment 16(a) of this disclosure relate to one or more of P-001, P-003, P-004, P-005, P-006, P-007, P-008, P-009, P-010, P-011, P-012, P-013, P-014, P-015, P-016, P-017, P-018, P-019, P-021, or P-024 in Embodiment 16.

Embodiment 17 of this disclosure relates to a pharmaceutical composition comprising a compound according to any one of Embodiments 1 to 16, or a pharmaceutically acceptable salt, deuterated analog, a tautomer or an isomer thereof, and a pharmaceutically acceptable carrier.

Embodiment 18 of this disclosure relates to a pharmaceutical composition of Embodiment 17, further comprising a second pharmaceutical agent selected from: an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, pipo-sulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an antibody therapy agent selected from alemtuzumab, bevacizumab, cetuximab, galiximab, gemtuzumab, nivolumab, ipilimumab, panitumumab, pembrolizumab, pertuzumab, rituximab, tositumomab, trastuzumab, and 90 Y ibritumomab tiuxetan; v) a hormone or hormone antagonist selected from the group consisting of anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystauro-sporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor; xv) a Mek inhibitor; xvi) a tyrosine kinase inhibitor; xvii) an EGFR inhibitor; and xviii) an anti-retroviral agent selected from entry inhibitors, fusion inhibitors, reverse transcriptase inhibitors, nucleoside/nucleotide reverse transcriptase inhibitors, non-nucleoside reverse transcriptase inhibitors, integrase inhibitors, protease inhibitors, and multi-class combination products.

Embodiment 19(a) of this disclosure relates to a method for treating a subject with a disease or condition mediated by a TGF-β receptor type 2 (TGF-β2), said method comprising administering to the subject an effective amount of a compound of any one of Embodiments 1 to 16, or a pharmaceutically acceptable salt, deuterated analog, a tautomer or an isomer thereof, or a pharmaceutical composition according to any one of Embodiments 17-18, wherein the disease or condition is fibrosis, cardiovascular disease or cancer. Embodiment 19(b) of this disclosure relates to a method for treating a subject with a disease or condition mediated by a FLT3 mutated kinase, said method comprising administering to the subject an effective amount of a compound of any one of Embodiments 1 to 16, or a pharmaceutically acceptable salt, deuterated analog, a tautomer or an isomer thereof, or a pharmaceutical composition according to any one of Embodiments 17-18, wherein the disease or condition is fibrosis, cardiovascular disease or cancer. Embodiment 19(c) of this disclosure relates to a method for treating a subject with a disease or condition mediated by a TGF-β receptor type 2 (TGF-β2) or a FLT3 mutated kinase, said method comprising administering to the subject an effective amount of a compound of any one of Embodiments 1 to 16, or a pharmaceutically acceptable salt, deuterated analog, a tautomer or an isomer thereof, or a pharmaceutical composition according to any one of Embodiments 17-18, wherein the disease or condition is fibrosis, cardiovascular disease or cancer. In a sub-embodiment of Embodiment 19(a), (b), or (c), the cancer is breast cancer, pancreatic cancer, hepatocellular carcinoma or bladder cancer. In another sub-embodiment of Embodiment 19(a), (b), or (c), the cancer treatment is cancer immunotherapy by TGF-β receptor type 2 inhibition.

III. Binding Assays

The methods of the present disclosure can involve assays that are able to detect the binding of compounds to a target molecule. Such binding is at a statistically significant level, with a confidence level of at least 90%, or at least 95, 97, 98, 99% or greater confidence level that the assay signal represents binding to the target molecule, i.e., is distinguished from background. In some embodiments, controls are used to distinguish target binding from non-specific binding. A large variety of assays indicative of binding are known for different target types and can be used for this disclosure.

Binding compounds can be characterized by their effect on the activity of the target molecule. Thus, a "low activity" compound has an inhibitory concentration ($IC_{50}$) or effective concentration ($EC_{50}$) of greater than 1 µM under standard conditions. By "very low activity" is meant an $IC_{50}$ or $EC_{50}$ of above 100 µM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 µM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ or $EC_{50}$ is defined as the concentration of compound at which 50% of the activity of the target molecule (e.g. enzyme or other protein) activity being measured is lost or gained relative to the range of activity observed when no compound is present. Activity can be measured using methods known to those of ordinary skill in the art, e.g., by measuring any detectable product or signal produced by occurrence of an enzymatic reaction, or other activity by a protein being measured.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., (2000) BIAcore® analysis to test phosphopeptide-SH2 domain interactions, Methods in Molecular Biology. 121:313-21; Liparoto et al., (1999) Biosensor analysis of the interleukin-2 receptor complex, Journal of Molecular Recognition. 12:316-21; Lipschultz et al., (2000) Experimental design for analysis of complex kinetics using surface plasmon resonance, Methods. 20(3): 310-8; Malmqvist., (1999) BIACORE: an affinity biosensor system for characterization of biomolecular interactions, Biochemical Society Transactions 27:335-40; Alfthan, (1998) Surface plasmon resonance biosensors as a tool in antibody engineering, Biosensors & Bioelectronics. 13:653-63; Fivash et al., (1998) BIAcore for macromolecular interaction, Current Opinion in Biotechnology. 9:97-101; Price et al.; (1998) Summary report on the ISOBM TD-4 Workshop: analysis of 56 monoclonal antibodies against the MUC1 mucin. Tumour Biology 19 Suppl 1:1-20; Malmqvist et al, (1997) Biomolecular interaction analysis: affinity biosensor technologies for functional analysis of proteins, Current Opinion in Chemical Biology. 1:378-83; O'Shannessy et al., (1996) Interpretation of deviations from pseudo-first-order kinetic behavior in the characterization of ligand binding by biosensor technology, Analytical Biochemistry. 236:275-83; Malmborg et al., (1995) BIAcore as a tool in antibody engineering, Journal of Immunological Methods. 183:7-13; Van Regenmortel, (1994) Use of biosensors to characterize recombinant proteins, Developments in Biological Standardization. 83:143-51; and O'Shannessy, (1994) Determination of kinetic rate and equilibrium binding constants for macromolecular interactions: a critique of the surface plasmon resonance literature, Current Opinions in Biotechnology. 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g. by ligand binding to the bound protein) a shift occurs in the resonance angle. This angle shift can be measured and is expressed as resonance units (RUs) such that 1000 RUs is equivalent to a change in surface protein concentration of 1 $ng/mm^2$. These changes are displayed with respect to time along the y-axis of a sensorgram, which depicts the association and dissociation of any biological reaction.

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator.

Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., (1972) The Chemist's Companion: A Handbook Of Practical Data, Techniques, And References, John Wiley and Sons, N.Y., Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., (1987) Spectrophotometry and Spectrofluorometry: A Practical Approach, pp. 91-114, IRL Press Ltd.; and Bell, (1981) Spectroscopy In Biochemistry, Vol. I, pp. 155-194, CRC Press.

In spectrofluorometric methods, enzymes are exposed to substrates that change their intrinsic fluorescence when processed by the target enzyme. Typically, the substrate is nonfluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owicki et al., (1997), Application of Fluorescence Polarization Assays in High-Throughput Screening, Genetic Engineering News, 17:27.

FP is particularly desirable since its readout is independent of the emission intensity (Checovich, W. J., et al., (1995) Nature 375:254-256; Dandliker, W. B., et al., (1981) Methods in Enzymology 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., (2000) Development of high throughput screening assays using fluorescence polarization: nuclear receptor-ligand-binding and kinase/phosphatase assays, J Biomol Screen 5:77-88.

Fluorophores derived from sphingolipids that may be used in FP assays are commercially available. For example, Molecular Probes (Eugene, Oreg.) currently sells sphingomyelin and one ceramide flurophores. These are, respectively, N-(4,4-difluoro-5,7-dimethyl-4-bora-3a,4a-diaza-s-indacene-3-pentanoyl)sphingosyl phosphocholine (BODIPY® FL $C_5$-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL $C_5$-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan AG, Hombrechtikon, Switzerland). General multi-well plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., (1996) Curr. Biol. 6:178-182; Mitra et al., (1996) Gene 173:13-17; and Selvin et al., (1995) Meth. Enzymol. 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule.

SPA is widely used in the pharmaceutical industry and has been described (Hanselman et al., (1997) J. Lipid Res. 38:2365-2373; Kahl et al., (1996) Anal. Biochem. 243:282-283; Undenfriend et al., (1987) Anal. Biochem. 161:494-500). See also U.S. Pat. Nos. 4,626,513 and 4,568,649, and European Patent No. 0,154,734. One commercially available system uses FLASHPLATE® scintillant-coated plates (NEN Life Science Products, Boston, Mass.).

The target molecule can be bound to the scintillator plates by a variety of well known means. Scintillant plates are available that are derivatized to bind to fusion proteins such as GST, His6 or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) Anal. Biochem. 257:112-119).

IV. Activity Assays

A number of different assays for TGFRB2 activity can be utilized for assaying for active modulators and/or determining specificity of a modulator for TGFRB2 or other related TGF-β family members. In addition to the assay mentioned in the Examples below, one of ordinary skill in the art will know of other assays that can be utilized and can modify an assay for a particular application. For example, numerous papers concerning TGF-β receptors described assays that can be used. A number of different assays for FLT3 kinase activity can be utilized for assaying for active modulators and/or determining specificity of a modulator for a this particular kinase or group or kinases. In addition to the assay mentioned in the Examples below, one of ordinary skill in the art will know of other assays that can be utilized and can modify an assay for a particular application. For example, numerous papers concerning kinases described assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phospho-specific antibody.

V. Compound Forms and Derivatives (a) Isomers, Prodrugs, and Active Metabolites Compounds contemplated herein are described with reference to both generic Formulae and specific compounds. In addition, the compounds described herein may exist in a number of different forms or derivatives, all within the scope of the present disclosure. These include, for example, tautomers, stereoisomers, racemic mixtures, regioisomers, salts, prodrugs (e.g. carboxylic acid esters), solvated forms, different crystal forms or polymorphs, and active metabolites.

(b) Tautomers, Stereoisomers, Regioisomers, and Solvated Forms

It is understood that some compounds may exhibit tautomerism. In such cases, the Formulae provided herein expressly depict only one of the possible tautomeric forms. It is therefore to be understood that the Formulae provided herein are intended to represent any tautomeric form of the depicted compounds and are not to be limited merely to the specific tautomeric form depicted by the drawings of the Formulae.

Likewise, some of the compounds according to the present disclosure may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present disclosure. Unless specified to the contrary, all such stereoisomeric forms are included within the Formulae provided herein.

In some embodiments, a chiral compound of the present disclosure is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form.

For compounds in which synthesis involves addition of a single group at a double bond, particularly a carbon-carbon double bond, the addition may occur at either of the double bond-linked atoms. For such compounds, the present disclosure includes both such regioisomers.

(c) Prodrugs and Metabolites

In addition to the present Formulae and compounds described herein, the disclosure also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more of advantageous handling, administration, and/or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound.

In this context, a common example of a prodrug is an alkyl ester of a carboxylic acid. Relative to compounds o this disclosure, further examples include, without limitation, an amide or carbamate derivative at the pyrrole nitrogen (i.e. Ni) of the azaindole core.

As described in The Practice of Medicinal Chemistry, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

Oxidative reactions: Oxidative reactions are exemplified without limitation to reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative 0- and S-dealkylation, oxidative deamination, as well as other oxidative reactions.

Reductive reactions: Reductive reactions are exemplified without limitation to reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 2004/0077595, incorporated herein by reference.) Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g. stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Prodrugs may proceed from prodrug form to active form in a single step or may have one or more intermediate forms which may themselves have activity or may be inactive.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic process in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques known in the art. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth, supra.

(d) Pharmaceutically Acceptable Salts

Compounds can be formulated as or be in the form of pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, 19th ed., Mack Publishing Co., Easton, Pa., Vol. 2, p. 1457, 1995. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

Thus, for example, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as L-glycine, L-lysine, and L-arginine, ammonia, primary, secondary, and tertiary amines, and cyclic amines, such as hydroxyethylpyrrolidine, piperidine, morpholine or piperazine, and inorganic salts derived from sodium, calcium, potassium, magnesium, manganese, iron, copper, zinc, aluminum and lithium.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Unless specified to the contrary, specification of a compound herein includes pharmaceutically acceptable salts of such compound.

(e) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present disclosure and specified Formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds of the disclosure are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the disclosure with the acid or base, an amorphous complex is formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the Formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

VI. Formulations and Administration

The methods and compounds will typically be used in therapy for human subjects. However, they may also be used to treat similar or identical indications in other animal subjects. In this context, the terms "subject," "animal subject," and the like refer to human and non-human vertebrates, e.g. mammals, such as non-human primates, sports and commercial animals, e.g., equines, bovines, porcines, ovines, rodents, and pets, e.g., canines and felines.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in The Science and Practice of Pharmacy, 21$^{st}$ edition, Lippincott, Williams and Wilkins, Philadelphia, Pa., 2005 (hereby incorporated by reference herein).

Carriers or excipients can be used to produce compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, transdermal, or inhalant. In some embodiments, the compounds can be administered by oral administration. For oral administration, for example, the compounds can be formulated into conventional oral dosage forms such as capsules, tablets, and liquid preparations such as syrups, elixirs, and concentrated drops.

For inhalants, compounds of the disclosure may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of the disclosure may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, poly-vinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the disclosure are formulated in sterile liquid solutions, such as in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions of this disclosure are formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In another embodiment, the carriers are those in which the active ingredient is soluble. Emulsifiers, stabilizers, humectants and antioxidants may also be included as well as agents imparting color or fragrance, if desired. Creams for topical application are formulated from a mixture of mineral oil, self-emulsifying beeswax and water in which mixture the active ingredient, dissolved in a small amount solvent (e.g. an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

The amounts of various compounds to be administered can be determined by standard procedures taking into account factors such as the compound $IC_{50}$, the biological half-life of the compound, the age, size, and weight of the subject, and the indication being treated. The importance of these and other factors are well known to those of ordinary skill in the art. Generally, a dose will be between about 0.01 and 50 mg/kg, or 0.1 and 20 mg/kg of the subject being treated. Multiple doses may be used.

The compounds of the disclosure may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the disclosure or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of the present disclosure, or at the same time as a compound of the disclosure. Use in combination also includes use with a therapy or medical procedure that is administered once or infrequently, such as surgery, along with a compound of the disclosure administered within a short time or longer time before or after the other therapy or procedure. In some embodiments, the present disclosure provides for delivery of compounds of the disclosure and one or more other drug therapeutics delivered by a different route of administration or by the same route of administration. The use in combination for any route of administration includes delivery of compounds of the disclosure and one or more other drug therapeutics delivered by the same route of administration together in any formulation, including formulations where the two compounds are chemically linked in such a way that they maintain their therapeutic activity when administered. In one embodiment, the other drug therapy may be co-administered with one or more compounds of the disclosure. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of compounds of the disclosure and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

In certain embodiments, the patient is 60 years or older and relapsed after a first line cancer therapy. In certain embodiments, the patient is 18 years or older and is relapsed or refractory after a second line cancer therapy. In certain embodiments, the patient is 60 years or older and is primary refractory to a first line cancer therapy. In certain embodiments, the patient is 70 years or older and is previously untreated. In certain embodiments, the patient is 70 years or older and is ineligible and/or unlikely to benefit from cancer therapy.

In certain embodiments, the therapeutically effective amount used in the methods provided herein is at least 10 mg per day of a compound of having any of the Formulae described in this disclosure, including any one of the compounds listed in Table I, or a pharmaceutically acceptable salt, a solvate, a tautomer, an isomer or a deuterated analog of any of these compounds. In certain embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500 mg per dosage. In other embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day or more. In certain embodiments, the compound is administered continuously. In certain embodiments, the compound is administered in one or more dosages daily (such as once daily, twice daily, three times daily, four times daily, and the like) or weekly (such as once weekly, twice weekly, three times weekly, four times weekly, and the like).

In certain embodiments, provided herein is a method for treating a disease or condition mediated by TGFBR2 by administering to a mammal having a disease or condition at least 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day of a compound of having any of the Formulae described in this disclosure, including any one of the compounds listed in Table I, or a pharmaceutically acceptable salt, a solvate, a tautomer, an isomer or a deuterated analog of any of these compounds, and wherein the compound is administered on an empty stomach. In certain embodiments, provided herein is a method for treating a disease or condition mediated by a FLT3 mutated kinase by administering to a mammal having a disease or condition at least 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day of a compound of having any of the Formulae described in this disclosure, including any one of the compounds listed in Table I, or a pharmaceutically acceptable salt, a solvate, a tautomer, an isomer or a deuterated analog of any of these compounds, and wherein the compound is administered on an empty stomach.

VII. Methods for Treating Conditions Mediated by TGFBR2 or FLT3

It is contemplated that dysregulation of TGF-β signaling pathways may impact many disease states. For example, TGF-β isoforms (TGF-β1, TGF-β2, and TGF-β3) are critical to the regulation of inflammation in lungs and other organ systems, and thus TGF-β plays a central role in inhibiting inflammation and autoimmune disease. Interestingly, TGF-β exhibits potent antiproliferative effects in many cell types while promoting proliferation in other cell types. Additionally, TGF-β regulates extracellular matrix production and remodeling, and thus dysregulation of these systems may lead to significant pathological effects on lung development as well as the pathogenesis of pulmonary diseases. Non-limiting examples of such pulmonary diseases include pulmonary fibrosis, chronic obstructive pulmonary disease (COPD), and pulmonary vascular disease. Downstream pathological effects of the TGF-β signaling cascade in pulmonary fibrosis, pulmonary artierla hypertension, COPD, and asthma are described in Aschner et al., Am. J. Respir. Cell Mol. Biol., 54(5):647-44 (2016).

Administration of inhibitors of TGF-β receptor kinases may be useful in inhibiting TGF-1 and thus such inhibitors may be useful as therapeutic agents for the treatment of various disease states. For example, it has been found that TGFBR2 inhibitors, such as ITD-1, may be valuable for treating diseases associated with pathological processes such as cancer, fibrosis, or cardiovascular disease (including adult cardiovascular disease) (Willems et al., *Cell Stem Cell*, 11(2): 242-252 (2012)). It has also been found that neutralizing TGFBR2 has potent antimetastatic activity and inhibits pancreatic cancer (Ostapoff et al., *Cancer Res;* 74(18); 4996-5007 (2014)). It has been further found that inhibition of TGFBR2 can inhibit hepatocellular carcinoma (HCC) progression (Dituri et al., PLOS ONE, 8(6):e67109 (2013); Rojas et al., Neoplasia, 18(6) 371-386 (2016)). TGFBR2 is also highly expressed in breast cancer cells; thus TGFBR2 inhibitors, may inhibit breast cancer cell proliferation (Gao et al., PLOS ONE, 10(11):e0141412 (2015)). It has been further found that ablation of TGF-β signaling can suppress bladder cancer progression (Liang et al., Scientific Reports, 6:29479 (2016)). TGF-β ligands and receptors have potent immunosuppressive activity on T-cells and NK cells, and TGF-β antagonists can significantly suppress tumorigenesis and greatly improve the efficacy of immunodulatory chemotheraphy in preclinical models (Isama Therapeutics, "TGF-β: A Prime Target for Cancer Immunotherapy (CIMT Satellite Symposium)," http://www.isama-therapeutics.com/fileadmin/user upload/documents/CIMT_Isarna_Satellite_Symposium_Booklet_2014.pdf, May 7, 2014).

In another embodiment, the present disclosure provides a method for treating a subject suffering from or at risk of TGFBR2 mediated diseases or conditions. The method includes administering to the subject an effective amount of one or more compound having any of the Formulae described in this disclosure, including any one of the compounds listed in Table I, or a pharmaceutically acceptable salt, a solvate, a tautomer, an isomer or a deuterated analog of any of these compounds, or a pharmaceutical composition thereof. In certain embodiments, the method involves administering to the subject an effective amount of any one or more compound(s) as described herein in combination with one or more other therapies for the disease or condition. Non-limiting examples of a disease or condition mediated by TGFBR2 include cancer, fibrosis, cardiovascular disease, or lung disease.

In another embodiment, the present disclosure provides a method for treating a subject suffering from or at risk of disease or condition mediated by a FLT3 mutated kinase. The method includes administering to the subject an effective amount of one or more compound having any of the Formulae described in this disclosure, including any one of the compounds listed in Table I, or a pharmaceutically acceptable salt, a solvate, a tautomer, an isomer or a deuterated analog of any of these compounds, or a pharmaceutical composition thereof. In certain embodiments, the method involves administering to the subject an effective amount of any one or more compound(s) as described herein in combination with one or more other therapies for the disease or condition. Non-limiting examples of a disease or condition mediated by a FLT3 mutated kinase include cancer, fibrosis, cardiovascular disease, or lung disease.

In some embodiments, the cancer is pancreatic cancer, hepatocellular carcinoma, breast cancer, bladder cancer, colon cancer, or ovarian cancer. In some embodiments, the cancer is pancreatic cancer, hepatocellular carcinoma, breast cancer, or bladder cancer. In some embodiments, the cancer is acute myeloid leukemia ("AML").

In some embodiments, the fibrosis is pulmonary fibrosis, radiation-induced lung injury following treatment for cancer, cirrhosis, atrial fibrosis, endomycardial fibrosis, myocardial infarction, glial scar, arterial stiffness, arthrofibrosis, Crohn's disease, Dupuytren's contracture, ekloid, medistinal fibrosis, myelofibrosis, Peyronie's disease, Nephrogenic systemic fibrosis, Progressive massive fibrosis, Retroperitoneal fibrosis, schleroderma/systemic sclerosis, or adhesive capsulities.

In some embodiments, the cardiovascular disease is heart and blood vessel disease, heart failure, arrhythmia, and heart valve problems.

In some embodiments, the lung disease is pulmonary fibrosis, pulmonary arterial hypertension, COPD, or asthma.

In one aspect, the disclosure provides a method for treating a disease or condition in a subject in need thereof, by administering to the subject a therapeutically effective amount of any one or more compound(s) as described herein, a prodrug of such compound, a pharmaceutically acceptable salt of such compound or prodrug, or a pharmaceutically acceptable formulation of such compound or prodrug. The compound can be alone or can be part of a composition. In one embodiment, the disclosure provides a method of treating a disease or condition in a subject in need thereof, by administering to the subject a therapeutically effective amount of any one or more compound(s) as described herein, a prodrug of such compound, a pharmaceutically acceptable salt of such compound or prodrug, or a pharmaceutically acceptable formulation of such compound or prodrug in combination with one or more other suitable therapies for the disease or condition.

In aspects and embodiments involving treatment of a disease or condition with one or more of the compounds described herein, the disclosure provides methods for treating a disease or condition mediated by TGFBR2 in a subject in need thereof (e.g. a mammal such as a human, other primates, sports animals, animals of commercial interest such as cattle, farm animals such as horses, or pets such as dogs and cats), e.g., a disease or condition characterized by abnormal TGFBR2 activity. In some embodiments, the methods may involve administering to the subject suffering from or at risk of a disease or condition mediated by TGFBR2 an effective amount of one or more compound(s) as described herein. In aspects and embodiments involving treatment of a disease or condition with one or more of the compounds described herein, the disclosure provides methods for treating a disease or condition mediated by a FLT3 mutated kinase in a subject in need thereof (e.g. a mammal such as a human, other primates, sports animals, animals of commercial interest such as cattle, farm animals such as horses, or pets such as dogs and cats), e.g., a disease or condition characterized by abnormal FLT3 activity. In some embodiments, the methods may involve administering to the subject suffering from or at risk of a disease or condition mediated by a FLT3 mutated kinase an effective amount of one or more compound(s) as described herein. In some embodiments, a "FLT3 mutated kinase" is a FLT3 kinase having one or more mutations as described herein.

In certain embodiments, the present disclosure provides use of one or more compounds having any of the Formulae described in this disclosure, including any one of the compounds listed in Table I, or a pharmaceutically acceptable salt, a solvate, a tautomer, an isomer or a deuterated analog of any of these compounds, or a pharmaceutical composition thereof, in the manufacture of a medicament for the treatment of a disease or condition as described herein. In other embodiments, the present disclosure provides a compound having any of the Formulae described in this disclosure, including any one of the compounds listed in Table I, or a pharmaceutically acceptable salt, a solvate, a tautomer, an isomer or a deuterated analog of any of these compounds, or a composition comprising a compound having any of the Formulae described in this disclosure, including any one of the compounds listed in Table I, or a pharmaceutically acceptable salt, a solvate, a tautomer, an isomer or a deuterated analog of any of these compounds for use in treating a disease or condition as described herein.

VIII. Combination Therapy

Protein kinase modulators may be usefully combined with another pharmacologically active compound, or with two or more other pharmacologically active compounds, particularly in the treatment of cancer. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In some embodiments, the present disclosure provides a composition comprising one or more compounds having any of the Formulae described in this disclosure, including any one of the compounds listed in Table I, or a pharmaceutically acceptable salt, a solvate, a tautomer, an isomer or a deuterated analog of any of these compounds, or a pharmaceutical composition thereof, and one or more agents. In some embodiments, the one or more agents are selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustinc, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, and vidarabine; an immunotherapy, including, but not limited to, alemtuzumab, bevacizumab, cetuximab, galiximab, gemtuzumab, panitumumab, pertuzumab, rituximab, tositumomab, trastuzumab, 90 Y ibritumomab tiuxetan, ipilimumab, and tremelimumab; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and testaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-.alpha., and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. tanespimycin) and famesyltransferase inhibitors (e.g. tipifamib); MEK inhibitors (e.g., AS703026, AZD6244 (selumetinib), AZD8330, BIX02188, C11040 (PD184352), D-87503, GSK1120212 (JTP-74057), PD0325901, PD318088, PD98059, PDEA119 (BAY 869766), TAK-733).

In another embodiment, each method provided herein may further comprise administering a second therapeutic agent. In certain embodiments, the second therapeutic agent is an anticancer agent. In certain embodiments, the second therapeutic agent is a protein kinase inhibitor. In certain embodiments, a tyrosine kinase inhibitor; and in yet another embodiment, a FLT3 kinase inhibitor, including, but not limiting to, Sunitinib, Cediranib, XL-184 free base (Cabozantinib, Ponatinib (AP24534), PHA-665752, Dovitinib (TKI258, CHIR-258), AC220 (Quizartinib), TG101209, KW-2449, AEE788 (NVP-AEE788), MP-470 (Amuvatinib), TSU-68 (SU6668, Orantinib, ENMD-2076, Vatalanib dihydrochloride (PTK787) and Tandutinib (MLN518).

In another embodiment, the present disclosure provides a method of treating a cancer in a subject in need thereof by administering to the subject an effective amount of a composition including any one or more compound(s) as described herein in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, .gamma.-ray, or electron, proton, neutron, or .alpha. particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexatin lutetium), surgery, or bone marrow and stem cell transplantation.

IX. Kits

In another embodiment, the present disclosure provides kits that include one or more compounds having any of the Formulae described in this disclosure, including any one of the compounds listed in Table I, or a pharmaceutically acceptable salt, a solvate, a tautomer, an isomer or a deuterated analog of any of these compounds, or a pharmaceutical composition thereof. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the kits described herein may include written instructions for use and/or other indication that the compound or composition is suitable or approved for administration to a mammal, e.g., a human, for a protein kinase-mediated disease or condition; and the compound or composition may be packaged in unit dose or single dose form, e.g., single dose pills, capsules, or the like.

X. Manipulation of TGFBR2 or FLT3

Techniques for the manipulation of nucleic acids, such as, e.g., subcloning, labeling probes (e.g. random-primer labeling using Klenow polymerase, nick translation, amplification), sequencing, hybridization and the like are well described in the scientific and patent literature, see, e.g., Sambrook, ed., Molecular Cloning: a Laboratory Manual (2nd ed.), Vols. 1-3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I. Theory and Nucleic Acid Preparation, Tijssen, ed. Elsevier, N.Y. (1993).

Nucleic acid sequences can be amplified as necessary for further use using amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4): 852-6, 858, 860 passim.

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis (e.g. SDS-PAGE), nucleic acid or target or signal amplification methods, radiolabeling, scintillation counting, and affinity chromatography.

Obtaining and manipulating nucleic acids used to practice the methods of the disclosure can be performed by cloning from genomic samples, and, if desired, screening and re-cloning inserts isolated or amplified from, e.g., genomic clones or cDNA clones. Sources of nucleic acid used in the methods of the present disclosure include genomic or cDNA libraries contained in, e.g., mammalian artificial chromosomes (MACs), see, e.g., U.S. Pat. Nos. 5,721,118; 6,025, 155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The nucleic acids used to practice the methods of the present disclosure can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The nucleic acids used to practice the methods of the present disclosure can also be provided in expression vectors and cloning vehicles, e.g., sequences encoding the polypeptides used to practice the methods of the present disclosure. Expression vectors and cloning vehicles used to practice the methods of the present disclosure can comprise viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors used to practice the methods of the present disclosure can include chromosomal, non-chromosomal and synthetic DNA sequences. Large numbers of suitable vectors are known to those of skill in the art, and are commercially available.

The nucleic acids used to practice the methods of the present disclosure can be cloned, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" a PCR primer pair. Vectors may be introduced into a genome or into the cytoplasm or a nucleus of a cell and expressed by a variety of conventional techniques, well described in the scientific and patent literature. See, e.g., Roberts (1987) Nature 328:731; Schneider (1995) Protein Expr. Purif. 6435:10; Sambrook, Tijssen or Ausubel. The vectors can be isolated from natural sources, obtained from such sources as ATCC or GenBank libraries, or prepared by synthetic or recombinant methods. For example, the nucleic acids used to practice the methods of the present disclosure can be expressed in expression cassettes, vectors or viruses which are stably or transiently expressed in cells (e.g. episomal expression systems). Selection markers can be incorporated into expression cassettes and vectors to confer a selectable phenotype on transformed cells and sequences. For example, selection markers can code for episomal maintenance and replication such that integration into the host genome is not required.

In one embodiment, the nucleic acids used to practice the methods of the present disclosure are administered in vivo for in situ expression of the peptides or polypeptides used to practice the methods of the disclosure. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, selected from baculoviridiae, parvoviridiae, picornoviridiae, herpesveridiae, poxviridae, adenoviridiae, or picornnaviridiae. Chimeric vectors may also be employed which exploit advantageous merits of each of the parent vector properties (See e.g., Feng (1997) Nature Biotechnology 15:866-870). Such viral genomes may be modified by recombinant DNA techniques to include the nucleic acids used to practice the methods of the present disclosure; and may be further engineered to be replication deficient, conditionally replicating or replication competent. In alternative embodiments, vectors are derived from the adenoviral (e.g. replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher (1992) J. Virol. 66:2731-2739; Johann (1992) J. Virol. 66:1635-1640). Adeno-associated virus (AAV)-based vectors can be used to transduce cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada (1996) Gene Ther. 3:957-964.

The present disclosure also relates to use of fusion proteins, and nucleic acids encoding them. A polypeptide used to practice the methods of the present disclosure can be fused to a heterologous peptide or polypeptide, such as N-terminal identification peptides which impart desired characteristics, such as increased stability or simplified purification. Peptides and polypeptides used to practice the methods of the present disclosure can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. In one embodiment, a nucleic acid encoding a polypeptide used to practice the methods of the present disclosure is assembled in appropriate phase with a leader sequence capable of directing secretion of the translated polypeptide or fragment thereof. Technology pertaining to vectors encoding fusion proteins and application of fusion proteins are well described in the scientific and patent literature, see e.g., Kroll (1993) DNA Cell. Biol. 12:441-53.

The nucleic acids and polypeptides used to practice the methods of the present disclosure can be bound to a solid support, e.g., for use in screening and diagnostic methods. Solid supports can include, e.g., membranes (e.g. nitrocellulose or nylon), a microtiter dish (e.g. PVC, polypropylene, or polystyrene), a test tube (glass or plastic), a dip stick (e.g. glass, PVC, polypropylene, polystyrene, latex and the like), a microfuge tube, or a glass, silica, plastic, metallic or polymer bead or other substrate such as paper. One solid support uses a metal (e.g. cobalt or nickel)-comprising column which binds with specificity to a histidine tag engineered onto a peptide.

Adhesion of molecules to a solid support can be direct (i.e., the molecule contacts the solid support) or indirect (a "linker" is bound to the support and the molecule of interest binds to this linker). Molecules can be immobilized either covalently (e.g. utilizing single reactive thiol groups of cysteine residues (see, e.g., Colliuod (1993) Bioconjugate Chem. 4:528-536) or non-covalently but specifically (e.g. via immobilized antibodies (see, e.g., Schuhmann (1991) Adv. Mater. 3:388-391; Lu (1995) Anal. Chem. 67:83-87; the biotin/strepavidin system (see, e.g., Iwane (1997) Biophys. Biochem. Res. Comm. 230:76-80); metal chelating, e.g., Langmuir-Blodgett films (see, e.g., Ng (1995) Langmuir 11:4048-55); metal-chelating self-assembled monolayers (see, e.g., Sigal (1996) Anal. Chem. 68:490-497) for binding of polyhistidine fusions.

Indirect binding can be achieved using a variety of linkers which are commercially available. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the cross-linking of sulfhydryl-containing compounds. The spacer can be of varying length and be aliphatic or aromatic. Examples of commercially available homobifunctional cross-linking reagents include, but are not limited to, the imidoesters such as dimethyl adipimidate dihydrochloride (DMA); dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl (4-iodoacetyl)aminobenzoate (SIAB) and the sulfosuccinimidyl derivatives such as sulfosuccinimidyl(4-iodoacetyl) aminobenzoate (sulfo-SIAB) (Pierce). Another group of coupling agents is the heterobifunctional and thiol cleavable agents such as N-succinimidyl 3-(2-pyridyidithio)propionate (SPDP) (Pierce Chemicals, Rockford, Ill.).

Antibodies can also be used for binding polypeptides and peptides used to practice the methods of the present disclosure to a solid support. This can be done directly by binding peptide-specific antibodies to the column or it can be done by creating fusion protein chimeras comprising motif-containing peptides linked to, e.g., a known epitope (e.g. a tag (e.g. FLAG, myc) or an appropriate immunoglobulin constant domain sequence (an "immunoadhesin," see, e.g., Capon (1989) Nature 377:525-531 (1989).

Nucleic acids or polypeptides used to practice the methods of the present disclosure can be immobilized to or applied to an array. Arrays can be used to screen for or monitor libraries of compositions (e.g. small molecules, antibodies, nucleic acids, etc.) for their ability to bind to or modulate the activity of a nucleic acid or a polypeptide used to practice the methods of the present disclosure. For example, in one embodiment of the disclosure, a monitored parameter is transcript expression of a gene comprising a nucleic acid used to practice the methods of the present disclosure. One or more, or all the transcripts of a cell can be measured by hybridization of a sample comprising transcripts of the cell, or nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the present disclosure. Polypeptide arrays" can also be used to simultaneously quantify a plurality of proteins.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface. In practicing the methods of the present disclosure, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent application Nos. 20010018642; 20010019827; 20010016322; 20010014449; 20010014448; 20010012537; 20010008765.

Host Cells and Transformed Cells

The present disclosure also provides a transformed cell comprising a nucleic acid sequence used to practice the methods of the present disclosure, e.g., a sequence encoding a polypeptide used to practice the methods of the present disclosure, or a vector used to practice the methods of the present disclosure. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces,* and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

Vectors may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes used to practice the methods of the present disclosure. Following transformation of a suitable host strain and growth of the host strain to an appropriate cell density, the selected promoter may be induced by appropriate means (e.g. temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides used to practice the methods of the present disclosure may or may not also include an initial methionine amino acid residue.

Cell-free translation systems can also be employed to produce a polypeptide used to practice the methods of the present disclosure. Cell-free translation systems can use mRNAs transcribed from a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in E. coli.

For transient expression in mammalian cells, cDNA encoding a polypeptide of interest may be incorporated into a mammalian expression vector, e.g. pcDNA1, which is available commercially from Invitrogen Corporation (San Diego, Calif., U.S.A.; catalogue number V490-20). This is a multifunctional 4.2 kb plasmid vector designed for cDNA expression in eukaryotic systems, and cDNA analysis in prokaryotes, incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

The cDNA insert may be first released from the above phagemid incorporated at appropriate restriction sites in the pcDNAI polylinker. Sequencing across the junctions may be performed to confirm proper insert orientation in pcDNAI. The resulting plasmid may then be introduced for transient expression into a selected mammalian cell host, for example, the monkey-derived, fibroblast like cells of the COS-1 lineage (available from the American Type Culture Collection, Rockville, Md. as ATCC CRL 1650).

For transient expression of the protein-encoding DNA, for example, COS-1 cells may be transfected with approximately 8 µg DNA per $10^6$ COS cells, by DEAE-mediated DNA transfection and treated with chloroquine according to the procedures described by Sambrook et al, Molecular Cloning: A Laboratory Manual, 1989, Cold Spring Harbor Laboratory Press, Cold Spring Harbor N.Y., pp. 16.30-16.37. An exemplary method is as follows. Briefly, COS-1 cells are plated at a density of $5\times10^6$ cells/dish and then grown for 24 hours in FBS-supplemented DMEM/F12 medium. Medium is then removed and cells are washed in PBS and then in medium. A transfection solution containing DEAE dextran (0.4 mg/mL), 100 µM chloroquine, 10% NuSerum, DNA (0.4 mg/mL) in DMEM/F12 medium is then applied on the cells 10 mL volume. After incubation for 3 hours at 37° C., cells are washed in PBS and medium as just described and then shocked for 1 minute with 10% DMSO in DMEM/F12 medium. Cells are allowed to grow for 2-3 days in 10% FBS-supplemented medium, and at the end of incubation dishes are placed on ice, washed with ice cold PBS and then removed by scraping. Cells are then harvested by centrifugation at 1000 rpm for 10 minutes and the cellular pellet is frozen in liquid nitrogen, for subsequent use in protein expression. Northern blot analysis of a thawed aliquot of frozen cells may be used to confirm expression of receptor-encoding cDNA in cells under storage.

In a like manner, stably transfected cell lines can also prepared, for example, using two different cell types as host: CHO K1 and CHO Pro5. To construct these cell lines, cDNA coding for the relevant protein may be incorporated into the mammalian expression vector pRC/CMV (Invitrogen), which enables stable expression. Insertion at this site places the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

An exemplary protocol to introduce plasmids constructed as described above is as follows. The host CHO cells are first seeded at a density of $5\times10^5$ in 10% FBS-supplemented MEM medium. After growth for 24 hours, fresh medium is added to the plates and three hours later, the cells are transfected using the calcium phosphate-DNA co-precipitation procedure (Sambrook et al, supra). Briefly, 3 µg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/mL). Individual colonies of G418-resistant cells are isolated about 2-3 weeks later, clonally selected and then propagated for assay purposes.

EXAMPLES

The schemes and examples below depict the general synthetic procedure for the compounds described herein. Synthesis of the compounds described herein is not limited by these examples and schemes. One skilled in the art will know that other procedures can be used to synthesize the compounds described herein, and that the procedures described in the examples and schemes is only one such procedure. In the descriptions below, one of ordinary skill in the art would recognize that specific reaction conditions, added reagents, solvents, and reaction temperatures can be modified for the synthesis of specific compounds that fall within the scope of this disclosure.

Unless otherwise specified, intermediate compounds in the examples below, that do not contain a description of how they are made, are either commercially available to one skilled in the art, or can otherwise be synthesized by the skilled artisan using commercially available precursor molecules and knowledge and techniques known in the art. In most cases, alternative techniques can be used. The examples are intended to be illustrative and are not limiting or restrictive to the scope of the disclosure.

General Synthesis

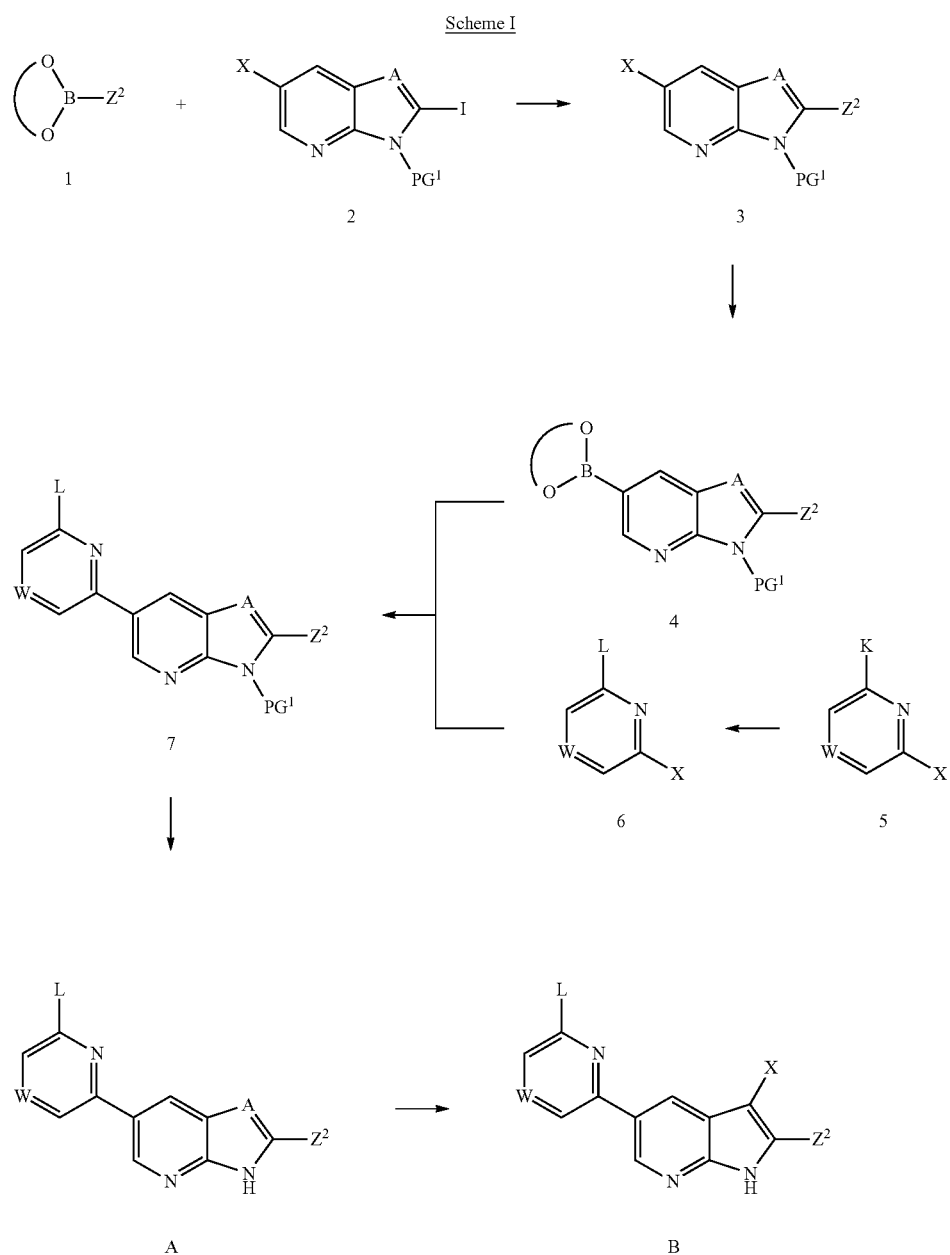

Scheme I provides an exemplary synthesis of a compound of Formula A (wherein A is N or —C($Z^3$)= and $Z^3$ is hydrogen) and a compound of Formula B (wherein X is halo), wherein W, L, and $Z^2$ are as defined herein. Boronic ester 1 and the substituted azaindole 2, wherein $PG^1$ is a protecting group and X is halo, are coupled via standard cross-coupling conditions to produce 3. Compound 3 then undergoes borylation to form boronic ester 4.

Where L is —C(O)$NR^3R^4$, 6 may be formed from 5, wherein K is —$CO_2H$, via coupling with a primary or secondary amine (e.g. via HBTU coupling). Alternatively, where L is —$SO_2NR^6R^7$, K of intermediate 5 may be —$SO_2C_1$. Then, sulfonamide 6 may be formed by coupling the sulfonyl chloride 5 with the appropriate primary or secondary amine. A base, such as pyridine, may be used to facilitate formation of sulfonamide 6. Where L is —NHC(O)$R^4$, 6 may be formed by cross-coupling 5, wherein K is halo or triflate, with the amide $NH_2C(O)R^4$ under standard cross-coupling conditions. Alternatively, wherein K is —$NH_2$, 6 may be formed by reaction of 5 with acid chloride ClC(O)$R^4$ under basic conditions.

Intermediate 4 is then coupled with appropriately functionalized 6 via standard cross-coupling conditions to produce 7. 7 may be deprotected to give a compound of Formula A. A compound of Formula A, wherein A is —C($Z^3$)= and $Z^3$ is hydrogen, can also be halogenated to produce a compound of Formula B (for example, via treatment with 1-chloropyrrolidine-2,5-dione in THF).

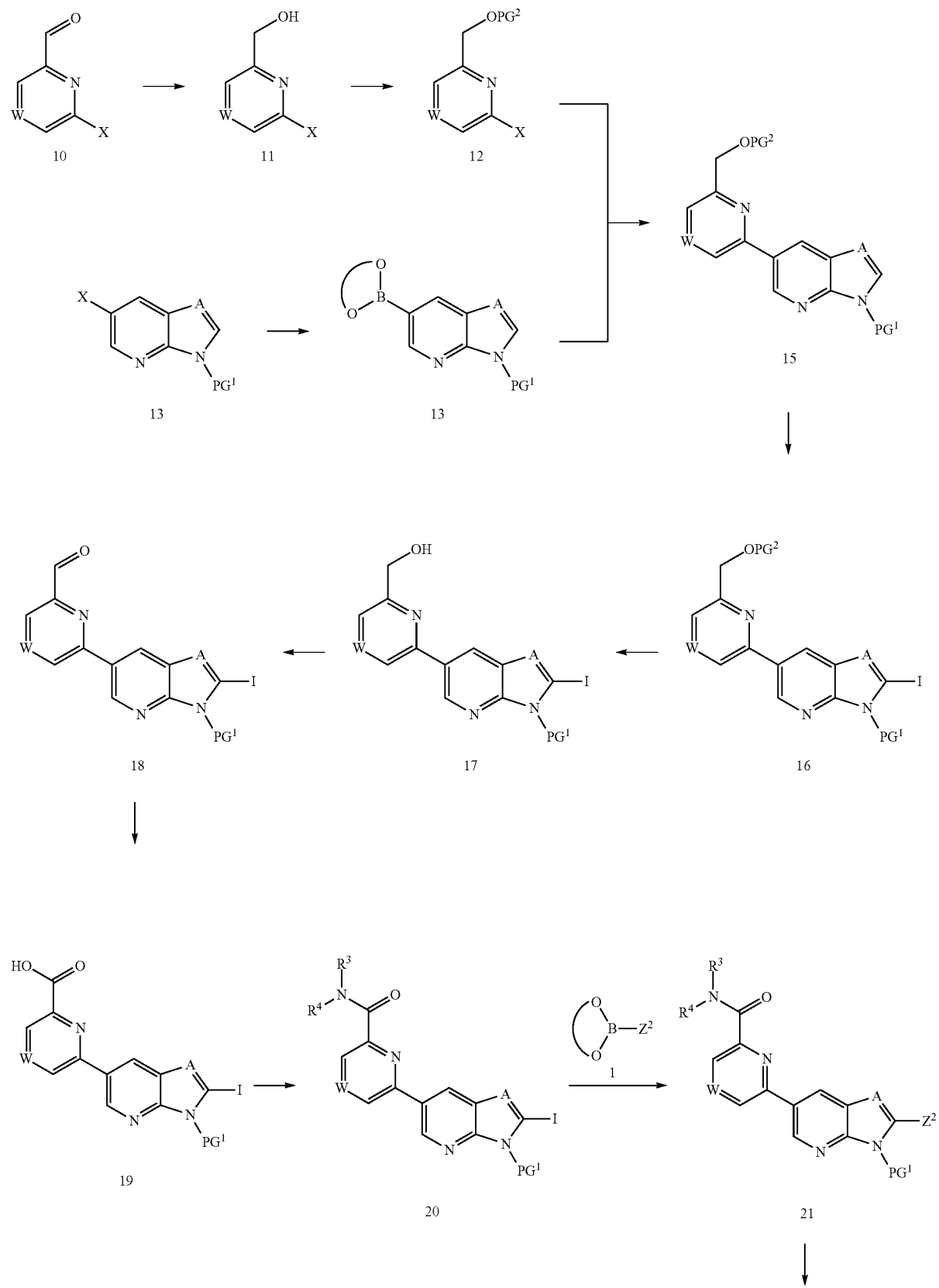
Scheme II

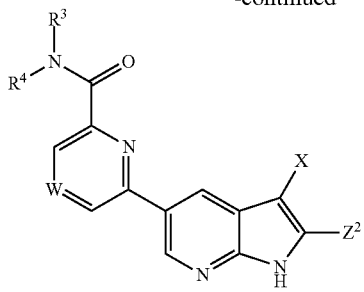

D

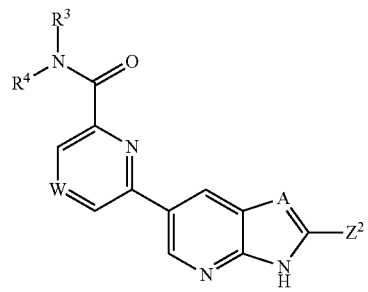

C

Scheme II provides an exemplary method of a compound of Formula C (wherein A is N or —C(Z³)═ and Z³ is hydrogen) and a compound of Formula D (wherein X is halo), wherein W, R³, R⁴, and Z² are as described herein. Aldehyde 10, wherein X is halo, is first reduced to give alcohol 11 (e.g. with sodium borohydride), which is then protected to produce 12, wherein $PG^2$ is a protecting group. Substituted azaindole 13, wherein X is halo and $PG^1$ is a protecting group, undergoes borylation to form boronic ester 14. 12 and 14 then undergo cross-coupling under standard conditions to produce 15, which is then iodinated to give 16. Deprotection of 16 to produce 17 can be accomplished via standard conditions. The alcohol 17 is oxidized to aldehyde 18, and subsequently aldehyde 18 is oxidized to acid 19 with a suitable oxidant, such as oxone monopersulfate. Synthesis of the amide 20 is then accomplished via coupling between acid 19 and a desired amine. 20 then undergoes cross-coupling under standard conditions with boronic ester 1 to afford 21. Deprotection of 21 then gives a compound of Formula C. A compound of Formula C, wherein A is —C(Z³)═ and Z³ is H, can also be halogenated to produce a compound of Formula D (e.g. via treatment with 1-chloropyrrolidine-2,5-dione in THF).

Example 1: N-(2-Cyanopropan-2-yl)-6-(2-(6-methoxypyridin-3-yl)-1H-pyrrolo[2,3-b]pyridin-5-yl)picolinamide, 31(b)

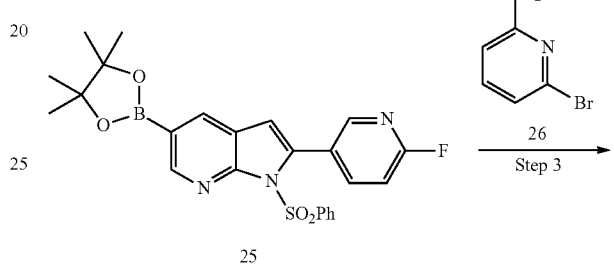

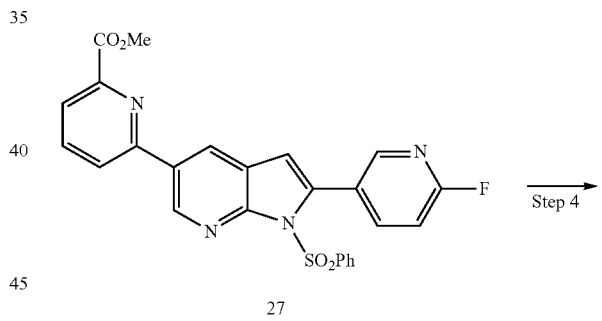

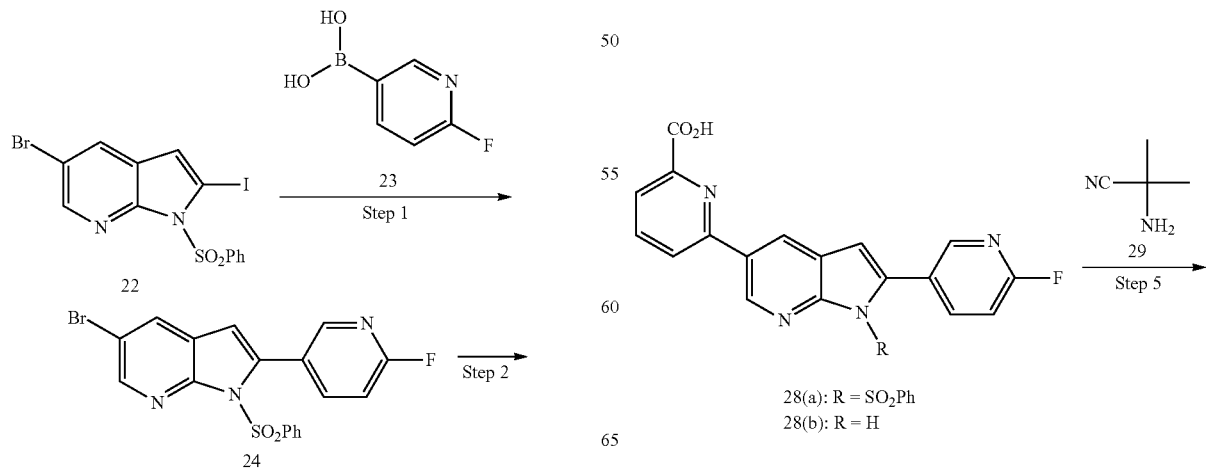

-continued

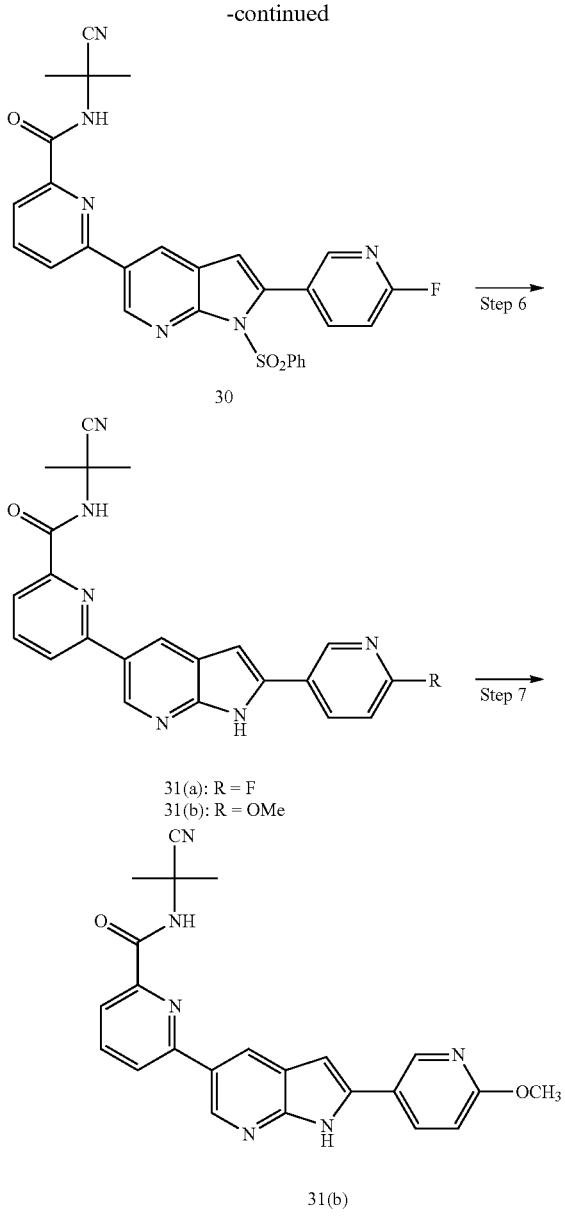

Step 1—Preparation of 5-Bromo-2-(6-fluoropyridin-3-yl)-1-(phenylsulfonyl)-1H-pyrrolo[2,3-b]pyridine (24)

A suspension of compound 22 (30 g, 64.8 mmol, 1 equiv), compound 23 (10 g, 71.3 mmol, 1.1 equiv), potassium carbonate (26.9 g, 194 mmol, 3 equiv) in dioxane (360 mL) and water (72 mL) was sparged with nitrogen for 10 minutes. Tetrakis(triphenylphosphine) palladium(0) (7.49 g, 6.48 mmol, 0.1 equiv) was added and the reaction mixture was refluxed overnight, at which point LC/MS indicated the reaction was complete. The reaction was diluted with ethyl acetate (500 mL) and water (500 mL). The organic layer was separated and concentrated under reduced pressure. The crude product was dissolved in dichloromethane and purified over silica gel (500 g), eluting with a gradient of 0 to 50% ethyl acetate in hexanes. The resulting solid was triturated with MTBE (~200 mL) to give 5-bromo-2-(6-fluoropyridin-3-yl)-1-(phenylsulfonyl)-1H-pyrrolo[2,3-b]pyridine.

Step 2—2-(6-Fluoropyridin-3-yl)-1-(phenylsulfonyl)-5-(4,4,5,5-tetramethyl-1,3,2-dioxaborolan-2-yl)-1H-pyrrolo[2,3-b]pyridine (25)

Potassium acetate (13.62 g, 139 mmol, 3 equiv) and [1,1'-bis(diphenylphosphino)ferrocene] dichloropalladium (II) (3.78 g, 4.63 mmol, 0.1 equiv) were sequentially added to a solution of compound 24 (20 g, 46.3 mmol, 1 equiv) and bis(pinacolato)diboron (14.10 g, 55.5 mmol, 1.2 equiv) in DMF (185 mL). The mixture was heated at 80° C. for 4 hours. After cooling to room temperature, the reaction was poured into water (2 L) and diluted with ethyl acetate (1 L). The organic layer was separated, filtered through Celite and concentrated under reduced pressure to give (6-fluoropyridin-3-yl)-1-(phenylsulfonyl)-5-(4,4,5,5-tetramethyl-1,3,2-dioxaborolan-2-yl)-1H-pyrrolo[2,3-b]pyridine, which was used subsequently.

Step 3—Methyl 6-(2-(6-fluoropyridin-3-yl)-1-(phenylsulfonyl)-1H-pyrrolo[2,3-b]pyridin-5-yl)picolinate (27)

A suspension of crude compound 25 (22.18 g theory, 46.3 mmol, 1 equiv), methyl 6-bromopicolinate (12 g, 55.5 mmol, 1.2 equiv), potassium carbonate (19.2 g, 139 mmol, 3 equiv) and [1,1'-bis(diphenylphosphino)ferrocene] dichloropalladium(II) (1.9 g, 2.314 mmol, 0.05 equiv) in dioxane (190 mL) and water (40 mL) was heated at 90° C. for 3 hours. LC/MS indicated the reaction was complete. The reaction was diluted with ethyl acetate (500 mL) and water (500 mL) and filtered through a bed of Celite. The organic layer was separated and concentrated under reduced pressure. The crude product which was dissolved in dichloromethane and purified over silica gel (500 g), eluting with a gradient of 0 to 100% ethyl acetate in heptanes to give methyl 6-(2-(6-fluoropyridin-3-yl)-1-(phenylsulfonyl)-1H-pyrrolo[2,3-b]pyridin-5-yl)picolinate.

Step 4—6-(2-(6-Fluoropyridin-3-yl)-1-(phenylsulfonyl)-1H-pyrrolo[2,3-b]pyridin-5-yl)picolinic acid (28(a)) and 6-(2-(6-fluoropyridin-3-yl)-1H-pyrrolo[2,3-b]pyridin-5-yl)picolinic acid (28(b))

2 M Lithium hydroxide (175 mL, 350 mmol, 10 equiv) was added to a solution of compound 27 (17.1 g, 35 mmol, 1 equiv) in THF (350 mL). The reaction mixture was stirred overnight at room temperature, at which point LC/MS indicated all the starting material was consumed. In addition to the desired product, ~20% of compound 28(b) (loss of benzenesulfonyl group) was also present. The reaction was poured into 1N HCl (0.5 L) and extracted with ethyl acetate (1 L). The organic layer was separated and concentrated under reduced pressure to give a crude mixture of compound 28(b) and compound 28(a), which were used subsequently.

Step 5—N-(2-Cyanopropan-2-yl)-6-(2-(6-fluoropyridin-3-yl)-1-(phenylsulfonyl)-1H-pyrrolo[2,3-b]pyridin-5-yl)picolinamide (30)

N,N-diisopropylethylamine (14.1 mL, 81 mmol, 4 equiv) was added to a solution of the ~1 to 4 mixture of compound 28(b) and compound 28(a) (9.6 g, 20.23 mmol, 1 equiv) in DMF (135 mL). 2-Amino-2-methylpropanenitrile hydrochloride (3.7 g, 30.4 mmol, 1.5 equiv) was added and the reaction was stirred for ~30 minutes at room temperature. Propylphosphonic anhydride (T3P, 50 wt % in ethyl acetate) (23.8 mL, 40.5 mmol, 2 equiv) was added dropwise, with the internal temperature gradually increasing from 20 to 30° C. during the addition. After stirring overnight, LC/MS indicated ~50% conversion of starting material. Stirring an additional 24 hours resulted in no further conversion. The reaction mixture was poured into water (1 L) and extracted with ethyl acetate (500 mL). The organic layer was separated, washed with saturated brine (500 mL) and concentrated under reduced pressure. The crude solid was dissolved in THF, dry-loaded onto silica gel and purified on an AnaLogix column (80 g), eluting with a gradient of 0 to 50% ethyl acetate in dichloromethane. The resulting solid was triturated with MTBE (15 mL) to give N-(2-cyanopropan-2-yl)-6-(2-(6-fluoropyridin-3-yl)-1-(phenylsulfonyl)-1H-pyrrolo[2,3-b]pyridin-5-yl)picolinamide.

Step 6—N-(2-cyanopropan-2-yl)-6-(2-(6-fluoropyridin-3-yl)-1H-pyrrolo[2,3-b]pyridin-5-yl)picolinamide (31(a)) and N-(2-Cyanopropan-2-yl)-6-(2-(6-methoxypyridin-3-yl)-1H-pyrrolo[2,3-b]pyridin-5-yl)picolinamide (31(b))

1 N Potassium hydroxide in methanol (47.5 mL, 47.5 mmol, 10 equiv) was added to a solution of compound 30 (2.57 g, 4.75 mmol, 1 equiv) in THF (95 mL). After stirring overnight at room temperature, LC/MS indicated the reaction was complete along with ~40% of compound 31(b). The reaction was concentrated under reduced pressure. The residue was slurried with water (~100 mL) and the pH was adjusted to 6 with 1N HCl (20 mL). The solid was filtered and washed with water (20 mL). The crude solid was dissolved in THF, dry-loaded onto silica gel and partially purified on an AnaLogix column (40 g), eluting with a gradient of 0 to 100% THF in dichloromethane to give an inseparable mixture of compounds 31(a) and 31(b) which were used subsequently.

Step 7—N-(2-Cyanopropan-2-yl)-6-(2-(6-methoxypyridin-3-yl)-1H-pyrrolo[2,3-b]pyridin-5-yl)picolinamide (31(b))

Potassium hydroxide (1.4 g, 24.97 mmol, 10 equiv) was added to slurry of compounds 31(b) and 31(a) (1 g) in methanol (20 mL). The reaction mixture was heated at 50° C. for 3 days, at which point LC/MS indicated the reaction was complete. The reaction was concentrated under reduced pressure the residue was slurried with water (~100 mL) and the pH adjusted to 6 with 1 N HCl (~10 mL). The solid was filtered and washed with water (~20 mL). The crude solid (87% purity by LC/MS) was dissolved in DMSO and purified on a reverse phase AnaLogix column (100 g), eluting with a gradient of 0 to 100% THF in water. The appropriate fractions were pooled and concentrated under reduced pressure. The resulting solid was triturated with MTBE (~20 mL) and filtered to give N-(2-cyanopropan-2-yl)-6-(2-(6-methoxypyridin-3-yl)-1H-pyrrolo[2,3-b]pyridin-5-yl)picolinamide, 31(b).

Example 2: N-(2-cyanopropan-2-yl)-6-(2-(1-(difluoromethyl)-1H-pyrazol-4-yl)-1H-pyrrolo[2,3-b]pyridin-5-yl)picolinamide, 38

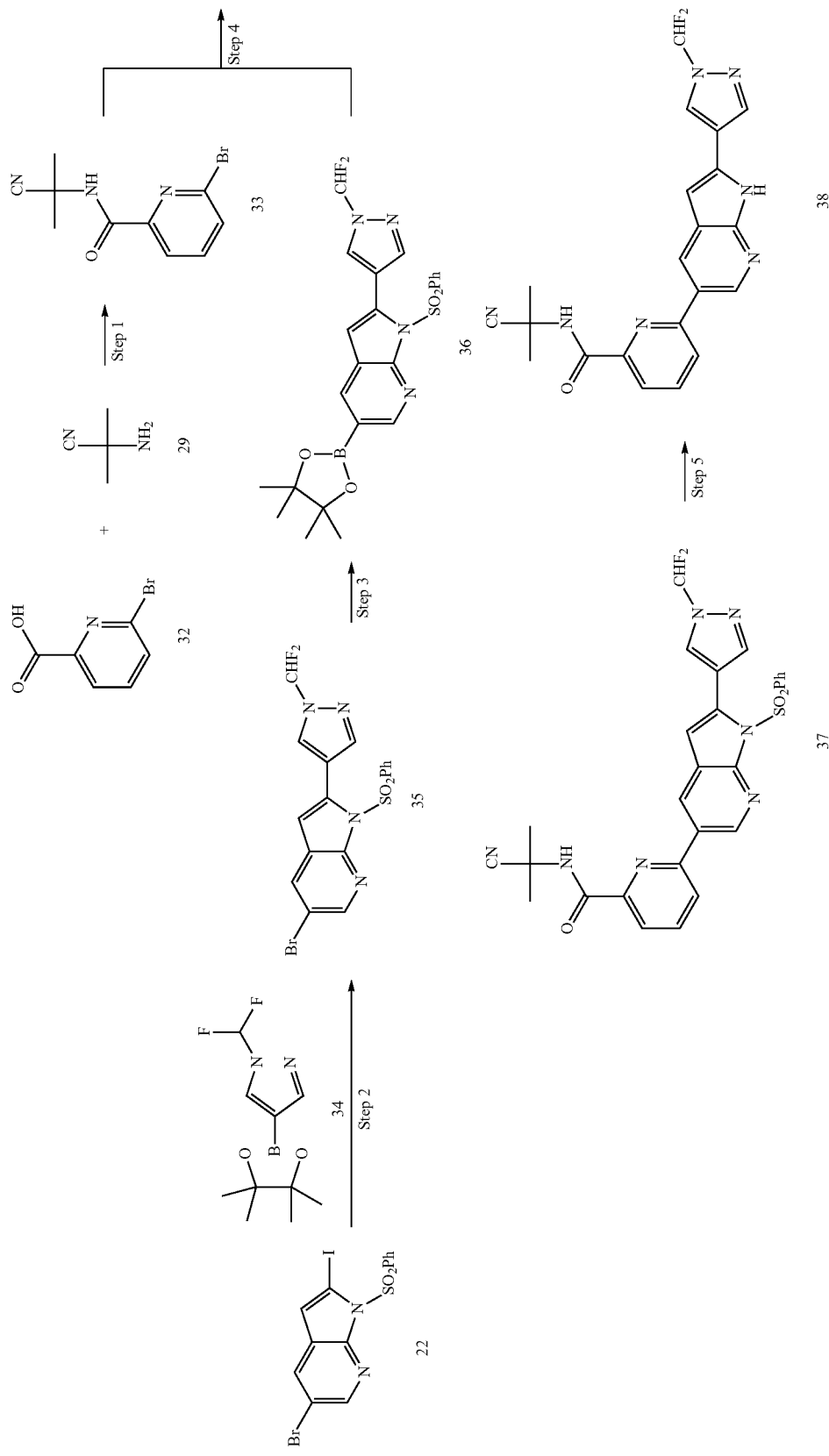

Step 1—6-Bromo-N-(2-cyanopropan-2-yl)picolinamide (33)

Triethylamine (93 mL, 683 mmol, 3 equiv) was added to a solution of compound 32 (46 g, 228 mmol, 1 equiv) and HBTU (99 g, 262 mmol, 1.15 equiv) in DMF (690 mL). After stirring at room temperature for 30 minutes, 2-amino-2-methylpropanenitrile hydrochloride (35.7 g, 296 mmol, 1.3 equiv) was added and the reaction mixture was stirred overnight. The solution was poured into water (4 L) and extracted with ethyl acetate (3 L). The organic layer was separated, washed with saturated brine (2 L) and concentrated under reduced pressure. The crude product which was dissolved in dichloromethane and purified over silica gel (0.7 Kg), eluting with a gradient of 10 to 20% ethyl acetate in heptanes to give 6-bromo-N-(2-cyanopropan-2-yl)picolinamide.

Step 2: 5-bromo-2-(1-(difluoromethyl)-1H-pyrazol-4-yl)-1-(phenylsulfonyl)-1H-pyrrolo[2,3-b]pyridine (35)

A suspension of compound 22 (92 g, 199 mmol, 1 equiv), compound 34 (53.3 g, 219 mmol, 1.1 equiv), potassium carbonate (82 g, 596 mmol, 3 equiv) in a mixture of dioxane (1.1 L) and water (220 mL) was sparged with nitrogen for 10 minutes. Tetrakis(triphenylphosphine) palladium(0) (23 g, 19.87 mmol, 0.1 equiv) was added and the reaction mixture was refluxed overnight. LC/MS indicated the reaction was complete. The reaction was poured into water (1 L) and diluted with ethyl acetate (1 L). The organic layer was separated and concentrated under reduced pressure. The crude product which was dissolved in dichloromethane and purified over silica gel (1 Kg), eluting initially with 10% MTBE in heptanes, followed by dichloromethane to give 5-bromo-2-(1-(difluoromethyl)-1H-pyrazol-4-yl)-1-(phenylsulfonyl)-1H-pyrrolo[2,3-b]pyridine.

Step 3—2-(1-(difluoromethyl)-1H-pyrazol-4-yl)-1-(phenylsulfonyl)-5-(4,4,5,5-tetramethyl-1,3,2-dioxaborolan-2-yl)-1H-pyrrolo[2,3-b]pyridine (36)

Potassium acetate (56.1 g, 572 mmol, 1 equiv) and [1,1'-bis(diphenylphosphino)ferrocene]dichloropalladium (II) (15.6 g, 19.06 mmol, 1 equiv) were sequentially added to a solution of compound 35 (86.4 g, 191 mmol, 1 equiv) and bis(pinacolato)diboron (58.1 g, 229 mmol, 1 equiv) in DMF (760 mL). After heating at 80° C. overnight, the reaction was cooled to room temperature, poured into water (5 L) and diluted with ethyl acetate (2 L). The organic layer was separated, filtered through Celite and concentrated under reduced pressure to give 2-(1-(difluoromethyl)-1H-pyrazol-4-yl)-1-(phenylsulfonyl)-5-(4,4,5,5-tetramethyl-1,3,2-dioxaborolan-2-yl)-1H-pyrrolo[2,3-b]pyridine which was used subsequently.

Step 4—N-(2-Cyanopropan-2-yl)-6-(2-(1-(difluoromethyl)-1H-pyrazol-4-yl)-1-(phenylsulfonyl)-1H-pyrrolo[2,3-b]pyridin-5-yl)picolinamide (37)

A suspension of compound 33 (61.1 g, 228 mmol, 1 equiv), crude compound 36 (95 g, 190 mmol), potassium carbonate (79 g, 570 mmol) and [1,1'-bis(diphenylphosphino) ferrocene] dichloropalladium(II) (7.75 g, 9.49 mmol) in dioxane (800 mL) and water (160 mL) was refluxed for 3 hours, at which point LC/MS indicated the reaction was complete. The reaction was diluted with ethyl acetate (1 L) and water (1 L). The organic layer was separated and concentrated under reduced pressure. The crude product which was dissolved in dichloromethane and purified over silica gel (1 kg), eluting with a gradient of 50 to 80% ethyl acetate in heptanes to give N-(2-cyanopropan-2-yl)-6-(2-(1-(difluoromethyl)-1H-pyrazol-4-yl)-1-(phenylsulfonyl)-1H-pyrrolo[2,3-b]pyridin-5-yl)picolinamide.

Step 5—N-(2-Cyanopropan-2-yl)-6-(2-(1-(difluoromethyl)-1H-pyrazol-4-yl)-1H-pyrrolo[2,3-b]pyridin-5-yl)picolinamide (38)

Tetrabutylammonium fluoride trihydrate (115 g, 363 mmol, 4 equiv) was added to a solution of compound 37 (51 g, 91 mmol, 1 equiv) in THF (900 mL). After heating at 40° C. overnight, LC/MS indicated the reaction was complete. The reaction mixture was poured into saturated brine (1 L) and extracted with ethyl acetate (1 L). The organic layer was concentrated under reduced pressure. The crude solid was triturated with dichloromethane (~200 mL) and filtered to give N-(2-cyanopropan-2-yl)-6-(2-(1-(difluoromethyl)-1H-pyrazol-4-yl)-1H-pyrrolo[2,3-b]pyridin-5-yl)picolinamide. The filtrate was purified over silica gel (600 g) eluting with ethyl acetate to give additional product after trituration with dichloromethane (~50 mL). The two batches were combined and dried under high vacuum at 40° C. for 3 hours to give N-(2-cyanopropan-2-yl)-6-(2-(1-(difluoromethyl)-1H-pyrazol-4-yl)-1H-pyrrolo[2,3-b]pyridin-5-yl)picolinamide.

Example 3: N-(2-cyanopropan-2-yl-1,1,1,3,3,3-d6)-6-(2-(1-(difluoromethyl)-1H-pyrazol-4-yl)-1H-pyrrolo[2,3-b]pyridin-5-yl)picolinamide (P-037)

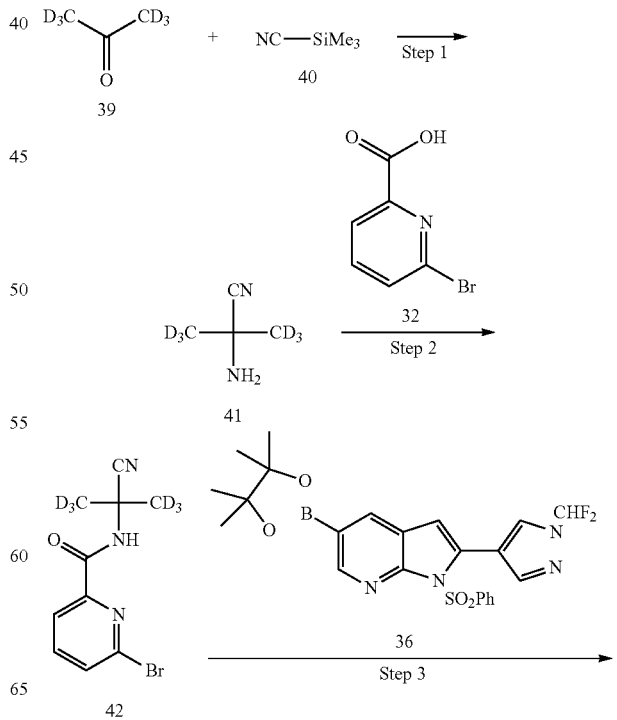

145

-continued

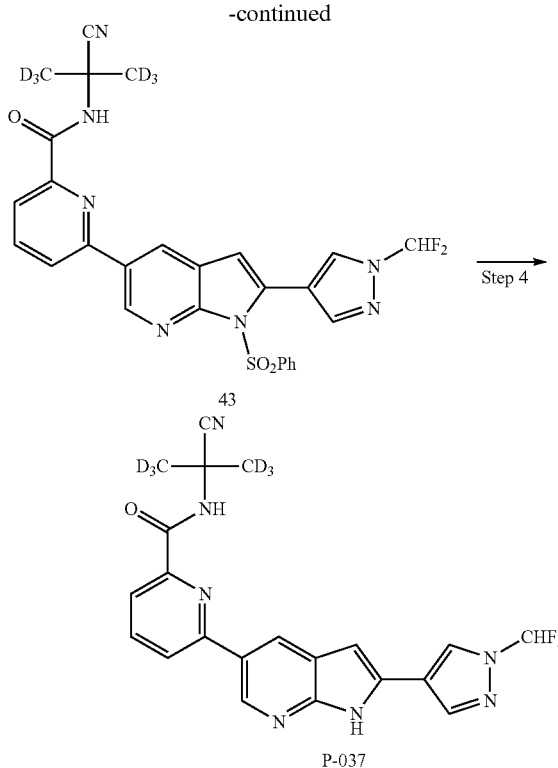

43

P-037

Step 1—Preparation of 2-Amino-2-(methyl-d3)-(3-d3-propane)nitrile (41)

Trimethylsilylcyanide 40 is added to deuterated acetone 39 (99.9 atom % D) (one equivalent) and stirred at room temperature for 24 hours. The reaction mixture is dissolved in appropriate amount of 1,4-dioxane and stirred at 0° C. Ammonia gas is bubbled through this solution, and then the reaction mixture is allowed to stir overnight at room temperature under an atmosphere of ammonia. The ammonia is then evaporated in vacuum. The residue is collected and used for subsequent reaction as is.

Step 2—6-bromo-N-(2-cyanopropan-2-yl-1,1,1,3,3,3-d6)picolinamide (42)

Triethylamine is added to a solution of compound 32 and HBTU in DMF (690 mL). After stirring at room temperature for 30 minutes, 2-Amino-2-(methyl-d3)-(3-d3-propane)nitrile 41 is added, and the reaction mixture is stirred overnight. The solution is poured into water and extracted with ethyl acetate. The organic layer is separated, washed with saturated brine, and concentrated under reduced pressure. The crude product is dissolved in dichloromethane and purified over silica gel, eluting with a gradient of 10 to 20% ethyl acetate in heptanes to give 6-bromo-N-(2-cyanopropan-2-yl-,1,1,3,3,3-d6)picolinamide.

Step 3—N-(2-cyanopropan-2-yl-1,1,1,3,3,3-d6)-6-(2-(1-(difluoromethyl)-1H-pyrazol-4-yl)-1-(phenylsulfonyl)-1H-pyrrolo[2,3-b]pyridin-5-yl)picolinamide (43)

A suspension of Compound 36, compound 42, potassium carbonate, and [1,1'-bis(diphenylphosphino) ferrocene] dichloropalladium(II) in dioxane and water is refluxed until the reaction is deemed complete by LC/MS. The reaction is then diluted with ethyl acetate and water. The organic layer is separated and concentrated under reduced pressure. The crude product is dissolved in dichloromethane and purified over silica gel, eluting with a gradient of 50 to 80% ethyl acetate in heptanes to give N-(2-cyanopropan-2-yl-1,1,1,3,3-d6)-6-(2-(1-(difluoromethyl)-1H-pyrazol-4-yl)-1-(phenylsulfonyl)-1H-pyrrolo[2,3-b]pyridin-5-yl)picolinamide.

Step 4—N-(2-cyanopropan-2-yl-1,1,1,3,3,3-d6)-6-(2-(1-(difluoromethyl)-1H-pyrazol-4-yl)-1H-pyrrolo[2,3-b]pyridin-5-yl)picolinamide (P-037)

Tetrabutylammonium fluoride trihydrate is added to a solution of compound 43 in THF and heated at 40° C. overnight. The reaction mixture is poured into saturated brine and extracted with ethyl acetate. The organic layer is concentrated under reduced pressure. The crude solid is triturated with dichloromethane and filtered to give N-(2-cyanopropan-2-yl-1,1,1,3,3,3-d6)-6-(2-(1-(difluoromethyl)-1H-pyrazol-4-yl)-1H-pyrrolo[2,3-b]pyridin-5-yl)picolinamide. The filtrate is purified over silica gel, eluting with ethyl acetate to give additional product after trituration with dichloromethane. The two batches are combined and dried under high vacuum at 40° C. to give N-(2-cyanopropan-2-yl-1,1,1,3,3,3-d6)-6-(2-(1-(difluoromethyl)-1H-pyrazol-4-yl)-1H-pyrrolo[2,3-b]pyridin-5-yl)picolinamide.

BIOLOGICAL EXAMPLES

Example 4: Biochemical TGFβR2 Assay

The $IC_{50}$ of certain compounds in this disclosure against TGFβR2 was conducted under contract at Thermo Fisher Scientific, Life Sciences Solutions as part of their SelectScreen™ profiling service. The TGFβR2 assay used the LanthaScreen® Europium Kinase Binding Assay. Binding of an Alexa Fluor® conjugate Tracer 199 (100 nM) to TGFβR2 (5 nM) was detected by addition of a Eu-labeled anti-tag antibody (5 nM) in Kinase Buffer A (50 mM HEPES pH 7.5, 0.01% BRIJ-35, 10 mM $MgCl_2$, 1 mM EGTA) and 1% final DMSO. Binding of the tracer and antibody to a kinase resulted in a high degree of FRET, whereas displacement of the tracer with a kinase inhibitor resulted in a loss of FRET. The percent inhibition was calculated from the emission ratio of Alexa Fluor® and Europium as documented by Thermo Fisher (www.thermofisher.com/kinaseprofiling). The $IC_{50}$ of certain compounds in this disclosure was determined by testing a dilution series of the compound in duplicate at five concentrations (1.0, 0.25, 0.062, 0.015 and 0.0039 μM) by fitting the inhibition data with a sigmoidal curve fit model.

Table II provides data indicating TGFBR2 biochemical inhibitory activities for exemplary compounds as described herein.

Example 5: Biochemical FLT3 D835Y Assay

FLT3 D835Y assays were conducted on certain compounds of this disclosure as described in U.S. Patent Publication No. US2017/0267660.

Table II provides data indicating FLT3 D835Y biochemical inhibitory activities for exemplary compounds as described herein.

In the table below, activity is provided as follows: +++=0.0001 μM<IC$_{50}$<10 μM; ++=10 μM<IC$_{50}$<100 μM, +=100 μM<IC$_{50}$<200 μM, X=undetectable.

TABLE II

| P # | TGFβR2 GMean: IC$_{50}$ (μM) (Biochemical Assay) | FLT3 D835Y GMean: IC$_{50}$ (μM) (Biochemical Assay) |
| --- | --- | --- |
| P-001 | +++ | +++ |
| P-003 | +++ | +++ |
| P-004 | +++ | +++ |
| P-005 | +++ | +++ |
| P-006 | +++ | +++ |
| P-007 | +++ | +++ |
| P-008 | +++ | +++ |
| P-009 | +++ | +++ |
| P-010 | +++ | +++ |
| P-011 | +++ | +++ |
| P-012 | +++ | +++ |
| P-013 | +++ | +++ |
| P-014 | +++ | +++ |
| P-015 | +++ | +++ |
| P-016 | +++ | +++ |
| P-017 | +++ | +++ |
| P-018 | +++ | +++ |
| P-019 | +++ | +++ |
| P-021 | +++ | +++ |
| P-024 | +++ | +++ |

Another embodiment of this disclosure relates to a compound as described herein having a TGFβR2 IC$_{50}$ value ranging from 0.0001 μM to 10 μM.

Another embodiment of this disclosure relates to a compound as described herein having a TGFβR2 IC$_{50}$ value ranging from 10 μM to 50 μM.

Another embodiment of this disclosure relates to a compound as described herein having a TGFβR2 IC$_{50}$ value ranging from 50 μM to 100 μM.

Another embodiment of this disclosure relates to a compound as described herein having a FLT3 D835Y IC$_{50}$ value ranging from 0.0001 μM to 10 μM.

Another embodiment of this disclosure relates to a compound as described herein having a FLT3 D835Y IC$_{50}$ value ranging from 10 μM to 50 μM.

Another embodiment of this disclosure relates to a compound as described herein having a FLT3 D835Y IC$_{50}$ value ranging from 50 μM to 100 μM.

Another embodiment of this disclosure relates to a compound as described herein having both TGFβR2 and FLT3 D835Y IC$_{50}$ value ranging from 0.0001 μM to 10 μM.

Another embodiment of this disclosure relates to a compound as described herein having both TGFβR2 and FLT3 D835Y IC$_{50}$ value ranging from 10 μM to 50 μM.

Another embodiment of this disclosure relates to a compound as described herein having both TGFβR2 and FLT3 D835Y IC$_{50}$ values ranging from 50 μM to 100 μM.

All patents and other references cited herein are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of the embodiments described herein are exemplary and are not intended as limitations on the scope of the disclosure. Changes therein and other uses will occur to those skilled in the art, which are encompassed within the spirit of the disclosure, are defined by the scope of the claims.

It will be readily apparent to one skilled in the art that varying substitutions and modifications may be made to the present disclosure described herein without departing from the scope and spirit of the disclosure. For example, variations can be made to provide additional compounds of Formula I and all sub-embodiments thereof, and/or various methods of administration for the compounds of this disclosure. Thus, such additional embodiments are within the scope of the present disclosure and the following claims.

The present disclosure illustratively described herein suitably may be practiced in the absence of any element or elements, limitation or limitations which is not specifically described herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically described by the embodiments and optional features, modification and variation of the concepts herein described may be resorted to by those skilled in the art, and that such modifications and variations are considered to be within the scope of this disclosure as defined by the appended claims.

In addition, where features or embodiments of the disclosure are described in terms grouping of alternatives, those skilled in the art will recognize that the disclosure is also thereby described in terms of any individual member or subgroup of members of the groups described herein.

Also, unless indicated to the contrary, where various numerical values are provided for embodiments, additional embodiments are described by taking any 2 different values as the endpoints of a range. Such ranges are also within the scope of the present disclosure.

Thus, additional embodiments are within the scope of the disclosure and within the following claims.

What is claimed is:

1. A compound having Formula I:

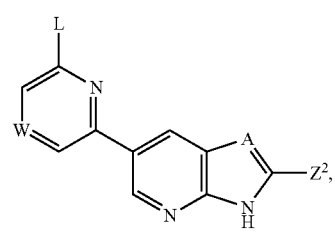

or a pharmaceutically acceptable salt, a solvate, a tautomer, a stereoisomer, or a deuterated analog thereof, wherein:

A is N or —C(Z$^3$)=;
W is —C(R$^2$)= or N;
Z$^3$ is hydrogen or halo;
Z$^2$ is:

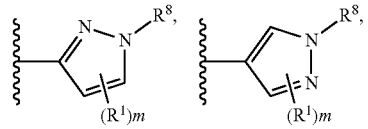

-continued

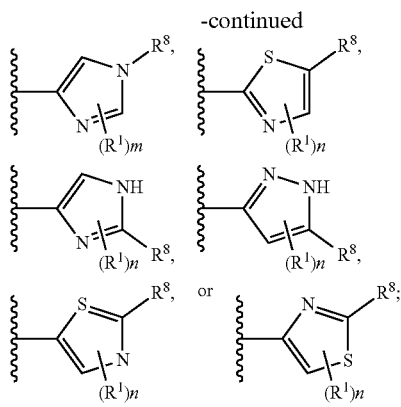

L is —SO$_2$—NR$^6$R$^7$, —NHC(O)R$^4$, or —C(O)NR$^3$R$^4$;
R$^1$ is C$_{1-6}$alkyl, halo, or halo-C$_{1-6}$alkyl;
R$^2$ is hydrogen, —CH$_3$, —CH$_2$F, —CHF$_2$, —CF$_3$, or halo;
R$^3$ is hydrogen or C$_{1-6}$alkyl;
R$^4$ is C$_{3-6}$cycloalkyl, C$_{3-6}$cycloalkyl-C$_{1-3}$alkylene, cyano-C$_{3-6}$ cycloalkyl, cyano-C$_{3-6}$ cycloalkyl-C$_{1-3}$alkylene, cyano-C$_{1-6}$alkylene, heterocycloalkyl, heteroaryl, or —(CH$_2$)—[(CR$^{10}$)]$_2$-OH, wherein the C$_{3-6}$cycloalkyl, C$_{3-6}$cycloalkyl-C$_{1-3}$alkylene, cyano-C$_{3-6}$ cycloalkyl, cyano-C$_{3-6}$ cycloalkyl-C$_{1-3}$alkyl, cyano-C$_{1-6}$alkylene, heterocycloalkyl, and heteroaryl are optionally substituted with 1-2 G groups;
or R$^3$ and R$^4$, together with the N atom to which they are attached, join to form a 4-6 membered heterocycloalkyl moiety substituted with 1-2 G groups;
R$^6$ is hydrogen, C$_{1-6}$alkyl, cyano-C$_{1-6}$alkylene optionally substituted with 1-2 G groups, or C$_{3-6}$cycloalkyl optionally substituted with 1-2 G$^2$ groups;
R$^7$ is hydrogen or C$_{1-6}$alkyl;
or R$^6$ and R$^7$, together with the N atom to which they are attached, join to form a heterocycloalkyl moiety substituted with 1-2 G groups;
R$^8$ is C$_{1-3}$alkyl, hydroxy-C$_{1-6}$alkyl, halo-C$_{1-6}$alkyl, cyano-C$_{1-6}$alkylene, —[C(R$^9$)$_2$]$_{1-2}$—C$_{3-6}$cycloalkyl, —[C(R$^9$)$_2$]$_{1-2}$-heterocycloalkyl, —[C(R$^9$)$_2$]$_{1-2}$-heteroaryl, —[C(R$^9$)$_2$]$_{1-2}$—SO$_2$—C$_{1-3}$alkyl, —[C(R$^9$)$_2$]$_{1-2}$—C(O)—C$_{1-3}$alkyl, —[C(R$^9$)$_2$]$_{1-2}$—C(O)—N(C$_{1-3}$alkyl)$_2$, —[C(R$^9$)$_2$]$_{1-2}$—C(O)—NH$_2$, —[C(R$^9$)$_2$]$_{1-2}$—C(O)—C$_{3-6}$cycloalkyl, or —[C(R$^9$)$_2$]$_{1-2}$—C(O)-heterocycloalkyl, or —CH$_2$—C(O)-pyridyl;
each R$^9$ is independently selected from hydrogen, C$_{1-6}$alkyl, C$_{3-6}$cycloalkyl, halo, and halo-C$_{1-6}$alkyl;
each R$^{10}$ is C$_{1-3}$alkyl or two R$^{10}$, together with the C atom to which they are attached, join to form a C$_{3-6}$cycloalkyl;
each G is independently hydroxyl, C$_{1-6}$alkyl, C$_{3-6}$cycloalkyl, or heterocycloalkyl;
each G$^2$ is independently C$_{1-6}$alkyl, halogen, or cyano;
m is 0, 1, or 2; and
n is 0 or 2;
provided that the compound is not
N-(2-cyano-2-methyl-propyl)-6-[2-[1-(2,2,2-trifluoroethyl)pyrazol-4-yl]-1H-pyrrolo[2,3-b]pyridin-5-yl]pyridine-2-carboxamide,
N-(2-cyano-2-methyl-propyl)-6-[2-[1-(difluoromethyl)pyrazol-4-yl]-1H-pyrrolo[2,3-b]pyridin-5-yl]pyridine-2-carboxamide, N-(1-cyano-1-methyl-ethyl)-6-[2-[1-(difluoromethyl)pyrazol-4-yl]-1H-pyrrolo[2,3-b]pyridin-5-yl]pyridine-2-carboxamide,
N-(1-cyano-1-methyl-ethyl)-6-[2-(2-isopropyl-4-methyl-thiazol-5-yl)-1H-pyrrolo[2,3-b]pyridin-5-yl]pyridine-2-carboxamide,
6-[2-[1-(2-cyanoethyl)pyrazol-4-yl]-1H-pyrrolo[2,3-b]pyridin-5-yl]-N-(1-cyano-1-methyl-ethyl)pyridine-2-carboxamide,
N-(1-cyano-1-methyl-ethyl)-6-[2-[1-(2-morpholinoethyl)pyrazol-4-yl]-1H-pyrrolo[2,3-b]pyridin-5-yl]pyridine-2-carboxamide,
N-(1-cyano-1-methyl-ethyl)-6-[2-(1-isopropyl-3-methyl-pyrazol-4-yl)-1H-pyrrolo[2,3-b]pyridin-5-yl]pyridine-2-carboxamide,
6-[3-chloro-2-[1-(difluoromethyl)pyrazol-4-yl]-1H-pyrrolo[2,3-b]pyridin-5-yl]-N-(1-cyano-1-methyl-ethyl)pyridine-2-carboxamide,
6-[3-chloro-2-(1-isopropyl-3-methyl-pyrazol-4-yl)-1H-pyrrolo[2,3-b]pyridin-5-yl]-N-(1-cyano-1-methyl-ethyl)pyridine-2-carboxamide,
N-(1-cyano-1-methyl-ethyl)-6-[2-[1-(2,2,2-trifluoroethyl)pyrazol-4-yl]-1H-pyrrolo[2,3-b]pyridin-5-yl]pyridine-2-carboxamide,
N-(2-cyanopropan-2-yl)-6-(2-(1-(2-hydroxy-2-methylpropyl)-1H-pyrazol-4-yl)-1H-pyrrolo[2,3-b]pyridin-5-yl)picolinamide,
N-(2-cyanopropan-2-yl)-6-(2-(1-(2,2-difluoroethyl)-1H-pyrazol-4-yl)-1H-pyrrolo[2,3-b]pyridin-5-yl)picolinamide,
N-(2-cyanopropan-2-yl)-6-(2-(1-(oxetan-3-ylmethyl)-1H-pyrazol-4-yl)-1H-pyrrolo[2,3-b]pyridin-5-yl)picolinamide, and
N-(2-cyanopropan-2-yl)-6-(2-(1-((methylsulfonyl)methyl)-1H-pyrazol-4-yl)-1H-pyrrolo[2,3-b]pyridin-5-yl)picolinamide.

2. The compound according to claim 1, wherein W is —C(R$^2$)=, and R$^2$ is —CH$_3$, F, Cl, or Br.
3. The compound according to claim 1, wherein W is —C(R$^2$)=, and R$^2$ is hydrogen.
4. The compound according to claim 1, wherein W is N.
5. The compound according to claim 1, wherein A is —C(Z$^3$)=, and L is —C(O)NR$^3$R$^4$.
6. The compound according to claim 1, wherein A is —C(Z$^3$)=, and L is:

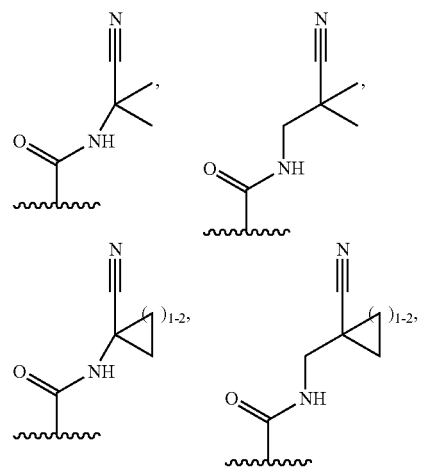

-continued
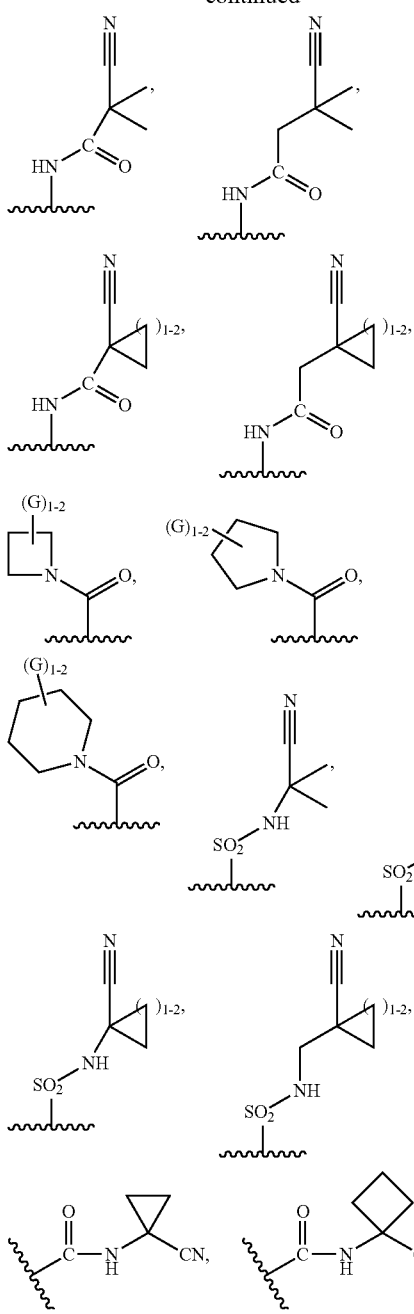
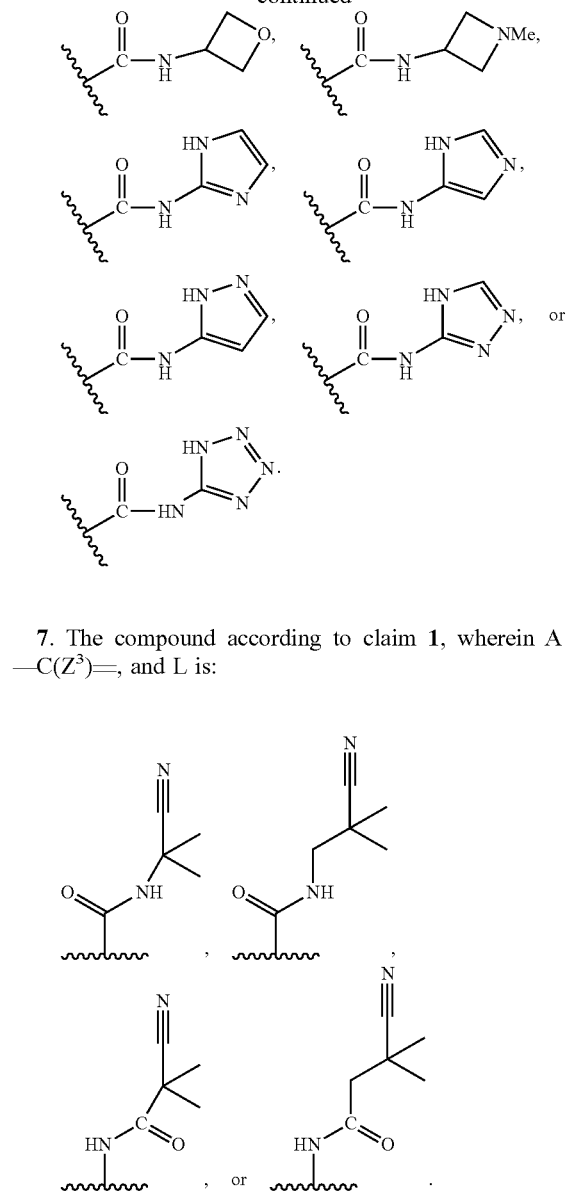
7. The compound according to claim 1, wherein A is —C(Z³)═, and L is:
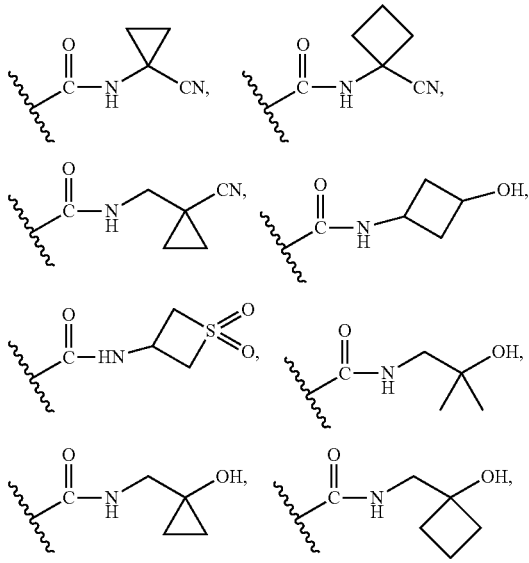
8. The compound according to claim 1 having one of the following Formulae:
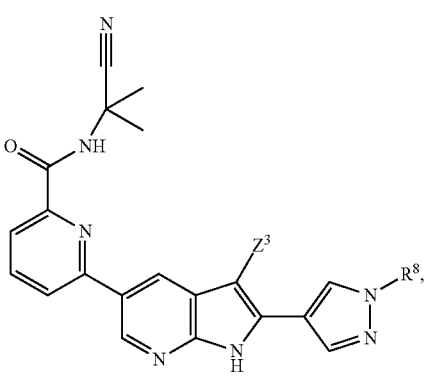
I(a)

I(b)
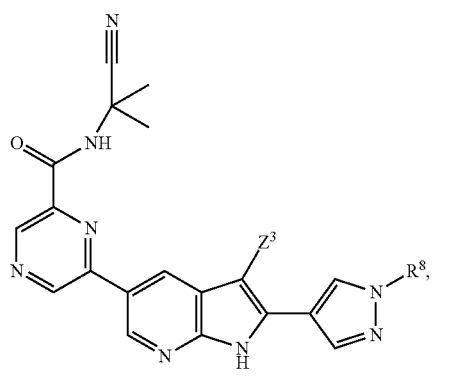
I(c)
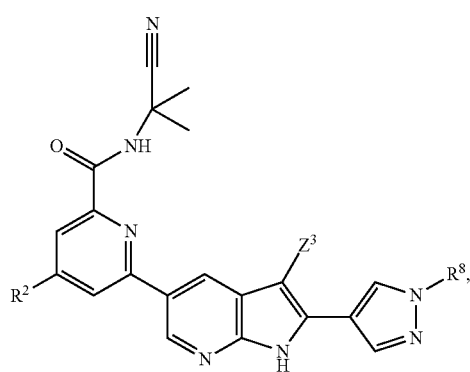
I(d)
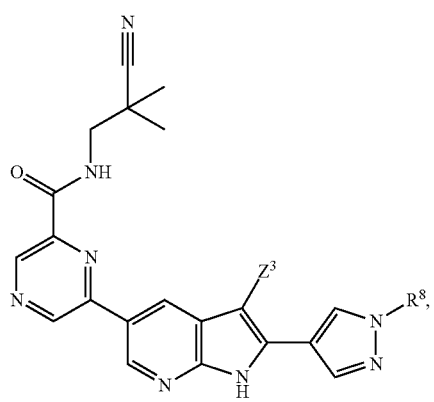
I(e)
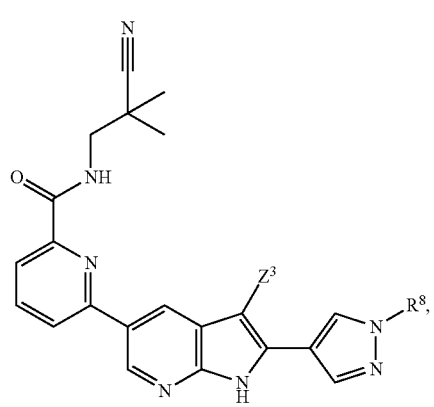
I(f)
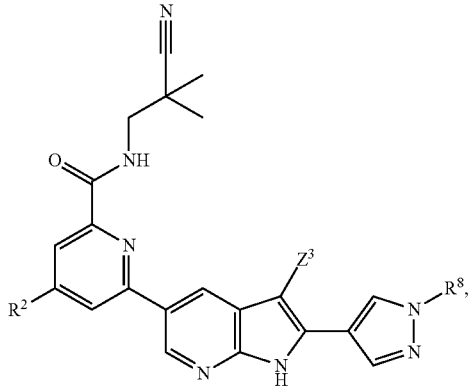
I(g)
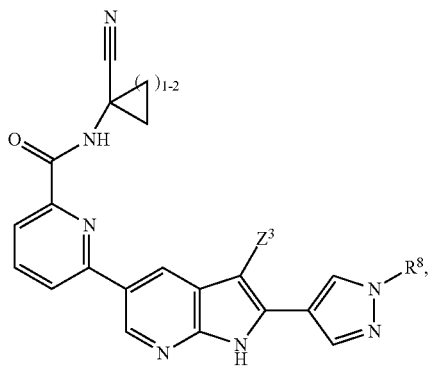
I(h)
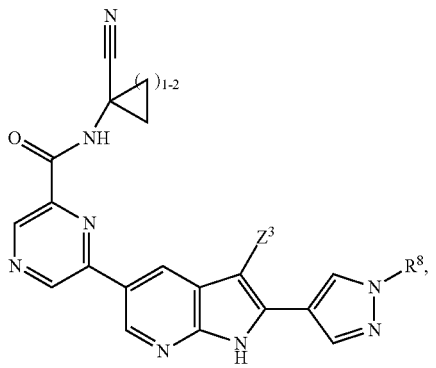
I(i)
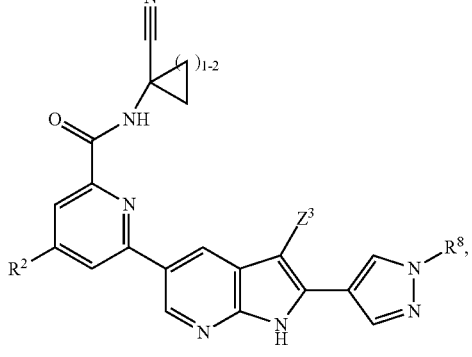

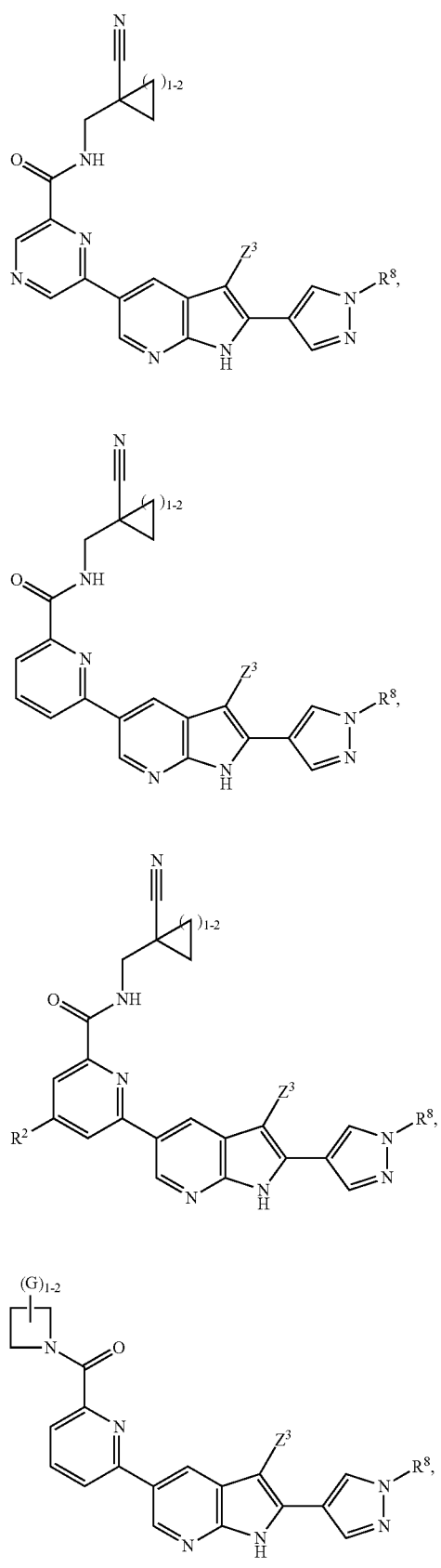
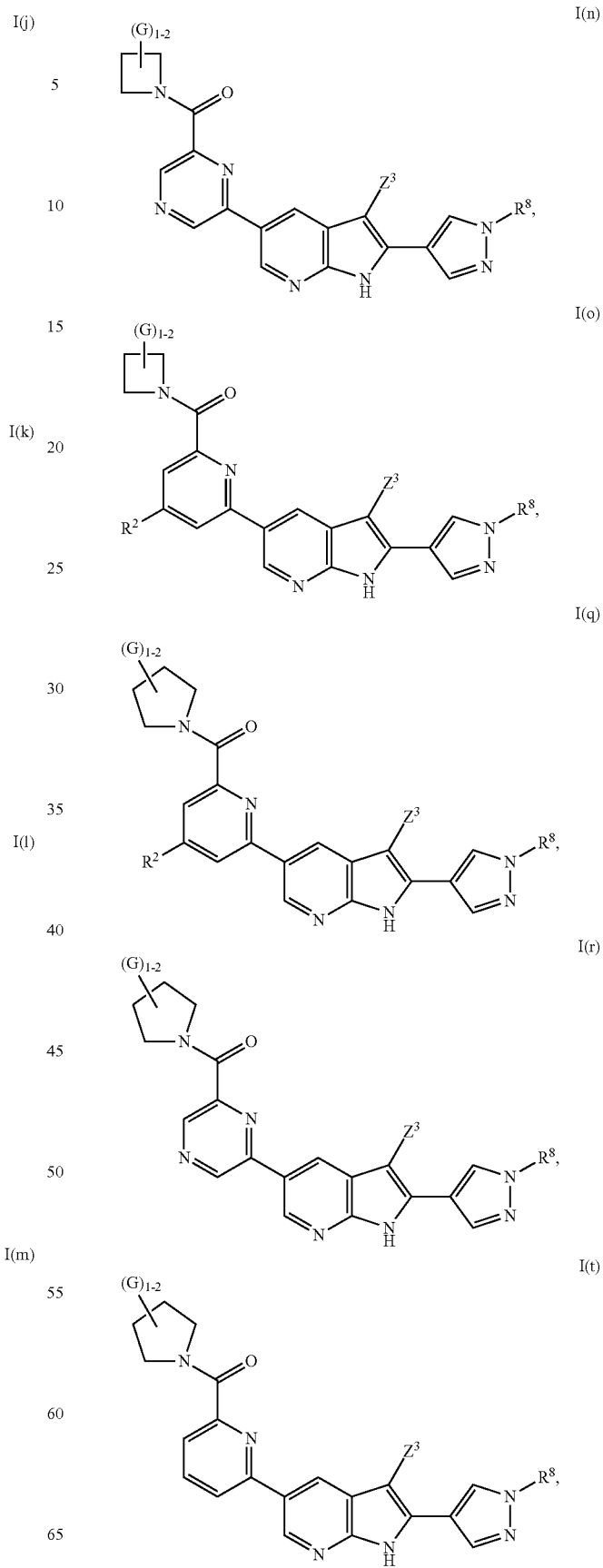

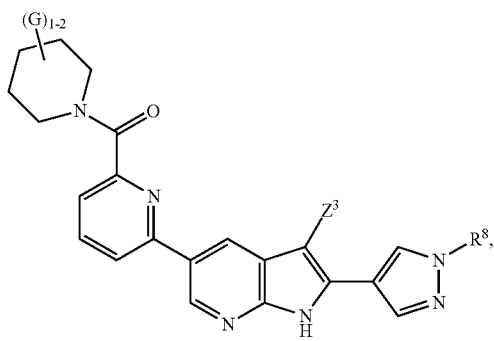
I(u)
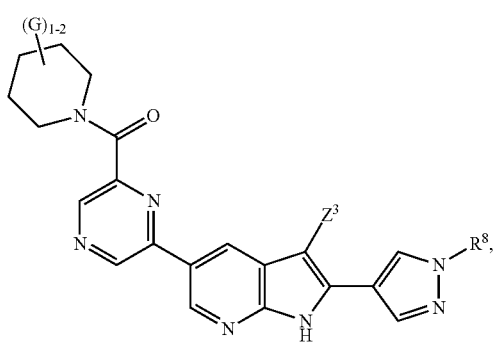
I(v)
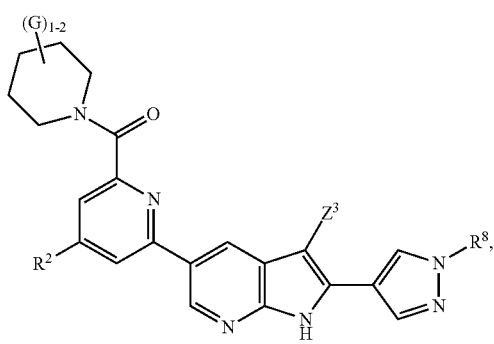
I(w)
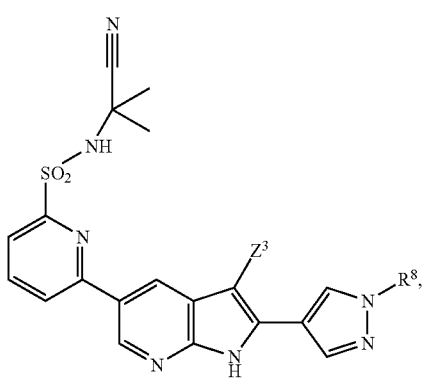
I(x)
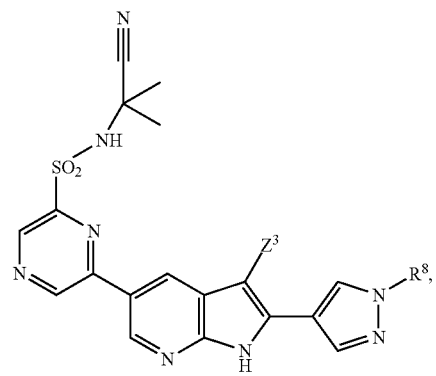
I(y)
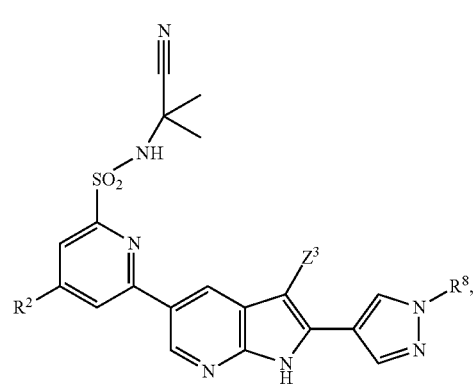
I(z)
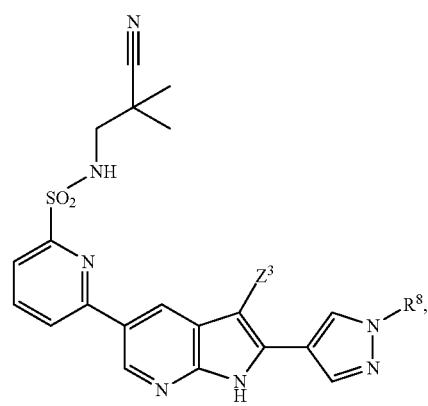
I(aa)
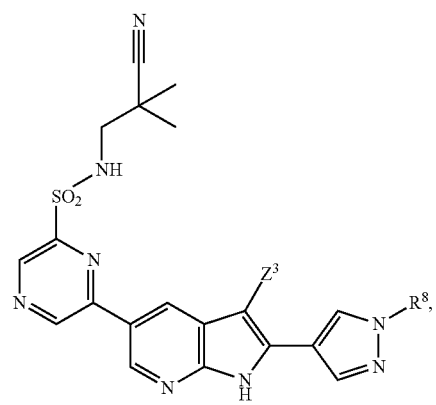
I(bb)

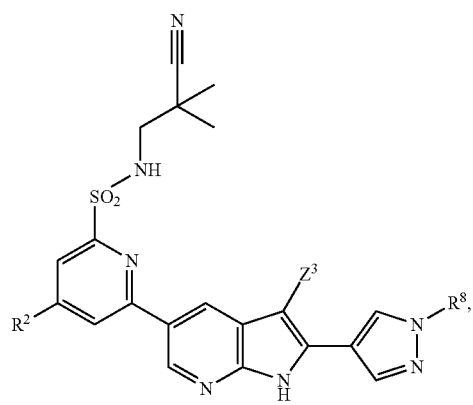
I(cc)
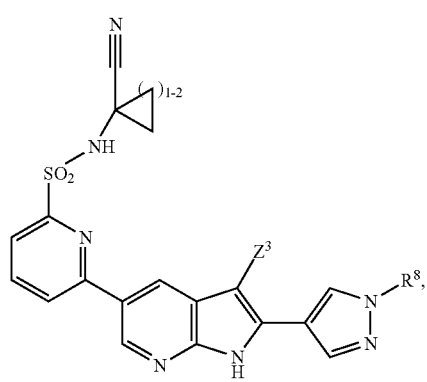
I(dd)
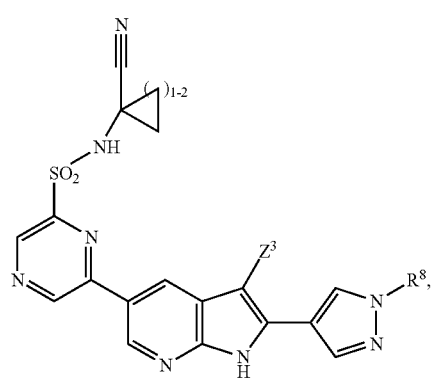
I(ee)
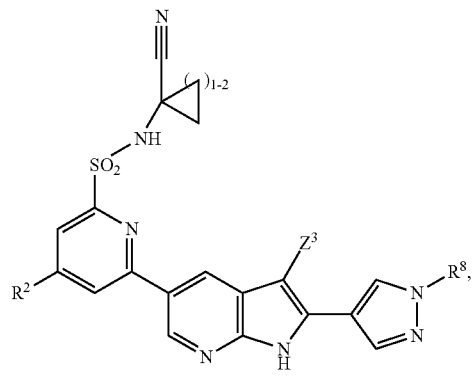
I(ff)
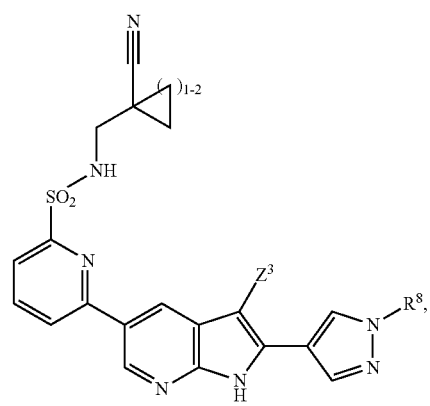
I(gg)
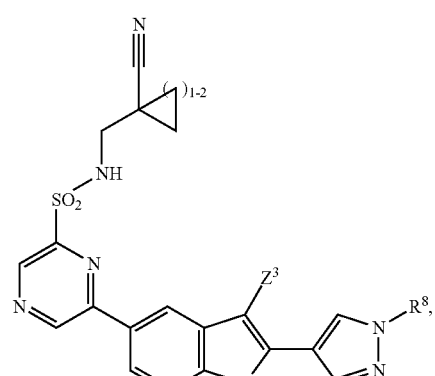
I(hh)
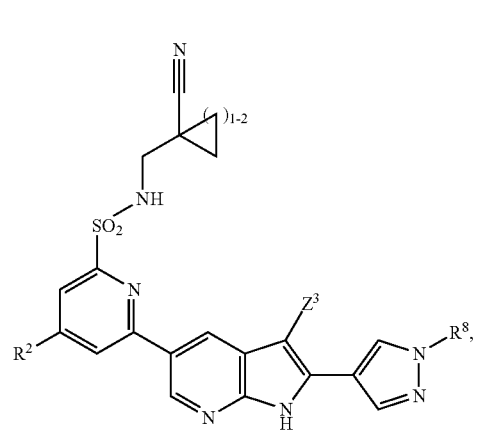
I(ii)
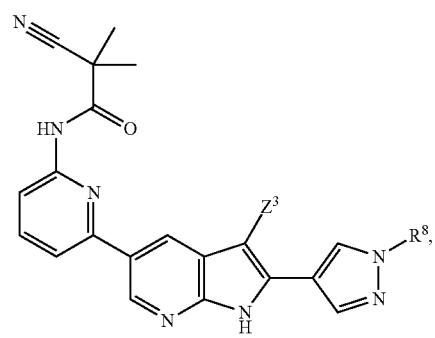
I(jj)

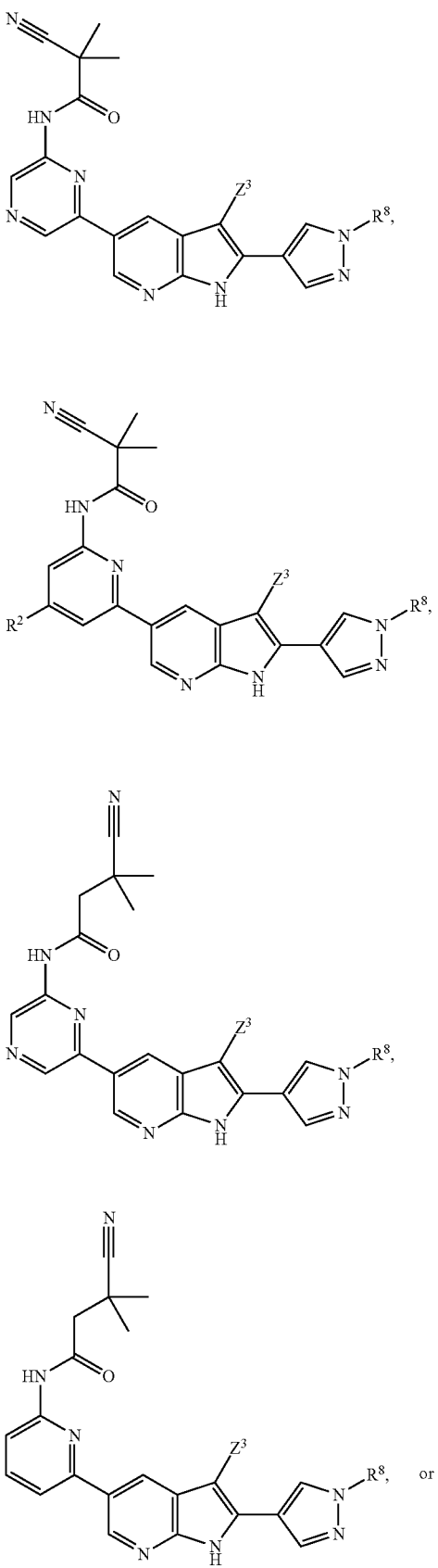

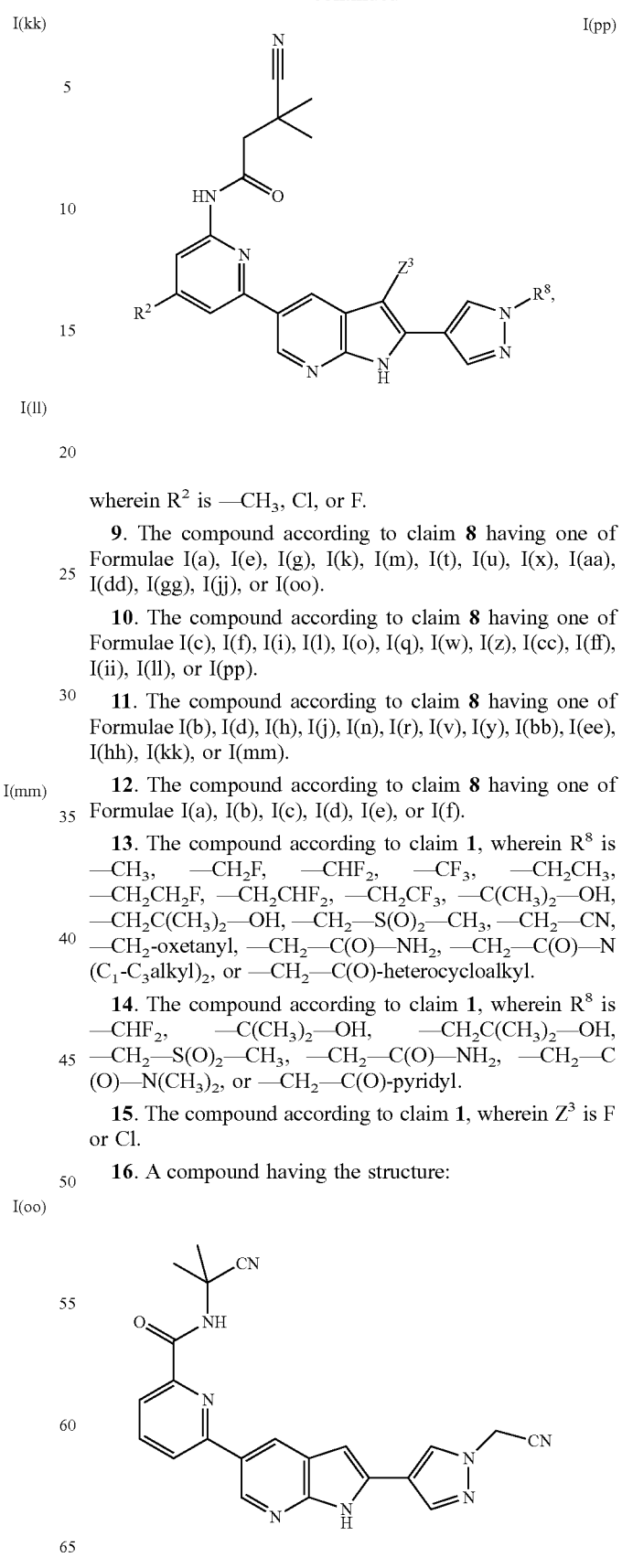

wherein R² is —CH₃, Cl, or F.

9. The compound according to claim 8 having one of Formulae I(a), I(e), I(g), I(k), I(m), I(t), I(u), I(x), I(aa), I(dd), I(gg), I(jj), or I(oo).

10. The compound according to claim 8 having one of Formulae I(c), I(f), I(i), I(l), I(o), I(q), I(w), I(z), I(cc), I(ff), I(ii), I(ll), or I(pp).

11. The compound according to claim 8 having one of Formulae I(b), I(d), I(h), I(j), I(n), I(r), I(v), I(y), I(bb), I(ee), I(hh), I(kk), or I(mm).

12. The compound according to claim 8 having one of Formulae I(a), I(b), I(c), I(d), I(e), or I(f).

13. The compound according to claim 1, wherein R⁸ is —CH₃, —CH₂F, —CHF₂, —CF₃, —CH₂CH₃, —CH₂CH₂F, —CH₂CHF₂, —CH₂CF₃, —C(CH₃)₂—OH, —CH₂C(CH₃)₂—OH, —CH₂—S(O)₂—CH₃, —CH₂—CN, —CH₂-oxetanyl, —CH₂—C(O)—NH₂, —CH₂—C(O)—N(C₁-C₃alkyl)₂, or —CH₂—C(O)-heterocycloalkyl.

14. The compound according to claim 1, wherein R⁸ is —CHF₂, —C(CH₃)₂—OH, —CH₂C(CH₃)₂—OH, —CH₂—S(O)₂—CH₃, —CH₂—C(O)—NH₂, —CH₂—C(O)—N(CH₃)₂, or —CH₂—C(O)-pyridyl.

15. The compound according to claim 1, wherein Z³ is F or Cl.

16. A compound having the structure:

163
-continued
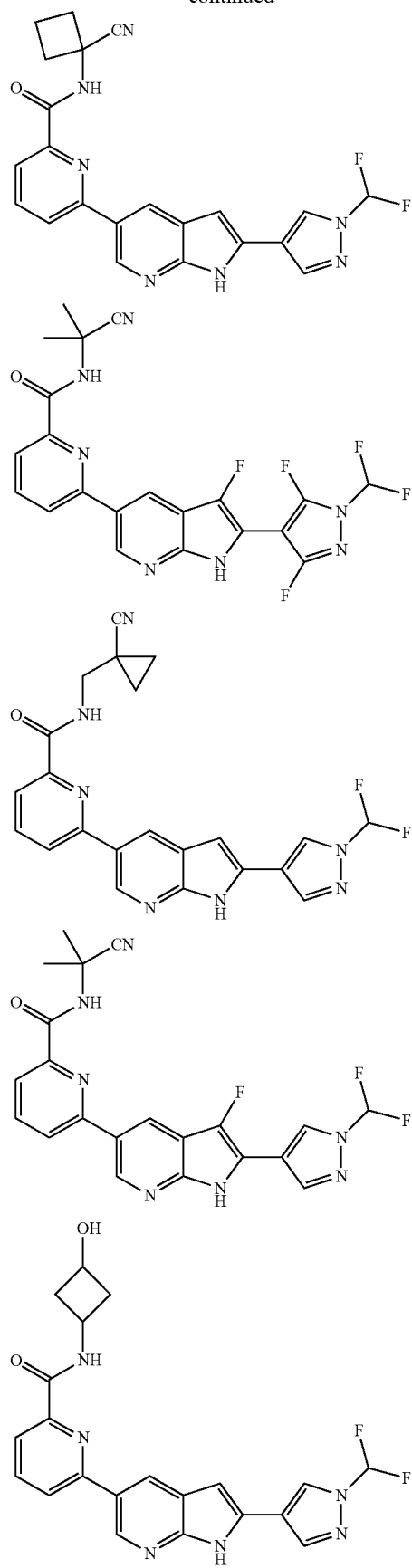
164
-continued
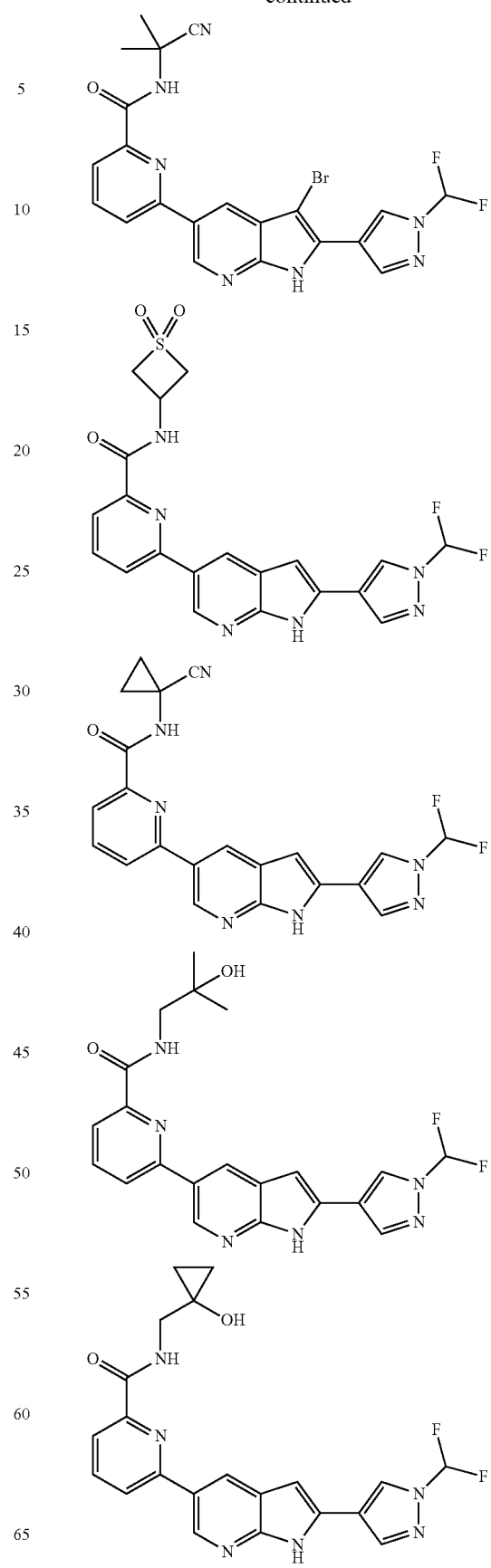

165
-continued
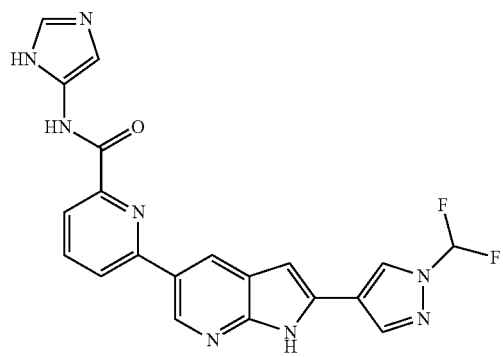
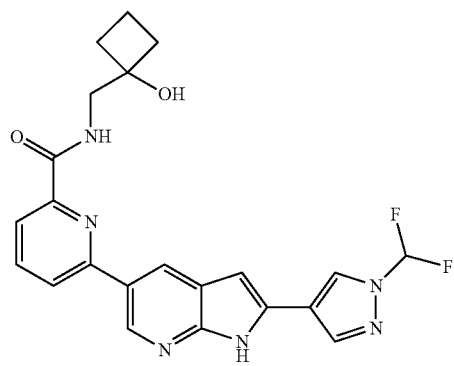
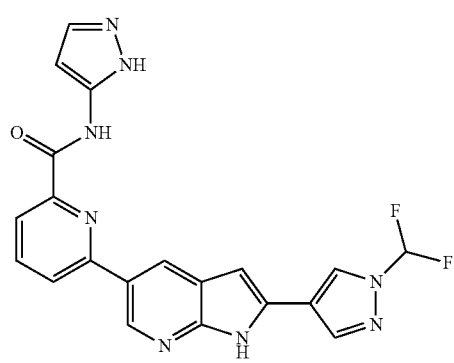
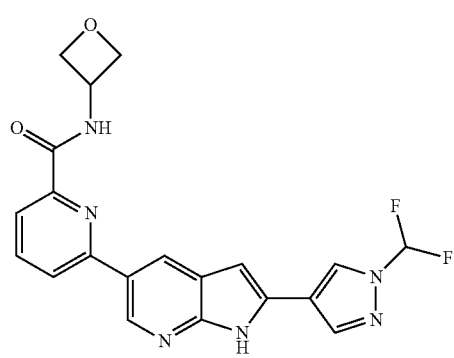
166
-continued
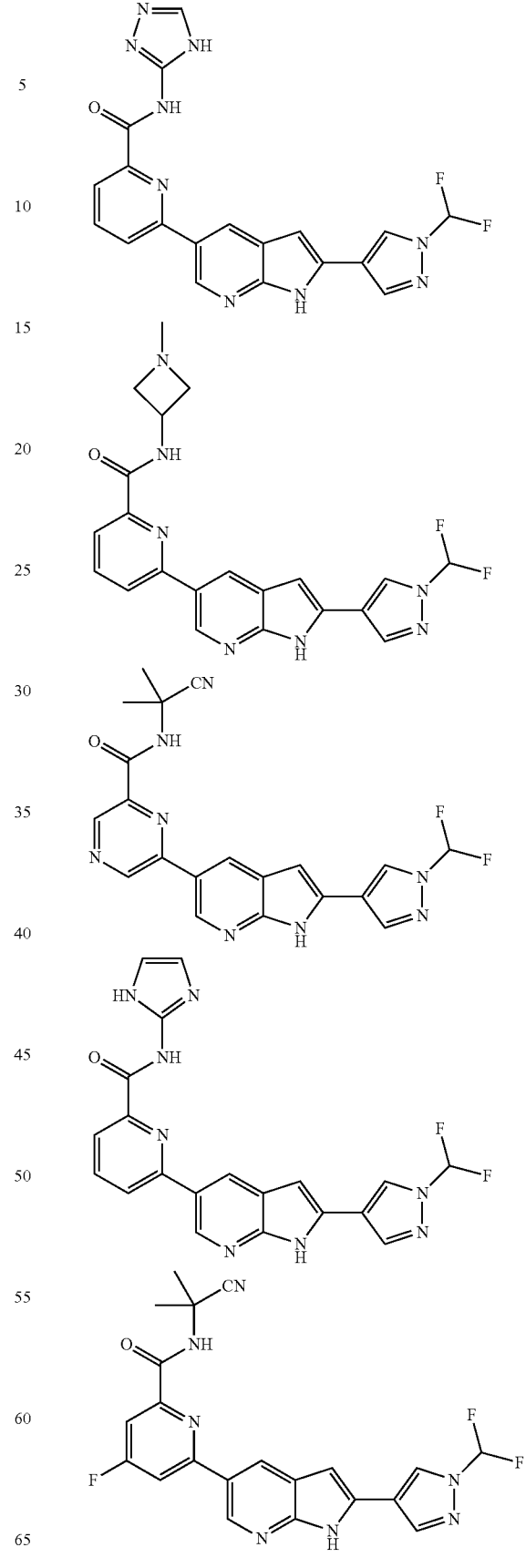

or a pharmaceutically acceptable salt, a solvate, a tautomer, a stereoisomer, or a deuterated analog of any one of the above compounds.

17. A pharmaceutical composition comprising a compound according to claim 1, and a pharmaceutically acceptable carrier.

18. The pharmaceutical composition according to claim 17, further comprising a second pharmaceutical agent selected from: an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an antibody therapy agent selected from alemtuzumab, bevacizumab, cetuximab, galiximab, gemtuzumab, nivolumab, ipilimumab, panitumumab, pembrolizumab, pertuzumab, rituximab, tositumomab, trastuzumab, and 90 Y ibritumomab tiuxetan; v) a hormone or hormone antagonist selected from the group consisting of anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxycamptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor, and an aromatase inhibitor; xv) a Mek inhibitor; xvi) a tyrosine kinase inhibitor; xvii) an EGFR inhibitor; and xviii) an anti-retroviral agent selected from entry inhibitors, fusion inhibitors, reverse transcriptase inhibitors, nucleoside/nucleotide reverse transcriptase inhibitors, non-nucleoside reverse transcriptase inhibitors, integrase inhibitors, protease inhibitors, and multi-class combination products.

* * * * *